(12) United States Patent
Nakai et al.

(10) Patent No.: US 7,109,342 B2
(45) Date of Patent: Sep. 19, 2006

(54) PIPERIDINE DERIVATIVES AND AGENT COMPRISING THE DERIVATIVE AS ACTIVE INGREDIENT

(75) Inventors: Hisao Nakai, Mishima-gun (JP); Katsuya Kishikawa, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 242 days.

(21) Appl. No.: 10/343,956

(22) PCT Filed: Aug. 9, 2001

(86) PCT No.: PCT/JP01/06861

§ 371 (c)(1),
(2), (4) Date: Sep. 2, 2003

(87) PCT Pub. No.: WO02/14280

PCT Pub. Date: Feb. 21, 2002

(65) Prior Publication Data

US 2004/0044036 A1    Mar. 4, 2004

(30) Foreign Application Priority Data

Aug. 11, 2000 (JP) ............... 2000-243881
Nov. 24, 2000 (JP) ............... 2000-357517

(51) Int. Cl.
*C07D 211/08* (2006.01)
*C07D 211/56* (2006.01)

(52) U.S. Cl. .............. 546/192; 546/215; 546/229; 546/237

(58) Field of Classification Search ........... 546/192, 546/215, 229, 237

See application file for complete search history.

(56) References Cited

U.S. PATENT DOCUMENTS 5,459,151 A   10/1995   Lombardo
5,602,173 A   2/1997   Christensen, IV

FOREIGN PATENT DOCUMENTS

WO   WO 93/19747   10/1993
WO   WO 94/25437   11/1994

*Primary Examiner*—D. Margaret Seaman
(74) *Attorney, Agent, or Firm*—Sughrue Mion, PLLC

(57) ABSTRACT

Piperidine derivatives represented by formula (I) or nontoxic salts thereof (wherein symbols are defined in the description):

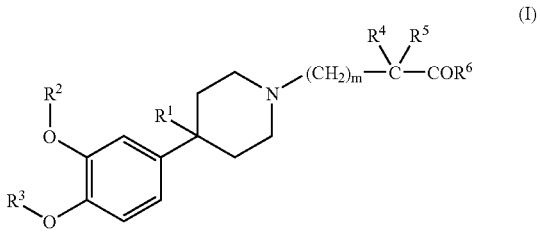

Since the compound represented by formula (I) has a PDE4 inhibitory activity, it is useful for preventing and/or treating inflammatory diseases, diabetic diseases, allergic diseases, autoimmune diseases, osteoporosis, bone fracture, obesity, depression, Parkinson's disease, dementia, ischemia-reperfusion injury, leukemia and the like.

10 Claims, No Drawings

PIPERIDINE DERIVATIVES AND AGENT COMPRISING THE DERIVATIVE AS ACTIVE INGREDIENT

TECHNICAL FIELD

The present invention relates to piperidine derivatives.
More specifically, the present invention relates to
(1) piperidine derivatives represented by formula (I):

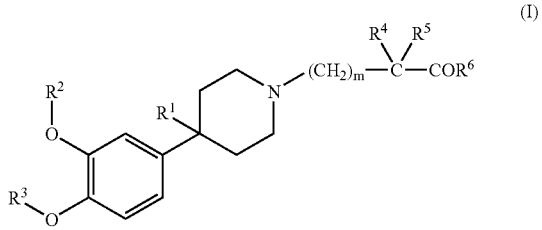

(wherein all symbols have the same meanings as described below), or nontoxic salts thereof,
(2) a process for preparing thereof, and
(3) an agent comprising thereof as an active ingredient.

BACKGROUND ART

Cyclic adenosine 3',5'-monophosphate (cAMP) and cyclic guanosine 3',5'-monophosphate (cGMP) as intracellular signal transduction molecules (second messengers) are degraded by a group of hydrolases generally called phosphodiesterase (PDE) into inactive 5'-AMP and 5'-GMP, respectively.

PDE isozymes which inactivate them are not uniformly present in vivo but distributed in vivo having an organ-specific localization by showing differences, e.g., in cell distribution and tissue distribution.

Up to date, the presence of 11 families of PDE1 to PDE11 has been confirmed (see Current Opinion in Cell Biology, 12, 174–179 (2000)).

Among these PDEs, PDE4 is present in various cells such as airway smooth muscle cells, epitherial cells, inflammatory cells (macrophages, neutrophils and eosinophils) and T lymphocytes, and controls cellular functions by regulating the intracellular cAMP level of these cells. On the other hand, other PDEs such as PDE5 are present in, e.g., platelets, cardiac muscle cells and vascular smooth muscle cells and participates in the control of circulatory organ system by regulating intracellular cGMP or cAMP level.

Thus, it is known that PDE4 inhibitors have bronchodilatory activity, anti-inflammatory activity, mediator release inhibitory activity, immunosuppressive activity and the like, because they cause accumulation of intracellular cAMP by inhibiting degradation of cAMP by PDE4.

Accordingly, it is considered that agents which specifically inhibit PDE4 do not show the activities of other PDE inhibitors such as PDE5 upon circulatory organs and are useful in preventing and/or treating various diseases such as inflammatory diseases (e.g., asthma, obstructive lung disease, sepsis, sarcoidosis, nephritis, hepatitis, enteritis, etc.), diabetic diseases, allergic diseases (e.g., allergic rhinitis, allergic conjunctivitis, seasonal conjunctivitis, atopic dermatitis, etc.), autoimmune diseases (e.g., ulcerative colitis, Crohn's disease, rheumatism, psoriasis, multiple sclerosis, collagen disease, etc.), osteoporosis, bone fracture, obesity, depression, Parkinson's disease, dementia, ischemia-reperfusion injury, leukemia and AIDS (Exp. Opin. Invest. Drugs, 8,1301–1325 (1999)).

As the PDE4 inhibitors, for example, the specification of JP-T-8-509731 discloses that a compound represented by formula (A):

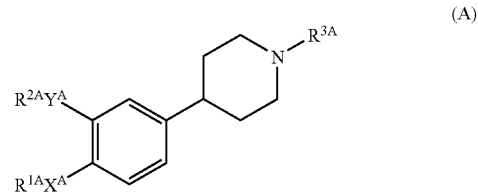

(wherein $R^{1A}$ represents H or C1–6 alkyl; $R^{2A}$ represents C3–7 alkyl, C3–7 cycloalkyl, etc.; $D^{3A}$ represents $COR^{4A}$, $COCOR^{4A}$, etc.; $R^{4A}$ represents H, $OR^{5A}$, NHOH, etc.; $R^{5A}$ represents H, C1–6 alkyl, etc.; $X^{A}$ represents O, etc.; and $Y^{A}$ represents O, etc.) or a pharmaceutically acceptable salt thereof has a PDE4 inhibitory activity (necessary parts were extracted from the description of groups).

Also, the specification of WO 93/19747 discloses that a compound represented by formula (B):

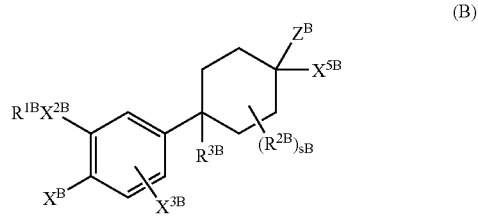

(wherein $R^{1B}$ represents $—(CR^{4B}R^{5B})_{rB}R^{6B}$; rB is 1 to 6; $R^{4B}$ and $R^{5B}$ each independently represents a hydrogen atom or a C1–2 alkyl group; $R^{6B}$ represents a hydrogen atom, a C3–6 cycloalkyl group, etc.; $X^{B}$ represents $Y^{B}R^{2B}$, etc.; $Y^{B}$ represents O, etc.; $R^{2B}$ represents methyl, ethyl, etc.; $X^{2B}$ represents O, etc.; $X^{3B}$ represents a hydrogen atom, etc.; sB is 0 to 4; $R^{3B}$ represents a hydrogen atom, CN, etc.; $X^{5B}$ represents a hydrogen atom, etc.; $Z^{B}$ represents $CR^{8B}R^{8B}C(O)OR^{14B}$, $CR^{8B}R^{8B}C(Y^{B})NR^{10B}R^{14B}$, etc.; $R^{8B}$ a hydrogen atom, etc.; $R^{10B}$ represents a hydrogen atom, $OR^{8B}$, etc.; and $R^{14B}$ represents a hydrogen atom, etc.) or a pharmaceutically acceptable salt thereof has a PDE4 inhibitory activity (necessary parts were extracted from the description of groups).

Also, the specification of WO 93/19749 discloses that a compound represented by formula (C):

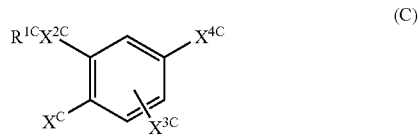

(wherein $R^{1C}$ represents $—(CR^{4C}R^{5C})_{rC}R^{6C}$, etc.; rC is 1 to 6; $R^{4C}$ and $R^{5C}$ each independently represents a hydrogen atom or a C1–2 alkyl group; $R^{6C}$ represents a hydrogen atom, a C3–6 cycloalkyl group, etc.; $X^{C}$ represents $Y^{C}R^{2C}$, etc.; $Y^C$ represents O, etc.; $R^{2C}$ represents methyl, ethyl, etc.; $X^{2C}$ represents O, etc.; $X^{3C}$ represents a hydrogen atom, etc.; $X^{4C}$ represents

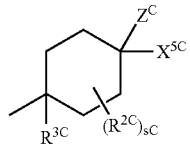

etc.; $R^{3C}$ represents a hydrogen atom, CN, etc.; $X^{5C}$ represents a hydrogen atom, etc.; sC is 0 to 4; $Z^C$ represents $C(O)OR^{14C}$, $C(Y^{rC})NR^{10C}R^{14C}$, etc.; $R^{10C}$ represents a hydrogen atom $OR^{8C}$, etc.; $R^{8C}$ represents a hydrogen atom, etc.; and $R^{14C}$ represents a hydrogen atom, etc.) or a pharmaceutically acceptable salt thereof has a PDE4 inhibitory activity (necessary parts were extracted from the description of groups).

DISCLOSURE OF THE INVENTION

In order to find a compound having a PDE4 inhibitory activity, the present inventors have conducted intensive studies and found, as a result, that the objects can be accomplished by piperidine derivatives represented by formula (I), and thus the present invention has been accomplished.

The present invention relates to
(1) piperidine derivatives represented by formula (I):

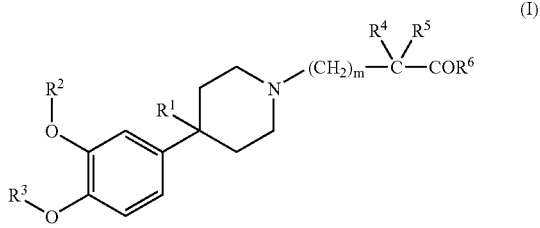

(wherein $R^1$ represents 1) a hydrogen atom or 2) a cyano group;
$R^2$ and $R^3$ each independently represents 1) a C1–8 alkyl group, 2) a C3–7 cycloalkyl group, 3) a C1–8 alkyl group substituted with a C3–7 cycloalkyl group, 4) a C1–8 alkyl group substituted with 1 to 3 halogen atom(s), 5) a hydrogen atom, 6) a C1–8 alkyl group substituted with a phenyl group, 7) a C1–8 alkyl group substituted with a C1–8 alkoxy group, or

8)

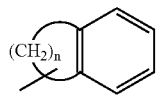

(in which n represents 1 to 5.);
$R^4$ and $R^5$ each independently represents 1) a hydrogen atom or 2) a C1–8 alkyl group, or
$R^4$ and $R^5$ are taken together with the binding carbon atom to represent a C3–7 saturated carbocyclic ring;
$R^6$ represents 1) a hydroxyl group, 2) a C1–8 alkoxy group, 3) —NHOH, or 4) a C1–8 alkoxy group substituted with a phenyl group; and
m is 0 or an integer of 1 to 4.)
or a nontoxic salt thereof, (2) a process for preparing thereof, and
(3) an agent comprising thereof as an active ingredient.

DETAILED DESCRIPTION OF THE INVENTION

In formula (I), the C1–8 alkyl group includes methyl, ethyl, propyl, butyl, pentyl, hexyl, heptyl, and octyl groups, and isomers thereof.

In formula (I), the C1–8 alkoxy group includes methoxy, ethoxy, propoxy, butoxy, pentyloxy, hexyloxy, heptyloxy, and octyloxy groups, and isomers thereof.

In the present invention, the halogen atom means a chlorine, bromine, fluorine or iodine atom.

In formula (I), the C3–7 cycloalkyl group includes cyclopropyl, cyclobutyl, cyclopentyl, cyclohexyl, cycloheptyl, and cyclooctyl groups.

In formula (I), the C3–7 saturated carbocyclic ring represented by $R^4$ and $R^5$ taken together the binding carbon atom includes C3–7 cycloalkyl groups such as cyclopropyl, cyclobutyl, cyclopentyl, cyclohexyl, cycloheptyl, and cyclooctyl groups.

Unless otherwise indicated, all isomers are included in the present invention. For example, the alkyl group, the alkoxy group and the alkylene group include straight-chain groups and branched-chain groups. Moreover, isomers in a double bond, a ring, a fused ring (E-, Z-, cis-, trans-isomer), isomers due to the presence of an asymmetric carbon atom(s), etc. (R-, S-isomer, α-, β-isomer, enantiomer, diastereomer), optically active isomers having optical rotation (D-, L-, d-, l-isomer), polar compounds separated by chromatography (high polar compound, low polar compound), equilibrium compounds, mixtures thereof at arbitrary ratios and racemic mixtures are included in the present invention.

According to the present invention, unless otherwise indicated and as is apparent for those skilled in the art, symbol ⋰
indicates that it is bound to the opposite side of the sheet
(namely α-configuration), symbol ⌿
indicates that it is bound to the front side of the sheet
(namely β-configuration), symbol ⌇
indicates that it is α-, β- or a mixture thereof, and
symbol ╱
indicates that it is a mixture of α-configuration and β-configuration.

The compound represented by formula (I) can be converted into a nontoxic salt by known methods.

In the present specification, the nontoxic salt includes alkaline metal salts, alkaline earth metal salts, ammonium salts, amine salts, acid-addition salts, and the like.

The salt is preferably nontoxic and water-soluble. Appropriate salts include salts of alkali metals (e.g., potassium, sodium, etc.), salts of alkaline earth metals (e.g., calcium, magnesium, etc.), ammonium salts, and pharmaceutically acceptable organic amines (e.g., tetramethylammonium, triethylamine, methylamine, dimethylamine, cyclopentylamine, benzylamine, phenethylamine, piperidine, monoethanolamine, diethanolamine, tris(hydroxymethyl) aminomethane, lysine, arginine, N-methyl-D-glucamine, etc.).

The acid-addition salt is preferably nontoxic and water-soluble. Appropriate acid-addition salts include inorganic acid salts such as hydrochloride, hydrobromate, hydroiodate, sulfate, phosphate, and nitrate; and organic acid salts such as acetate, lactate, tartarate, benzoate, citrate, methane sulfonate, ethane sulfonate, benzene sulfonate, toluene sulfonate, isethionate, glucuronate, and gluconate.

Furthermore, the compound of the present invention represented by formula (I) or a salt thereof can be converted into a solvate by known methods.

The solvate is preferably nontoxic and water-soluble. Appropriate solvates include solvates such as water and an alcohol solvent (e.g., ethanol, etc.).

In formula (I), $R^1$ is preferably a cyano group.

In formula (I), $R^2$ is preferably a C1–8 alkyl group, a C3–7 cycloalkyl group, or a C1–8 alkyl group substituted with a C3–7 cycloalkyl group, and more preferably a methyl group, an ethyl group, an isopropyl group, a 2-methylpropyl group, a cyclobutyl group, a cyclopentyl group, or a cyclopropylmethyl group.

In formula (I), $R^3$ is preferably a C1–8 alkyl group or a C1–8 alkyl group substituted with a 1–3 halogen atom(s), and more preferably a methyl group, an ethyl group, an isopropyl group, a 2-methylpropyl group, or a difluoromethyl group.

In formula (I), $R^4$ and $R^5$ are preferably hydrogen atoms.

In formula (I), $R^6$ is preferably a hydroxyl group or —NHOH, and more preferably —NHOH.

Among the compounds of the present invention represented by formula (I), preferred compounds are compounds represented by formula (I-A):

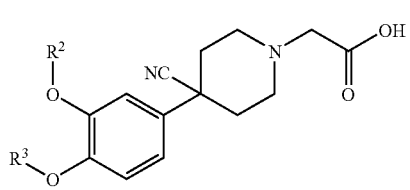

(I-A)

(wherein all symbols have the same meanings as described above), compounds represented by formula (I-B):

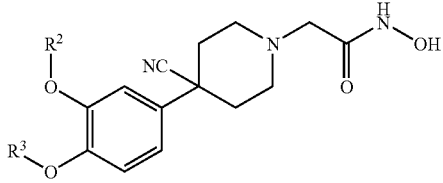

(I-B)

(wherein all symbols have the same meanings as described above), compounds represented by formula (I-C):

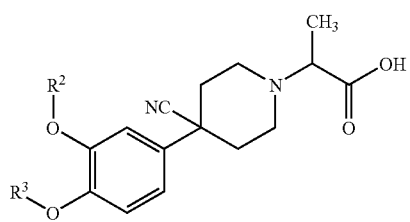

(I-C)

(wherein all symbols have the same meanings as described above), compounds represented by formula (I-D):

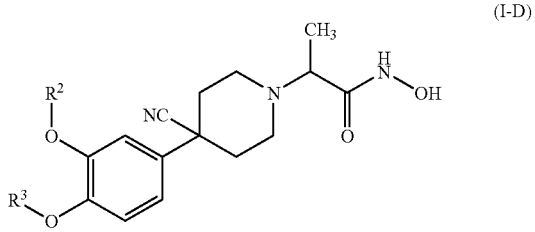

(I-D)

(wherein all symbols have the same meanings as described above), compounds represented by formula (I-E):

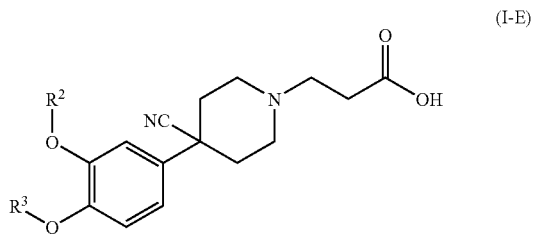

(I-E)

(wherein all symbols have the same meanings as described above), compounds represented by formula (I-F):

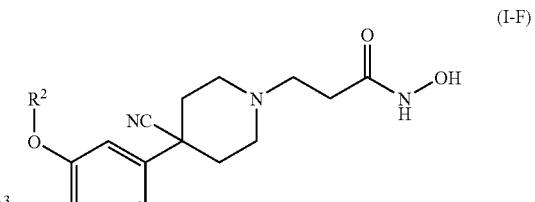

(I-F)

(wherein all symbols have the same meanings as described above), compounds represented by formula (I-G):

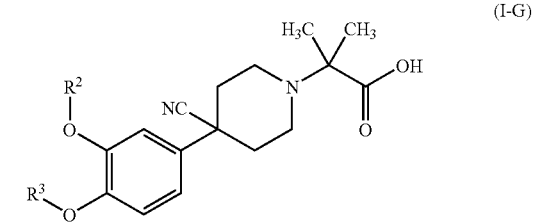

(I-G)

(wherein all symbols have the same meanings as described above), compounds represented by formula (I-H):

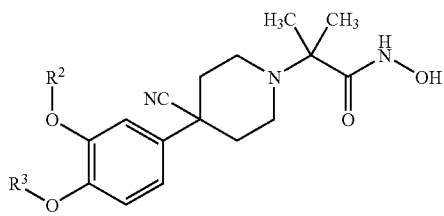

(I-H)

(wherein all symbols have the same meanings as described above), compounds represented by formula (I-J):

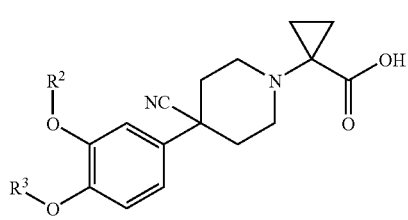

(I-J)

(wherein all symbols have the same meanings as described above), and compounds represented by formula (I-K):

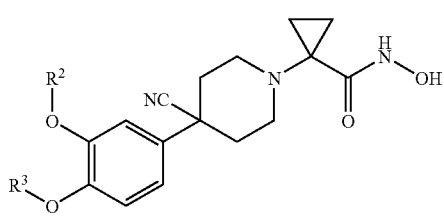

(I-K)

(wherein all symbols have the same meanings as described above).

Concrete compounds of the present invention include compounds shown in Tables 1 to 10, compounds described in Examples, and nontoxic salts, acid-addition salts and solvates thereof.

Also, in each Table, Me represents a methyl group; Et represents an ethyl group; i-Pr represents an isopropyl group; $CH_2$-c-Pr represents a cyclopropylmethyl group; $CH_2$c-Pen represents a cyclopentylmethyl group; c-Bu represents a cyclobutyl group; c-Pen represents a cyclopentyl group; $CHF_2$ represents a difluoromethyl group; and other symbols have the same meanings as described above.

TABLE 1

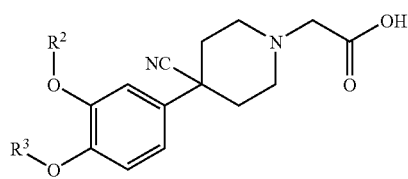

(I-A)

| No. | $R^2$ | $R^3$ |
|---|---|---|
| 1 | Me | Me |
| 2 | Me | Et |
| 3 | Me | i-Pr |
| 4 | Me | $CH_2$-c-Pr |
| 5 | Me | $CH_2$-c-Pen |
| 6 | Me | c-Bu |
| 7 | Me | c-Pen |
| 8 | Me | $CHF_2$ |
| 9 | Et | Me |
| 10 | Et | Et |
| 11 | Et | i-Pr |
| 12 | Et | $CH_2$-c-Pr |
| 13 | Et | $CH_2$-c-Pen |
| 14 | Et | c-Bu |
| 15 | Et | c-Pen |
| 16 | Et | $CHF_2$ |
| 17 | i-Pr | Me |
| 18 | i-Pr | Et |
| 19 | i-Pr | i-Pr |
| 20 | i-Pr | $CH_2$-c-Pr |
| 21 | i-Pr | $CH_2$-c-Pen |
| 22 | i-Pr | c-Bu |
| 23 | i-Pr | c-Pen |
| 24 | i-Pr | $CHF_2$ |
| 25 | $CH_2$-c-Pr | Me |
| 26 | $CH_2$-c-Pr | Et |
| 27 | $CH_2$-c-Pr | i-Pr |
| 28 | $CH_2$-c-Pr | $CH_2$-c-Pr |
| 29 | $CH_2$-c-Pr | $CH_2$-c-Pen |
| 30 | $CH_2$-c-Pr | c-Bu |
| 31 | $CH_2$-c-Pr | c-Pen |
| 32 | $CH_2$-c-Pr | $CHF_2$ |
| 33 | $CH_2$-c-Pen | Me |
| 34 | $CH_2$-c-Pen | Et |
| 35 | $CH_2$-c-Pen | i-Pr |
| 36 | $CH_2$-c-Pen | $CH_2$-c-Pr |
| 37 | $CH_2$-c-Pen | $CH_2$-c-Pen |
| 38 | $CH_2$-c-Pen | c-Bu |
| 39 | $CH_2$-c-Pen | c-Pen |
| 40 | $CH_2$-c-Pen | $CHF_2$ |
| 41 | c-Bu | Me |
| 42 | c-Bu | Et |
| 43 | c-Bu | i-Pr |
| 44 | c-Bu | $CH_2$-c-Pr |
| 45 | c-Bu | $CH_2$-c-Pen |
| 46 | c-Bu | c-Bu |
| 47 | c-Bu | c-Pen |
| 48 | c-Bu | $CHF_2$ |
| 49 | c-Pen | Me |
| 50 | c-Pen | Et |
| 51 | c-Pen | i-Pr |
| 52 | c-Pen | $CH_2$-c-Pr |
| 53 | c-Pen | $CH_2$-c-Pen |
| 54 | c-Pen | c-Bu |
| 55 | c-Pen | c-Pen |
| 56 | c-Pen | $CHF_2$ |
| 57 | $CHF_2$ | Me |
| 58 | $CHF_2$ | Et |
| 59 | $CHF_2$ | i-Pr |
| 60 | $CHF_2$ | $CH_2$-c-Pr |
| 61 | $CHF_2$ | $CH_2$-c-Pen |
| 62 | $CHF_2$ | c-Bu |
| 63 | $CHF_2$ | c-Pen |
| 64 | $CHF_2$ | $CHF_2$ |

TABLE 2

(I-B)

| No. | R² | R³ |
|---|---|---|
| 1 | Me | Me |
| 2 | Me | Et |
| 3 | Me | i-Pr |
| 4 | Me | CH₂-c-Pr |
| 5 | Me | CH₂-c-Pen |
| 6 | Me | c-Bu |
| 7 | Me | c-Pen |
| 8 | Me | CHF₂ |
| 9 | Et | Me |
| 10 | Et | Et |
| 11 | Et | i-Pr |
| 12 | Et | CH₂-c-Pr |
| 13 | Et | CH₂-c-Pen |
| 14 | Et | c-Bu |
| 15 | Et | c-Pen |
| 16 | Et | CHF₂ |
| 17 | i-Pr | Me |
| 18 | i-Pr | Et |
| 19 | i-Pr | i-Pr |
| 20 | i-Pr | CH₂-c-Pr |
| 21 | i-Pr | CH₂-c-Pen |
| 22 | i-Pr | c-Bu |
| 23 | i-Pr | c-Pen |
| 24 | i-Pr | CHF₂ |
| 25 | CH₂-c-Pr | Me |
| 26 | CH₂-c-Pr | Et |
| 27 | CH₂-c-Pr | i-Pr |
| 28 | CH₂-c-Pr | CH₂-c-Pr |
| 29 | CH₂-c-Pr | CH₂-c-Pen |
| 30 | CH₂-c-Pr | c-Bu |
| 31 | CH₂-c-Pr | c-Pen |
| 32 | CH₂-c-Pr | CHF₂ |
| 33 | CH₂-c-Pen | Me |
| 34 | CH₂-c-Pen | Et |
| 35 | CH₂-c-Pen | i-Pr |
| 36 | CH₂-c-Pen | CH₂-c-Pr |
| 37 | CH₂-c-Pen | CH₂-c-Pen |
| 38 | CH₂-c-Pen | c-Bu |
| 39 | CH₂-c-Pen | c-Pen |
| 40 | CH₂-c-Pen | CHF₂ |
| 41 | c-Bu | Me |
| 42 | c-Bu | Et |
| 43 | c-Bu | i-Pr |
| 44 | c-Bu | CH₂-c-Pr |
| 45 | c-Bu | CH₂-c-Pen |
| 46 | c-Bu | c-Bu |
| 47 | c-Bu | c-Pen |
| 48 | c-Bu | CHF₂ |
| 49 | c-Pen | Me |
| 50 | c-Pen | Et |
| 51 | c-Pen | i-Pr |
| 52 | c-Pen | CH₂-c-Pr |
| 53 | c-Pen | CH₂-c-Pen |
| 54 | c-Pen | c-Bu |
| 55 | c-Pen | c-Pen |
| 56 | c-Pen | CHF₂ |
| 57 | CHF₂ | Me |
| 58 | CHF₂ | Et |
| 59 | CHF₂ | i-Pr |
| 60 | CHF₂ | CH₂-c-Pr |
| 61 | CHF₂ | CH₂-c-Pen |
| 62 | CHF₂ | c-Bu |
| 63 | CHF₂ | c-Pen |
| 64 | CHF₂ | CHF₂ |

TABLE 3

(I-C)

| No. | R² | R³ |
|---|---|---|
| 1 | Me | Me |
| 2 | Me | Et |
| 3 | Me | i-Pr |
| 4 | Me | CH₂-c-Pr |
| 5 | Me | CH₂-c-Pen |
| 6 | Me | c-Bu |
| 7 | Me | c-Pen |
| 8 | Me | CHF₂ |
| 9 | Et | Me |
| 10 | Et | Et |
| 11 | Et | i-Pr |
| 12 | Et | CH₂-c-Pr |
| 13 | Et | CH₂-c-Pen |
| 14 | Et | c-Bu |
| 15 | Et | c-Pen |
| 16 | Et | CHF₂ |
| 17 | i-Pr | Me |
| 18 | i-Pr | Et |
| 19 | i-Pr | i-Pr |
| 20 | i-Pr | CH₂-c-Pr |
| 21 | i-Pr | CH₂-c-Pen |
| 22 | i-Pr | c-Bu |
| 23 | i-Pr | c-Pen |
| 24 | i-Pr | CHF₂ |
| 25 | CH₂-c-Pr | Me |
| 26 | CH₂-c-Pr | Et |
| 27 | CH₂-c-Pr | i-Pr |
| 28 | CH₂-c-Pr | CH₂-c-Pr |
| 29 | CH₂-c-Pr | CH₂-c-Pen |
| 30 | CH₂-c-Pr | c-Bu |
| 31 | CH₂-c-Pr | c-Pen |
| 32 | CH₂-c-Pr | CHF₂ |
| 33 | CH₂-c-Pen | Me |
| 34 | CH₂-c-Pen | Et |
| 35 | CH₂-c-Pen | i-Pr |
| 36 | CH₂-c-Pen | CH₂-c-Pr |
| 37 | CH₂-c-Pen | CH₂-c-Pen |
| 38 | CH₂-c-Pen | c-Bu |
| 39 | CH₂-c-Pen | c-Pen |
| 40 | CH₂-c-Pen | CHF₂ |
| 41 | c-Bu | Me |
| 42 | c-Bu | Et |
| 43 | c-Bu | i-Pr |
| 44 | c-Bu | CH₂-c-Pr |
| 45 | c-Bu | CH₂-c-Pen |
| 46 | c-Bu | c-Bu |
| 47 | c-Bu | c-Pen |
| 48 | c-Bu | CHF₂ |
| 49 | c-Pen | Me |
| 50 | c-Pen | Et |
| 51 | c-Pen | i-Pr |
| 52 | c-Pen | CH₂-c-Pr |
| 53 | c-Pen | CH₂-c-Pen |
| 54 | c-Pen | c-Bu |
| 55 | c-Pen | c-Pen |
| 56 | c-Pen | CHF₂ |
| 57 | CHF₂ | Me |
| 58 | CHF₂ | Et |
| 59 | CHF₂ | i-Pr |
| 60 | CHF₂ | CH₂-c-Pr |
| 61 | CHF₂ | CH₂-c-Pen |
| 62 | CHF₂ | c-Bu |
| 63 | CHF₂ | c-Pen |
| 64 | CHF₂ | CHF₂ |

TABLE 4

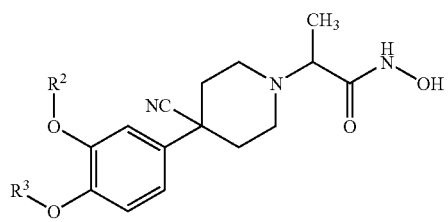
(I-D)

| No. | R² | R³ |
|---|---|---|
| 1 | Me | Me |
| 2 | Me | Et |
| 3 | Me | i-Pr |
| 4 | Me | CH₂-c-Pr |
| 5 | Me | CH₂-c-Pen |
| 6 | Me | c-Bu |
| 7 | Me | c-Pen |
| 8 | Me | CHF₂ |
| 9 | Et | Me |
| 10 | Et | Et |
| 11 | Et | i-Pr |
| 12 | Et | CH₂-c-Pr |
| 13 | Et | CH₂-c-Pen |
| 14 | Et | c-Bu |
| 15 | Et | c-Pen |
| 16 | Et | CHF₂ |
| 17 | i-Pr | Me |
| 18 | i-Pr | Et |
| 19 | i-Pr | i-Pr |
| 20 | i-Pr | CH₂-c-Pr |
| 21 | i-Pr | CH₂-c-Pen |
| 22 | i-Pr | c-Bu |
| 23 | i-Pr | c-Pen |
| 24 | i-Pr | CHF₂ |
| 25 | CH₂-c-Pr | Me |
| 26 | CH₂-c-Pr | Et |
| 27 | CH₂-c-Pr | i-Pr |
| 28 | CH₂-c-Pr | CH₂-c-Pr |
| 29 | CH₂-c-Pr | CH₂-c-Pen |
| 30 | CH₂-c-Pr | c-Bu |
| 31 | CH₂-c-Pr | c-Pen |
| 32 | CH₂-c-Pr | CHF₂ |
| 33 | CH₂-c-Pen | Me |
| 34 | CH₂-c-Pen | Et |
| 35 | CH₂-c-Pen | i-Pr |
| 36 | CH₂-c-Pen | CH₂-c-Pr |
| 37 | CH₂-c-Pen | CH₂-c-Pen |
| 38 | CH₂-c-Pen | c-Bu |
| 39 | CH₂-c-Pen | c-Pen |
| 40 | CH₂-c-Pen | CHF₂ |
| 41 | c-Bu | Me |
| 42 | c-Bu | Et |
| 43 | c-Bu | i-Pr |
| 44 | c-Bu | CH₂-c-Pr |
| 45 | c-Bu | CH₂-c-Pen |
| 46 | c-Bu | c-Bu |
| 47 | c-Bu | c-Pen |
| 48 | c-Bu | CHF₂ |
| 49 | c-Pen | Me |
| 50 | c-Pen | Et |
| 51 | c-Pen | i-Pr |
| 52 | c-Pen | CH₂-c-Pr |
| 53 | c-Pen | CH₂-c-Pen |
| 54 | c-Pen | c-Bu |
| 55 | c-Pen | c-Pen |
| 56 | c-Pen | CHF₂ |
| 57 | CHF₂ | Me |
| 58 | CHF₂ | Et |
| 59 | CHF₂ | i-Pr |
| 60 | CHF₂ | CH₂-c-Pr |
| 61 | CHF₂ | CH₂-c-Pen |
| 62 | CHF₂ | c-Bu |
| 63 | CHF₂ | c-Pen |
| 64 | CHF₂ | CHF₂ |

TABLE 5

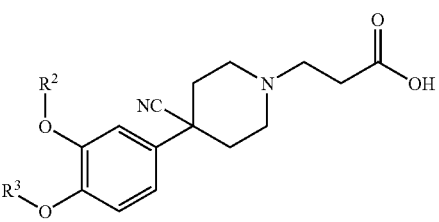
(I-E)

| No. | R² | R³ |
|---|---|---|
| 1 | Me | Me |
| 2 | Me | Et |
| 3 | Me | i-Pr |
| 4 | Me | CH₂-c-Pr |
| 5 | Me | CH₂-c-Pen |
| 6 | Me | c-Bu |
| 7 | Me | c-Pen |
| 8 | Me | CHF₂ |
| 9 | Et | Me |
| 10 | Et | Et |
| 11 | Et | i-Pr |
| 12 | Et | CH₂-c-Pr |
| 13 | Et | CH₂-c-Pen |
| 14 | Et | c-Bu |
| 15 | Et | c-Pen |
| 16 | Et | CHF₂ |
| 17 | i-Pr | Me |
| 18 | i-Pr | Et |
| 19 | i-Pr | i-Pr |
| 20 | i-Pr | CH₂-c-Pr |
| 21 | i-Pr | CH₂-c-Pen |
| 22 | i-Pr | c-Bu |
| 23 | i-Pr | c-Pen |
| 24 | i-Pr | CHF₂ |
| 25 | CH₂-c-Pr | Me |
| 26 | CH₂-c-Pr | Et |
| 27 | CH₂-c-Pr | i-Pr |
| 28 | CH₂-c-Pr | CH₂-c-Pr |
| 29 | CH₂-c-Pr | CH₂-c-Pen |
| 30 | CH₂-c-Pr | c-Bu |
| 31 | CH₂-c-Pr | c-Pen |
| 32 | CH₂-c-Pr | CHF₂ |
| 33 | CH₂-c-Pen | Me |
| 34 | CH₂-c-Pen | Et |
| 35 | CH₂-c-Pen | i-Pr |
| 36 | CH₂-c-Pen | CH₂-c-Pr |
| 37 | CH₂-c-Pen | CH₂-c-Pen |
| 38 | CH₂-c-Pen | c-Bu |
| 39 | CH₂-c-Pen | c-Pen |
| 40 | CH₂-c-Pen | CHF₂ |
| 41 | c-Bu | Me |
| 42 | c-Bu | Et |
| 43 | c-Bu | i-Pr |
| 44 | c-Bu | CH₂-c-Pr |
| 45 | c-Bu | CH₂-c-Pen |
| 46 | c-Bu | c-Bu |
| 47 | c-Bu | c-Pen |
| 48 | c-Bu | CHF₂ |
| 49 | c-Pen | Me |
| 50 | c-Pen | Et |
| 51 | c-Pen | i-Pr |
| 52 | c-Pen | CH₂-c-Pr |
| 53 | c-Pen | CH₂-c-Pen |
| 54 | c-Pen | c-Bu |
| 55 | c-Pen | c-Pen |
| 56 | c-Pen | CHF₂ |
| 57 | CHF₂ | Me |
| 58 | CHF₂ | Et |
| 59 | CHF₂ | i-Pr |
| 60 | CHF₂ | CH₂-c-Pr |
| 61 | CHF₂ | CH₂-c-Pen |
| 62 | CHF₂ | c-Bu |
| 63 | CHF₂ | c-Pen |
| 64 | CHF₂ | CHF₂ |

TABLE 6

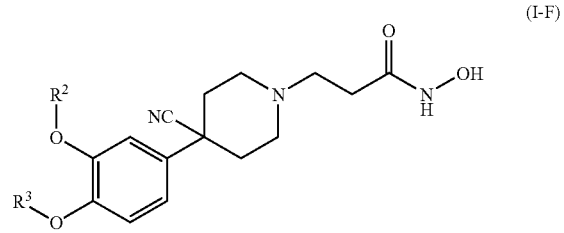

(I-F)

| No. | R² | R³ |
|---|---|---|
| 1 | Me | Me |
| 2 | Me | Et |
| 3 | Me | i-Pr |
| 4 | Me | CH₂-c-Pr |
| 5 | Me | CH₂-c-Pen |
| 6 | Me | c-Bu |
| 7 | Me | c-Pen |
| 8 | Me | CHF₂ |
| 9 | Et | Me |
| 10 | Et | Et |
| 11 | Et | i-Pr |
| 12 | Et | CH₂-c-Pr |
| 13 | Et | CH₂-c-Pen |
| 14 | Et | c-Bu |
| 15 | Et | c-Pen |
| 16 | Et | CHF₂ |
| 17 | i-Pr | Me |
| 18 | i-Pr | Et |
| 19 | i-Pr | i-Pr |
| 20 | i-Pr | CH₂-c-Pr |
| 21 | i-Pr | CH₂-c-Pen |
| 22 | i-Pr | c-Bu |
| 23 | i-Pr | c-Pen |
| 24 | i-Pr | CHF₂ |
| 25 | CH₂-c-Pr | Me |
| 26 | CH₂-c-Pr | Et |
| 27 | CH₂-c-Pr | i-Pr |
| 28 | CH₂-c-Pr | CH₂-c-Pr |
| 29 | CH₂-c-Pr | CH₂-c-Pen |
| 30 | CH₂-c-Pr | c-Bu |
| 31 | CH₂-c-Pr | c-Pen |
| 32 | CH₂-c-Pr | CHF₂ |
| 33 | CH₂-c-Pen | Me |
| 34 | CH₂-c-Pen | Et |
| 35 | CH₂-c-Pen | i-Pr |
| 36 | CH₂-c-Pen | CH₂-c-Pr |
| 37 | CH₂-c-Pen | CH₂-c-Pen |
| 38 | CH₂-c-Pen | c-Bu |
| 39 | CH₂-c-Pen | c-Pen |
| 40 | CH₂-c-Pen | CHF₂ |
| 41 | c-Bu | Me |
| 42 | c-Bu | Et |
| 43 | c-Bu | i-Pr |
| 44 | c-Bu | CH₂-c-Pr |
| 45 | c-Bu | CH₂-c-Pen |
| 46 | c-Bu | c-Bu |
| 47 | c-Bu | c-Pen |
| 48 | c-Bu | CHF₂ |
| 49 | c-Pen | Me |
| 50 | c-Pen | Et |
| 51 | c-Pen | i-Pr |
| 52 | c-Pen | CH₂-c-Pr |
| 53 | c-Pen | CH₂-c-Pen |
| 54 | c-Pen | c-Bu |
| 55 | c-Pen | c-Pen |
| 56 | c-Pen | CHF₂ |
| 57 | CHF₂ | Me |
| 58 | CHF₂ | Et |
| 59 | CHF₂ | i-Pr |
| 60 | CHF₂ | CH₂-c-Pr |
| 61 | CHF₂ | CH₂-c-Pen |
| 62 | CHF₂ | c-Bu |
| 63 | CHF₂ | c-Pen |
| 64 | CHF₂ | CHF₂ |

TABLE 7

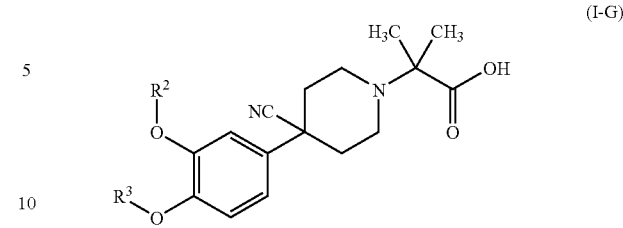

(I-G)

| No. | R² | R³ |
|---|---|---|
| 1 | Me | Me |
| 2 | Me | Et |
| 3 | Me | i-Pr |
| 4 | Me | CH₂-c-Pr |
| 5 | Me | CH₂-c-Pen |
| 6 | Me | c-Bu |
| 7 | Me | c-Pen |
| 8 | Me | CHF₂ |
| 9 | Et | Me |
| 10 | Et | Et |
| 11 | Et | i-Pr |
| 12 | Et | CH₂-c-Pr |
| 13 | Et | CH₂-c-Pen |
| 14 | Et | c-Bu |
| 15 | Et | c-Pen |
| 16 | Et | CHF₂ |
| 17 | i-Pr | Me |
| 18 | i-Pr | Et |
| 19 | i-Pr | i-Pr |
| 20 | i-Pr | CH₂-c-Pr |
| 21 | i-Pr | CH₂-c-Pen |
| 22 | i-Pr | c-Bu |
| 23 | i-Pr | c-Pen |
| 24 | i-Pr | CHF₂ |
| 25 | CH₂-c-Pr | Me |
| 26 | CH₂-c-Pr | Et |
| 27 | CH₂-c-Pr | i-Pr |
| 28 | CH₂-c-Pr | CH₂-c-Pr |
| 29 | CH₂-c-Pr | CH₂-c-Pen |
| 30 | CH₂-c-Pr | c-Bu |
| 31 | CH₂-c-Pr | c-Pen |
| 32 | CH₂-c-Pr | CHF₂ |
| 33 | CH₂-c-Pen | Me |
| 34 | CH₂-c-Pen | Et |
| 35 | CH₂-c-Pen | i-Pr |
| 36 | CH₂-c-Pen | CH₂-c-Pr |
| 37 | CH₂-c-Pen | CH₂-c-Pen |
| 38 | CH₂-c-Pen | c-Bu |
| 39 | CH₂-c-Pen | c-Pen |
| 40 | CH₂-c-Pen | CHF₂ |
| 41 | c-Bu | Me |
| 42 | c-Bu | Et |
| 43 | c-Bu | i-Pr |
| 44 | c-Bu | CH₂-c-Pr |
| 45 | c-Bu | CH₂-c-Pen |
| 46 | c-Bu | c-Bu |
| 47 | c-Bu | c-Pen |
| 48 | c-Bu | CHF₂ |
| 49 | c-Pen | Me |
| 50 | c-Pen | Et |
| 51 | c-Pen | i-Pr |
| 52 | c-Pen | CH₂-c-Pr |
| 53 | c-Pen | CH₂-c-Pen |
| 54 | c-Pen | c-Bu |
| 55 | c-Pen | c-Pen |
| 56 | c-Pen | CHF₂ |
| 57 | CHF₂ | Me |
| 58 | CHF₂ | Et |
| 59 | CHF₂ | i-Pr |
| 60 | CHF₂ | CH₂-c-Pr |
| 61 | CHF₂ | CH₂-c-Pen |
| 62 | CHF₂ | c-Bu |
| 63 | CHF₂ | c-Pen |
| 64 | CHF₂ | CHF₂ |

TABLE 8

(I-H)

| No. | R² | R³ |
|---|---|---|
| 1 | Me | Me |
| 2 | Me | Et |
| 3 | Me | i-Pr |
| 4 | Me | CH₂-c-Pr |
| 5 | Me | CH₂-c-Pen |
| 6 | Me | c-Bu |
| 7 | Me | c-Pen |
| 8 | Me | CHF₂ |
| 9 | Et | Me |
| 10 | Et | Et |
| 11 | Et | i-Pr |
| 12 | Et | CH₂-c-Pr |
| 13 | Et | CH₂-c-Pen |
| 14 | Et | c-Bu |
| 15 | Et | c-Pen |
| 16 | Et | CHF₂ |
| 17 | i-Pr | Me |
| 18 | i-Pr | Et |
| 19 | i-Pr | i-Pr |
| 20 | i-Pr | CH₂-c-Pr |
| 21 | i-Pr | CH₂-c-Pen |
| 22 | i-Pr | c-Bu |
| 23 | i-Pr | c-Pen |
| 24 | i-Pr | CHF₂ |
| 25 | CH₂-c-Pr | Me |
| 26 | CH₂-c-Pr | Et |
| 27 | CH₂-c-Pr | i-Pr |
| 28 | CH₂-c-Pr | CH₂-c-Pr |
| 29 | CH₂-c-Pr | CH₂-c-Pen |
| 30 | CH₂-c-Pr | c-Bu |
| 31 | CH₂-c-Pr | c-Pen |
| 32 | CH₂-c-Pr | CHF₂ |
| 33 | CH₂-c-Pen | Me |
| 34 | CH₂-c-Pen | Et |
| 35 | CH₂-c-Pen | i-Pr |
| 36 | CH₂-c-Pen | CH₂-c-Pr |
| 37 | CH₂-c-Pen | CH₂-c-Pen |
| 38 | CH₂-c-Pen | c-Bu |
| 39 | CH₂-c-Pen | c-Pen |
| 40 | CH₂-c-Pen | CHF₂ |
| 41 | c-Bu | Me |
| 42 | c-Bu | Et |
| 43 | c-Bu | i-Pr |
| 44 | c-Bu | CH₂-c-Pr |
| 45 | c-Bu | CH₂-c-Pen |
| 46 | c-Bu | c-Bu |
| 47 | c-Bu | c-Pen |
| 48 | c-Bu | CHF₂ |
| 49 | c-Pen | Me |
| 50 | c-Pen | Et |
| 51 | c-Pen | i-Pr |
| 52 | c-Pen | CH₂-c-Pr |
| 53 | c-Pen | CH₂-c-Pen |
| 54 | c-Pen | c-Bu |
| 55 | c-Pen | c-Pen |
| 56 | c-Pen | CHF₂ |
| 57 | CHF₂ | Me |
| 58 | CHF₂ | Et |
| 59 | CHF₂ | i-Pr |
| 60 | CHF₂ | CH₂-c-Pr |
| 61 | CHF₂ | CH₂-c-Pen |
| 62 | CHF₂ | c-Bu |
| 63 | CHF₂ | c-Pen |
| 64 | CHF₂ | CHF₂ |

TABLE 9

(I-J)

| No. | R² | R³ |
|---|---|---|
| 1 | Me | Me |
| 2 | Me | Et |
| 3 | Me | i-Pr |
| 4 | Me | CH₂-c-Pr |
| 5 | Me | CH₂-c-Pen |
| 6 | Me | c-Bu |
| 7 | Me | c-Pen |
| 8 | Me | CHF₂ |
| 9 | Et | Me |
| 10 | Et | Et |
| 11 | Et | i-Pr |
| 12 | Et | CH₂-c-Pr |
| 13 | Et | CH₂-c-Pen |
| 14 | Et | c-Bu |
| 15 | Et | c-Pen |
| 16 | Et | CHF₂ |
| 17 | i-Pr | Me |
| 18 | i-Pr | Et |
| 19 | i-Pr | i-Pr |
| 20 | i-Pr | CH₂-c-Pr |
| 21 | i-Pr | CH₂-c-Pen |
| 22 | i-Pr | c-Bu |
| 23 | i-Pr | c-Pen |
| 24 | i-Pr | CHF₂ |
| 25 | CH₂-c-Pr | Me |
| 26 | CH₂-c-Pr | Et |
| 27 | CH₂-c-Pr | i-Pr |
| 28 | CH₂-c-Pr | CH₂-c-Pr |
| 29 | CH₂-c-Pr | CH₂-c-Pen |
| 30 | CH₂-c-Pr | c-Bu |
| 31 | CH₂-c-Pr | c-Pen |
| 32 | CH₂-c-Pr | CHF₂ |
| 33 | CH₂-c-Pen | Me |
| 34 | CH₂-c-Pen | Et |
| 35 | CH₂-c-Pen | i-Pr |
| 36 | CH₂-c-Pen | CH₂-c-Pr |
| 37 | CH₂-c-Pen | CH₂-c-Pen |
| 38 | CH₂-c-Pen | c-Bu |
| 39 | CH₂-c-Pen | c-Pen |
| 40 | CH₂-c-Pen | CHF₂ |
| 41 | c-Bu | Me |
| 42 | c-Bu | Et |
| 43 | c-Bu | i-Pr |
| 44 | c-Bu | CH₂-c-Pr |
| 45 | c-Bu | CH₂-c-Pen |
| 46 | c-Bu | c-Bu |
| 47 | c-Bu | c-Pen |
| 48 | c-Bu | CHF₂ |
| 49 | c-Pen | Me |
| 50 | c-Pen | Et |
| 51 | c-Pen | i-Pr |
| 52 | c-Pen | CH₂-c-Pr |
| 53 | c-Pen | CH₂-c-Pen |
| 54 | c-Pen | c-Bu |
| 55 | c-Pen | c-Pen |
| 56 | c-Pen | CHF₂ |
| 57 | CHF₂ | Me |
| 58 | CHF₂ | Et |
| 59 | CHF₂ | i-Pr |
| 60 | CHF₂ | CH₂-c-Pr |
| 61 | CHF₂ | CH₂-c-Pen |
| 62 | CHF₂ | c-Bu |
| 63 | CHF₂ | c-Pen |
| 64 | CHF₂ | CHF₂ |

TABLE 10

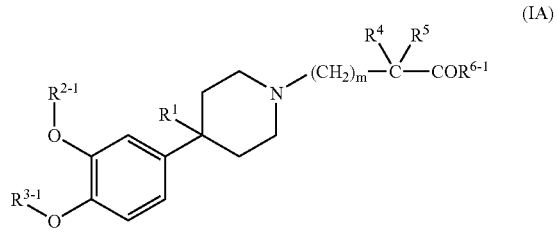

(I-K)

| No. | R² | R³ |
|---|---|---|
| 1 | Me | Me |
| 2 | Me | Et |
| 3 | Me | i-Pr |
| 4 | Me | CH₂-c-Pr |
| 5 | Me | CH₂-c-Pen |
| 6 | Me | c-Bu |
| 7 | Me | c-Pen |
| 8 | Me | CHF₂ |
| 9 | Et | Me |
| 10 | Et | Et |
| 11 | Et | i-Pr |
| 12 | Et | CH₂-c-Pr |
| 13 | Et | CH₂-c-Pen |
| 14 | Et | c-Bu |
| 15 | Et | c-Pen |
| 16 | Et | CHF₂ |
| 17 | i-Pr | Me |
| 18 | i-Pr | Et |
| 19 | i-Pr | i-Pr |
| 20 | i-Pr | CH₂-c-Pr |
| 21 | i-Pr | CH₂-c-Pen |
| 22 | i-Pr | c-Bu |
| 23 | i-Pr | c-Pen |
| 24 | i-Pr | CHF₂ |
| 25 | CH₂-c-Pr | Me |
| 26 | CH₂-c-Pr | Et |
| 27 | CH₂-c-Pr | i-Pr |
| 28 | CH₂-c-Pr | CH₂-c-Pr |
| 29 | CH₂-c-Pr | CH₂-c-Pen |
| 30 | CH₂-c-Pr | c-Bu |
| 31 | CH₂-c-Pr | c-Pen |
| 32 | CH₂-c-Pr | CHF₂ |
| 33 | CH₂-c-Pen | Me |
| 34 | CH₂-c-Pen | Et |
| 35 | CH₂-c-Pen | i-Pr |
| 36 | CH₂-c-Pen | CH₂-c-Pr |
| 37 | CH₂-c-Pen | CH₂-c-Pen |
| 38 | CH₂-c-Pen | c-Bu |
| 39 | CH₂-c-Pen | c-Pen |
| 40 | CH₂-c-Pen | CHF₂ |
| 41 | c-Bu | Me |
| 42 | c-Bu | Et |
| 43 | c-Bu | i-Pr |
| 44 | c-Bu | CH₂-c-Pr |
| 45 | c-Bu | CH₂-c-Pen |
| 46 | c-Bu | c-Bu |
| 47 | c-Bu | c-Pen |
| 48 | c-Bu | CHF₂ |
| 49 | c-Pen | Me |
| 50 | c-Pen | Et |
| 51 | c-Pen | i-Pr |
| 52 | c-Pen | CH₂-c-Pr |
| 53 | c-Pen | CH₂-c-Pen |
| 54 | c-Pen | c-Bu |
| 55 | c-Pen | c-Pen |
| 56 | c-Pen | CHF₂ |
| 57 | CHF₂ | Me |
| 58 | CHF₂ | Et |
| 59 | CHF₂ | i-Pr |
| 60 | CHF₂ | CH₂-c-Pr |
| 61 | CHF₂ | CH₂-c-Pen |
| 62 | CHF₂ | c-Bu |
| 63 | CHF₂ | c-Pen |
| 64 | CHF₂ | CHF₂ |

[Process for Producing the Compound of the Present Invention]

The compound of the present invention represented by formula (I) can be prepared by the following methods or methods described in Examples.

[1] Among the compounds of the present invention represented by formula (1), a compound in which $R^6$ represents a C1–8 alkoxy group or a C1–8 alkyl group substituted with a phenyl group; and $-OR^2$ and $-OR^3$ do not represent a hydroxyl group, i.e., a compound represented by formula (IA):

(IA)

(wherein $R^{6-1}$ represents a C1–8 alkoxy group or a C1–8 alkyl group substituted with a phenyl group; $-OR^{2-1}$ and $-OR^{3-1}$ have the same meanings as $-OR^2$ and $-OR^3$, with the proviso that they do not represent a hydroxyl group; and other symbols have the same meanings as described above) can be prepared by the following methods a) to c).

a) The compound represented by formula (IA) can be prepared by reacting a compound represented by formula (II-1):

(II-1)

(wherein all symbols have the same meanings as described above) with a compound represented by formula (III-1):

(III-1)

(wherein $R^7$ represents a leaving group (e.g., a halogen atom, a trifluoromethylsulfonyloxy group, a mesyloxy group or a tosyloxy group), and other symbols have the same meanings as described above).

Reaction of the compound represented by formula (II-1) with the compound represented by formula (III-1) is known. For example, it is carried out at 0 to 100° C. in an inert organic solvent (e.g., dimethylformamide, dimethyl sulfoxide, chloroform, methylene chloride, diethyl ether, tetrahydrofuran, acetonitrile, etc.) in the presence of a base (e.g., potassium carbonate, calcium carbonate, sodium carbonate, cesium carbonate, triethylamine, pyridine, 2,6-lutidine, etc.).

b) The compound represented by formula (IA) can be prepared by reacting a compound represented by formula (II-2):

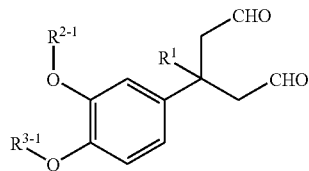

(II-2)

(wherein all symbols have the same meanings as described above) with a compound represented by formula (III-2):

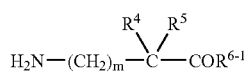

(III-2)

(wherein all symbols have the same meanings as described above).

Reaction of the compound represented by formula (II-2) with the compound represented by formula (III-2) is known. For example, it is carried out in a mixed solvent of an inert organic solvent (e.g., dimethylformamide, dimethyl sulfoxide, chloroform, methylene chloride, dichloroethane, diethyl ether, tetrahydrofuran, acetonitrile, etc.) with acetic acid in the presence of a reducing agent (e.g., sodium triacetoxyboron hydride ($NaBH(OAc)_3$), sodium cyanoboron hydride ($NaBH_3CN$), etc.) at 0 to 100° C.

c) Also, among the compounds represented by formula (IA), a compound in which m is 1 and $R^4$ and $R^5$ each represents a hydrogen atom, i.e., a compound represented by formula (IA-1):

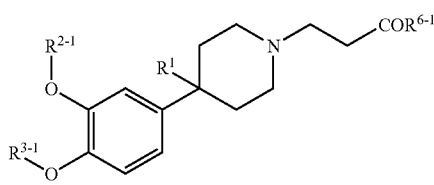

(IA-1)

(wherein all symbols have the same meanings as described above) can be prepared by reacting the compound represented by formula (II-1) with a compound represented by formula (IV):

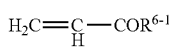

(IV)

(wherein all symbols have the same meanings as described above).

Reaction of the compound represented by formula (II-1) with the compound represented by formula (IV) is known. For example, it is carried out in an inert organic solvent (e.g., dimethylformamide, dimethyl sulfoxide, chloroform, methylene chloride, diethyl ether, tetrahydrofuran, acetonitrile, etc.) in the presence of a base (e.g., potassium carbonate, calcium carbonate, sodium carbonate, cesium carbonate, triethylamine, pyridine, 2,6-lutidine, etc.) at 0 to 100° C.

[2] Among the compounds of the present invention represented by formula (I), a compound in which at least one of —$COR^6$, —$OR^2$ and —$OR^3$ represents a carboxyl group or a hydroxyl group, i.e., a compound represented by formula (IB):

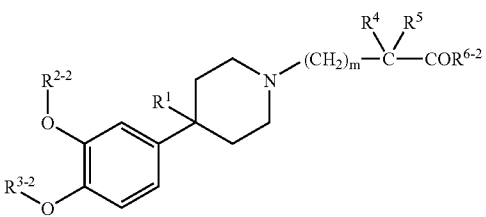

(IB)

(wherein —$COR^{6-2}$, —$OR^{2-2}$ and —$OR^{3-2}$ have the same meanings as —$COR^6$, —$OR^2$ and —$OR^3$, with the proviso that at least one of them represents a carboxyl group or a hydroxyl group; and other symbols have the same meanings as described above) can be prepared by subjecting a compound among the compounds of formula (IA) prepared by the above methods in which —$COR^{6-1}$, —$OR^{2-1}$ or —$OR^{3-1}$ represents a carboxyl group or a hydroxyl group protected with a protecting group, i.e., a compound represented by formula (IA-2):

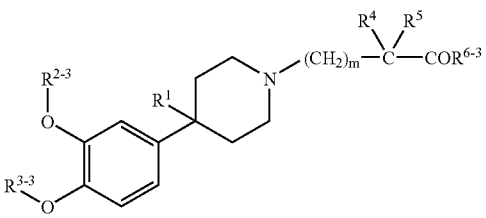

(IA-2)

(wherein —$COR^{6-3}$, —$OR^{2-3}$ and —$OR^{3-3}$ have the same meanings as —$COR^6$, —$OR^2$ and —$OR^3$, with the proviso that at least one of them represents a carboxyl group or a hydroxyl group protected with a protecting group; and other symbols have the same meanings as described above) to a deprotection reaction of the protecting group.

Examples of the protecting group of a carboxyl group include a methyl group, an ethyl group, a t-butyl group, and a benzyl group.

Examples of the protecting group of a hydroxyl group include a methoxymethyl group, a 2-tetrahydropyranyl group, a t-butyldimethylsilyl group, a t-butyldiphenylsilyl group, an acetyl group, and a benzyl group.

The protecting groups of a carboxyl group and a hydroxyl group are not particularly limited to the above, and other groups can also be used, so long as they can be easily and selectively released. For example, those which are described by T. W. Greene in *Protective Groups in Organic Synthesis*, 3rd edition, Wiley, N.Y., 1999, can be used.

The deprotection reaction of these protecting groups of a carboxyl group and a hydroxyl group is known, and examples include (1) a deprotection reaction under alkaline conditions,
(2) a deprotection reaction under acidic conditions,
(3) a deprotection reaction by hydrolysis,
(4) a deprotection reaction of a silyl group, and the like.

These methods are specifically described below.

(1) The deprotection reaction under alkaline conditions is carried out, for example, in an organic solvent (e.g., methanol, tetrahydrofuran, dioxane, dimethylformamide, etc.) using an alkali metal hydroxide (e.g., sodium hydroxide, potassium hydroxide, lithium hydroxide, etc.), an alkaline earth metal hydroxide (e.g., barium hydroxide, calcium hydroxide, etc.) or a carbonate (e.g., sodium carbonate, potassium carbonate, etc.), an organic amine (e.g., triethylamine, diisopropylethylamine, piperazine, etc.) or a quaternary ammonium salt (e.g., tetrabutylammonium fluoride, etc.) or an aqueous solution thereof or a mixture thereof at a temperature of 0 to 40° C.

(2) The deprotection reaction under acidic conditions is carried out, for example, in an organic solvent (e.g., methylene chloride, chloroform, dioxane, ethyl acetate, anisole, etc.) using an organic acid (e.g., acetic acid, trifluoroacetic acid, methanesulfonic acid, etc.), an inorganic acid (e.g., hydrochloric acid, sulfuric acid, etc.) or a mixture thereof (e.g., hydrogen bromide/acetic acid, etc.) at a temperature of 0 to 100° C.

(3) The deprotection reaction by hydrolysis is carried out, for example, in a solvent, such as an ether system (e.g., tetrahydrofuran, dioxane, dimethoxyethane, diethyl ether, etc.), an alcohol system (e.g., methanol or ethanol), a benzene system (e.g., benzene, toluene, etc.), a ketone system (e.g., acetone, methyl ethyl ketone, etc.), a nitrile system (e.g., acetonitrile, etc.), an amide system (e.g., dimethylformamide, etc.), water, ethyl acetate, acetic acid or a mixed solvent of two or more of them, in the presence of a catalyst (e.g., palladium-carbon, palladium black, palladium hydroxide, platinum oxide, Raney nickel, etc.) under ordinary or forced pressure in an atmosphere of hydrogen or in the presence of ammonium formate at a temperature of 0 to 200° C.

(4) The deprotection reaction of a silyl group is carried out, for example, in an organic solvent miscible with water (e.g., tetrahydrofuran, acetonitrile, etc.) using tetrabutylammonium fluoride at a temperature of 0 to 40° C.

Although it can be easily understood by those skilled in the art, an objective compound of the present invention can be easily prepared by properly using these deprotection reactions.

[3] Among the compounds of the present invention represented by formula (I), a compound in which $R^6$ represents —NHOH; and —$OR^2$ and —$OR^3$ do not represent a hydroxyl group, i.e., a compound represented by formula (IC):

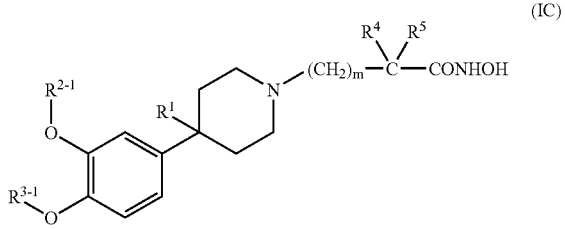

(wherein all symbols have the same meanings as described above) can be prepared by subjecting a compound represented by formula (V):

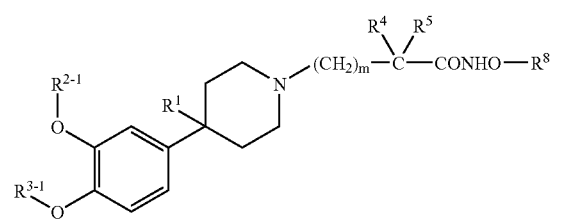

(wherein $R^8$ represents a protecting group of hydroxamic acid; and other symbols have the same meanings as described above) to a deprotection reaction.

The protecting group of hydroxamic acid includes a t-butyl group, —$C(CH_3)_2$—$OCH_3$, a benzyl group, a t-butyldimethylsilyl group and a tetrahydropyran-1-yl group, but other groups can also be used without particular limitation so long as they can be easily and selectively released. For example, those described by T. W. Greene in *Protective Groups in Organic Synthesis*, 3rd edition, Wiley, N.Y., 1999, can be used.

Deprotection reactions of these protecting groups of hydroxamic acid is known, and examples include (1) a deprotection reaction under alkaline conditions,
(2) a deprotection reaction under acidic conditions,
(3) a deprotection reaction by hydrolysis,
(4) a deprotection reaction of silyl group, and the like.

These reactions can be carried out by the same methods described above.

[4] Among the compounds of the present invention represented by formula (I), a compound in which $R^6$ represents —NHOH; and at least one of —$OR^2$ and —$OR^3$ represents a hydroxyl group, i.e., a compound represented by formula (ID):

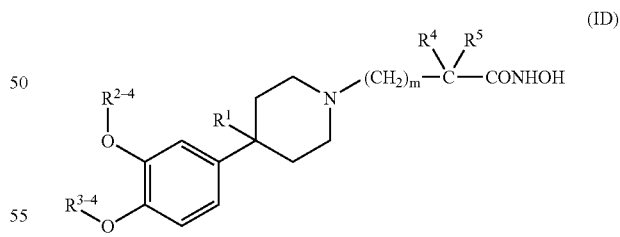

(wherein —$OR^{2-4}$ and —$OR^{3-4}$ have the same meanings as —$OR^2$ and —$OR^3$, with the proviso that at least one group thereof represents a hydroxyl group; and other symbols have the same meanings as described above) can be prepared by subjecting, among the compounds of formula (IC) prepared by the method described above, a compound in which —$OR^{2-1}$ or —$OR^{3-1}$ represents a hydroxyl group protected with a protecting group, i.e., a compound represented by formula (IC-1):

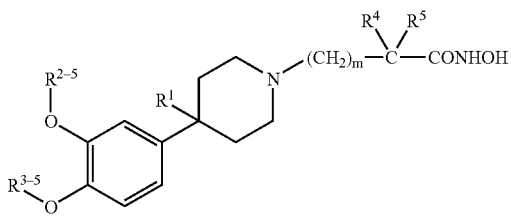

(IC-1)

(wherein —OR$^{2-5}$ and —OR$^{3-5}$ have the same meanings as —OR$^2$ and —OR$^3$, with the proviso that at least one of them represents a hydroxyl group protected with a protecting group; and other symbols have the same meanings as described above) to a deprotection reaction of the protecting group.

The deprotection reaction of a protecting group can be carried out by the methods described above.

The compounds represented by formulae (II-1), (II-2), (III-1), (III-2), (IV) and (V) are known compounds or can be prepared easily by known methods.

For example, the compounds represented by formulae (II-1), (II-2) and (V) can be prepared by the methods shown by the following Reaction Schemes 1 to 3.

In the reaction schemes, Me represents a methyl group; Et represents an ethyl group; Boc represents a t-butoxycarbonyl group; Ms represents a mesyl group; LiHMDS represents lithium hexamethyldisilazane; TFA represents trifluoroacetic acid; and other symbols have the same meanings as described above.

Reaction Scheme 1

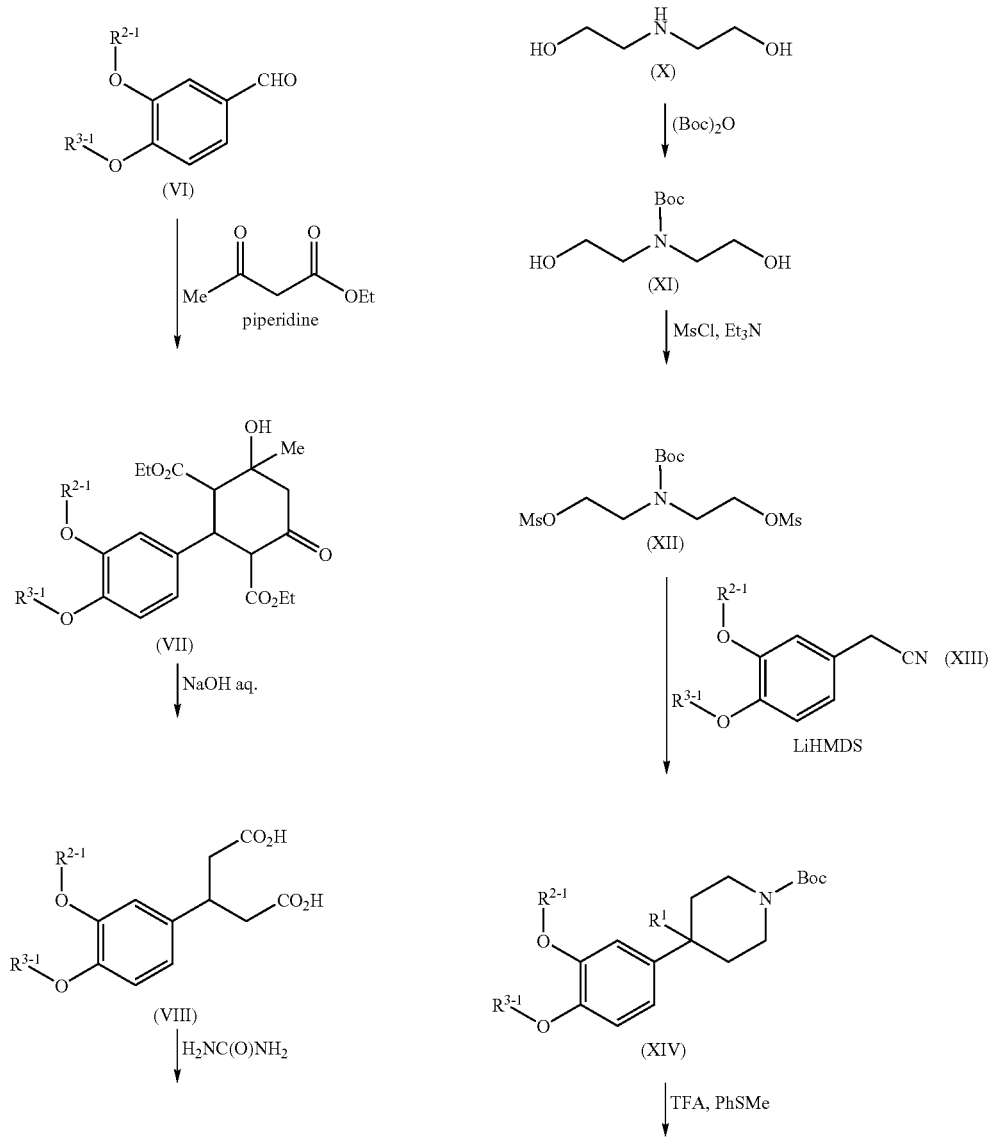

-continued
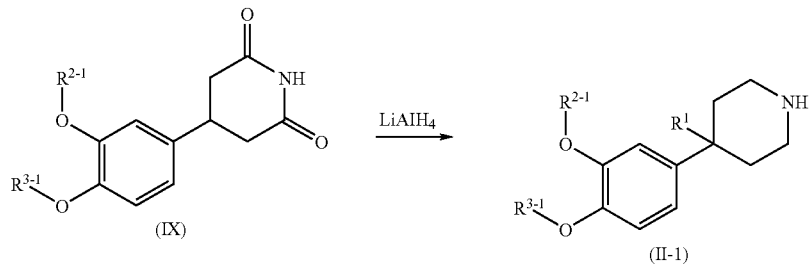
Reaction Scheme 2
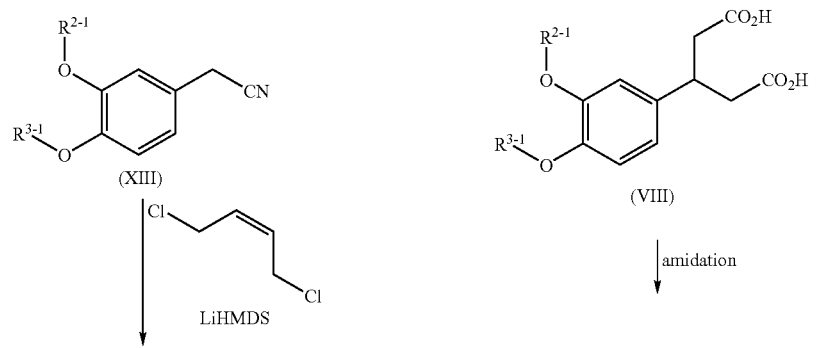
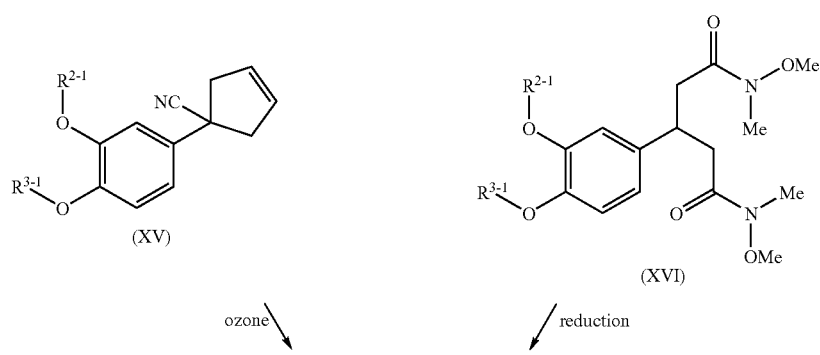
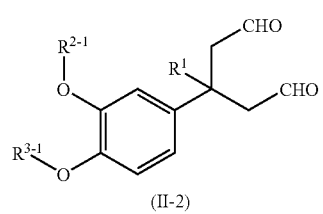

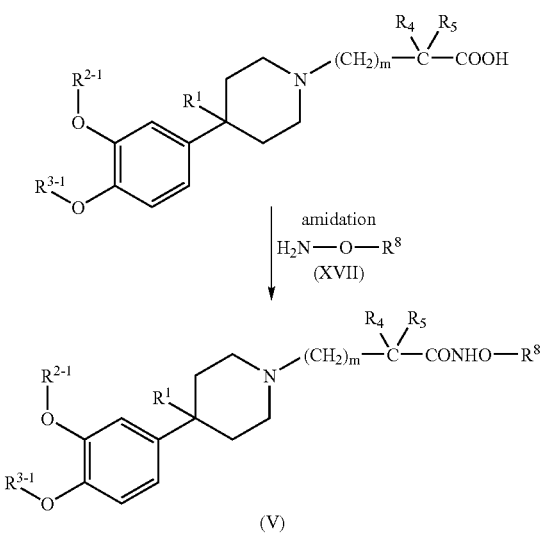

In Reaction Schemes 1 and 3, the compounds to be used as the starting materials represented by formulae (VI), (X), (XIII) and (XVII) are known compounds or can be prepared easily by known methods.

In each reaction described herein, the reaction product can be purified by general purification techniques such as distillation under ordinary pressure or a reduced pressure, high performance liquid chromatography, thin layer chromatography or column chromatography using silica gel or magnesium silicate, washing and recrystallization. Purification may be carried out in each reaction or after completion of several reactions.

[Pharmacological Effects]

The PDE4 inhibitory activity of the compounds of the present invention represented by formula (I) was confirmed by the following tests.

In Vitro Enzyme Assay:

Test Methods:

U937 cells (originated from human monocyte) were cultured in PRMI 1640 medium containing 10% fetal bovine serum. The U937 cells were harvested and homogenized in 20 mM Tris-HCl buffer [pH 8.0, containing PMSF (1 mM), leupeptin (1 μg/ml) and pepstatin A (1 μg/ml)]. After centrifugation (at 15,000 rpm for 10 minutes), the supernatant was recovered and filtered through a 0.45 μm filter. The sample was applied to MonoQ (manufactured by Pharmacia, strong anion exchange resin) column and eluted by a density gradient of 0 to 0.8 M NaCl. Fractions from which the PDE activity was disappeared by 10 μM rolipram (a PDE4-selective inhibitor) were recovered and used as the enzyme solution for the measurement of PDE4 inhibitory activity.

The enzyme activity was measured by the following method. 80 μl of a diluted enzyme solution (in phosphate buffer (pH 7.4) containing 0.1 mg/kg bovine serum albumin), 10 μl of a solution of the compound of the present invention (in 10% DMSO) and 10 μl of $^3$H-cAMP (20,000 cpm, 10 μM) [in an imidazole buffer (100 mM, pH 7.5) containing $MgSO_4$ (100 mM) and bovine serum albumin (1 mg/ml)] were mixed and incubated at room temperature for 30 minutes. The reaction was stopped by treating the reaction solution for 2.5 minutes in a microwave oven. After centrifugation (at 2,000 rpm for 1 minute), 10 μl of snake venom (1 mg/ml, manufactured by Sigma, trade name V7000) was added and incubated at room temperature for 30 minutes. To an alumina column (100 μl), 50 μl of the supernatant was applied, eluted with 80 μl of 0.005 N hydrochloric acid, and radioactivity of the eluate was measured.

PDE4 inhibitory activity ratio of the compound of the present invention was calculated by the following equation:

PDE4 inhibitory activity ratio (%) =

(1 − radioactivity in the presence of the compound of the present invention/radioactivity in the absence of the compound of the present invention) × 100

The $IC_{50}$ value was calculated on each compound as a concentration of the compound of the present invention which inhibits 50% of the PDE4 activity.

The test results are shown in Table 11.

TABLE 11

| Ex No. | $IC_{50}$ (nM) |
|---|---|
| 3 | 0.03 |

TNF-α Production Inhibitory Activity:

A heparinized blood sample collected from a healthy person was dispensed in 180 μl/well into a 96-well plate. A solution of the compound of the present invention (final concentration of DMSO: 0.1% or less) was dispensed at 10 μl and the plate was allowed to stand at 37° C. for 30 minutes in a 5% $CO_2$ incubator. The reaction was initiated by adding 10 μl of LPS solution. After 6 hours of incubation in a $CO_2$ incubator (5% $CO_2$, humidified), the plate was shaken and then centrifuged at 300×g for 5 minutes to recover 50 μl of the supernatant (blood plasma). The amount of TNF-α in the supernatant was measured using a human TNF-α ELISA kit (DIACLONE Cat. No. 850.090.096) in accordance with the method attached thereto. As a result, the compound of the present invention showed a dose-dependent inhibitory activity.

[Toxicity]

The toxicity of the compound represented by formula (I) of the present invention is very low so that it is considered that the compound is sufficiently safe for using as a pharmaceutical.

INDUSTRIAL APPLICABILITY

[Application to Pharmaceutical]

Since the compound of the present invention has PDE4 inhibition activity, it is considered that it is useful in preventing and/or treating various diseases such as inflammatory diseases (e.g., asthma, obstructive lung disease, sepsis, sarcoidosis, nephritis, hepatitis, enteritis, etc.), diabetic diseases, allergic diseases (e.g., allergic rhinitis, allergic conjunctivitis, seasonal conjunctivitis, atopic dermatitis, etc.), autoimmune diseases (e.g., ulcerative colitis, Crohn's disease, rheumatism, psoriasis, multiple sclerosis, collagen disease, etc.), osteoporosis, bone fracture, obesity, depression, Parkinson's disease, dementia, ischemia-reperfusion injury, leukemia and AIDS.

The compound represented by formula (I) of the present invention, a nontoxic salt thereof or a hydrate thereof is generally administered systemically or topically and orally or parenterally when it is used for the above objects.

The dosages are determined depending on age, body weight, symptom, therapeutic effect, administration route, duration of the treatment and the like. Generally, 1 mg to 1000 mg per adult is orally administered once to several times per day, or 1 mg to 100 mg per adult is parenterally administered (preferably by intravenous administration) once to several times per day, or continuously administered from vein for 1 to 24 hours per day.

Since the dose changes depending on various conditions as described above, there are cases in which doses lower than or greater than the above ranges may be used.

The compound represented by formula (I) of the present invention may be administered in the form of solid compositions, liquid compositions and other compositions for oral administration, and injections, liniments, suppositories, eye lotions, inhalants and the like for parenteral administration.

Solid compositions for oral administration include tablets, pills, capsules, dispersible powders, granules and the like.

Capsules include hard capsules and soft capsules.

In such solid compositions, one or more active compound (s) are mixed with at least one inert diluent such as lactose, mannitol, glucose, hydroxypropyl cellulose, microcrystalline cellulose, starch, polyvinyl pyrrolidone or magnesium metasilicate aluminate. The composition may also contain additional substances other than the inert diluent, e.g., lubricants such as magnesium stearate, disintegrating agents such as cellulose calcium glycolate, stabilizing agents such as lactose, and assisting agents for dissolving such as glutamic acid and asparatic acid according to usual methods. If necessary, the tablets or pills may be coated with film of gastric- or enteric-coating agents such as sugar, gelatin, hydroxypropyl cellulose and hydroxypropyl cellulose phthalate, or be coated with two or more films. Furthermore, capsules of absorbable materials such as gelatin are included.

Liquid compositions for oral administration include pharmaceutically acceptable emulsions, solutions, syrups, elixirs and the like. In such liquid compositions, one or more active compound(s) are contained in an inert diluent commonly used (e.g., purified water, ethanol). Furthermore, such compositions may also contain auxiliary material such as wetting agents or suspending agents, sweetening agents, flavoring agents, flavoring agents, and preserving agents.

Other compositions for oral administration include sprays containing one or more active compound(s) which are prepared by known methods. Such compositions may contain stabilizing agents such as sodium hydrogen sulfate, buffering agents to give isotonicity, isotonic solutions such as sodium chloride, sodium citrate or citric acid, in addition to inert diluents. The process for preparing sprays are described in U.S. Pat. Nos. 2,868,691 and 3,095,355.

Injections for parenteral administration in the present invention include sterile aqueous or non-aqueous solutions, suspensions and emulsions. Aqueous solutions and suspensions include distilled water for injection and physiological saline. Non-aqueous solutions and suspensions include propylene glycol, polyethylene glycol, plant oil such as olive oil, alcohols such as ethanol, POLYSORBATE80 (registered trade mark), and the like. Sterile aqueous and non-aqueous solutions, suspensions and emulsions may be used as a mixture. Such compositions may further contain preserving agents, wetting agents, emulsifying agents, dispersing agents, stabilizing agents (e.g., lactose), auxiliary agents such as solubilizing auxiliary agents (e.g., glutamic acid, aspartic acid). They may be sterilized by filtration through a bacteria-retaining filter, incorporation of a sterilizing agent or irradiation. For example, they may also be manufactured in the form of sterile solid compositions which can be dissolved in sterile water or other sterile diluent for injection before use of the freeze-dried product.

The dosage form of instillations for parenteral administration include eye lotions, suspending eye lotions, emulsion eye lotions, eye lotions dissolved when used, and eye ointments.

These instillations are manufactured according to known methods. For example, the eye lotions can be prepared, if necessary, by appropriately selecting isotonizing agents (e.g., sodium chloride, concentrated glycerine, etc.), buffering agents (e.g., sodium phosphate, sodium acetate, etc.), surfactants (e.g., POLYSORBATE80 (product name), polyoxyl 40 stearate, polyoxyethylene hydrogenated castor oil, etc.), solubilizing agents (sodium citrate, sodium edetate, etc.), preserving agents (e.g., benzalkonium chloride, paraben, etc.), and the like. They are sterilized in the final step or prepared by aseptic manipulation.

The inhalants for parenteral administration include aerosols, powders for inhalation, and liquids for inhalation, and the liquid for inhalation may be in the form which is dissolved or suspended in water or an appropriate medium when used.

These inhalations can be produced according to known methods.

For example, the liquids for inhalation can be prepared, if necessary, by appropriately selecting preserving agents (e.g., benzalkonium chloride, paraben, etc.), coloring agents, buffering agents (e.g., sodium phosphate, sodium acetate, etc.), isotonizing agents (e.g., sodium chloride, concentrated glycerine, etc.), thickeners (e.g., carboxyvinyl polymer, etc.), absorbefacients, and the like.

The powders for inhalation can be prepared, if necessary, by appropriately selecting lubricants (e.g., stearic acid, salts thereof, etc.), binding agents (e.g., starch, dextrin, etc.), excipients (e.g., lactose, cellulose, etc.), coloring agents, preserving agents (e.g., benzalkonium chloride, paraben, etc.), absorbefacients, and the like.

When the liquids for inhalation are administered, a sprayer (e.g., atomizer, nebulizer) is usually used. When the powders for inhalation are used, an inhalation administration apparatus for powder agents is usually used.

Other compositions for parenteral administration include liquids for external use, endemic liniments, ointments, suppositories for intrarectal administration, pessaries for intravaginal administration and the like containing one or more active compound(s) which can be prepared by known methods.

BEST MODE FOR CARRYING OUT THE INVENTION

The present invention is explained below in detail based on Reference Examples and Examples; however, the present invention is not limited thereto.

The solvents in the parentheses show the developing or eluting solvents and the ratios of the solvents used are by volume in chromatographic separations or TLC. The solvents in the parentheses in NMR show the solvents for measurement.

REFERENCE EXAMPLE 1

(t-butoxy)-N,N-bis(2-hydroxyethyl)carboxamide

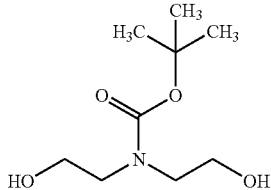

To a methylene chloride (200 ml) solution of bis(2-hydroxyethyl)amine (20.0 g), a methylene chloride (50 ml) solution of di-t-butyldicarbonate (45.6 g) was added dropwise at 0° C., followed by stirring at 0° C. for 1.5 hours. The reaction mixture was concentrated under reduced pressure. The residue was purified by silica gel column chromatography (hexane:ethyl acetate=2:1→1:2→ethyl acetate alone) to thereby obtain the title compound (41.0 g) having the following physical properties.

TLC: Rf 0.56 (chloroform:methanol=10:1);

NMR (CDCl$_3$): δ 3.80 (s, 4H), 3.43 (s, 4H), 3.60–3.00 (br, 2H), 1.47 (s, 9H).

REFERENCE EXAMPLE 2

(t-butoxy)-N,N-bis(2-(methylsulfonyloxy)ethyl)carboxamide

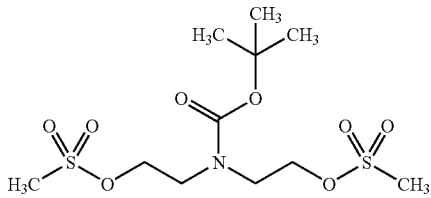

To a methylene chloride (80 ml) of the compound (7.85) prepared in Reference Example 1, triethylamine (16.0 ml) and mesyl chloride (8.89 ml) were added dropwise at −78° C. The reaction mixture was stirred at −78° C. for 10 minutes, and water was added thereto, followed by heating up to room temperature. The reaction mixture was extracted with ethyl acetate (twice). The extract was washed with saturated saline. The extract was dried over anhydrous sodium sulfate and concentrated under reduced pressure to thereby obtain the title compound (13.2 g) having the following physical properties.

TLC: Rf 0.64 (ethyl acetate);

NMR (CDCl$_3$): δ 4.40–4.25 (m, 4H), 3.62 (br.t, J=5.4 Hz, 4H), 3.04 (s, 6H), 1.48 (s, 9H).

REFERENCE EXAMPLE 3

4-(3-cyclopentyloxy-4-methoxyphenyl)-4-cyanopiperidin-1-ylcarboxylic acid.t-butyl ester

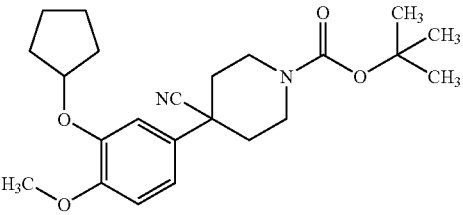

To an anhydrous tetrahydrofuran (30 ml) solution of 2-(3-cyclopenthyloxy-4-methoxyphenyl)ethane nitrile (2.50 g), 1.0 M lithium hexamethyidisilazane (LiHMDS; 24.0 ml in THF) was added dropwise at −78° C., followed by stirring at −78° C. for 20 minutes. To the reaction mixture, a tetrahydrofuran (10 ml) solution of the compound (2.17 g) prepared in Reference Example 2 was added dropwise, followed by heating up to room temperature and stirring for 2 hours. The reaction mixture was diluted with iced water and saturated saline, and extracted with ethyl acetate. The extract was washed with saturated saline, dried over anhydrous magnesium sulfate, and concentrated under reduced pressure. The residue was purified by silica gel column chromatography (hexane:diethyl ether=2:1→1:2→diethyl ether alone) to thereby obtain the title compound (1.78 g) having the following physical properties.

TLC: Rf 0.56 (hexane:ethyl acetate=2:1).

REFERENCE EXAMPLE 4

4-(3-cyclopentyloxy-4-methoxyphenyl)-4-cyanopiperidine.hydrochloride

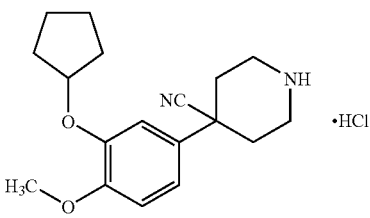

To a methylene chloride (10 ml) solution of the compound (1.68 g) prepared in Reference Example 3, methylthiobenzene (5 ml) and trifluoroacetic acid (5 ml) were added at room temperature, followed by stirring at room temperature for 1.5 hours. The reaction mixture was diluted with water, and extracted with methylene chloride (twice). The extract was dried over anhydrous sodium sulfate, and concentrated under reduced pressure. To the residue, a 4 N hydrogen chloride-ethyl acetate solution (1 ml) was added, and the mixture was concentrated under reduced pressure. To the residue, ethyl acetate was added, and the precipitated solid was filtered to thereby obtain the title compound (510 mg) having the following physical properties.

TLC: Rf 0.33 (chloroform:methanol=10:1);

NMR (CDCl$_3$): δ 10.02 (br.s, 2H), 7.10–7.00 (m, 2H), 6.88 (d, J=9.0 Hz, 1H), 4.82 (m, 1H), 3.86 (s, 3H), 3.80–3.60 (m, 2H), 3.50–3.30 (m, 2H), 2.80–2.60 (m, 2H), 2.40–2.20 (m, 2H), 2.10–1.80 (m, 6H), 1.80–1.60 (m, 2H).

EXAMPLE 1

2-(4-(3-cyclopentyloxy-4-methoxyphenyl)-4-cyanopiperidin-1-yl)acetic acid.ethyl ester

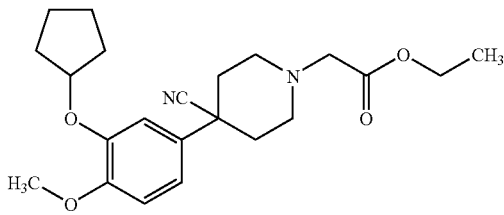

A mixture of the compound (300 mg) prepared in Reference Example 4, potassium carbonate (246 mg), dimethylformamide (4 ml) and 2-bromoacetic acid.ethyl ester (0.15 ml) was stirred at room temperature for 20 hours. The reaction mixture was diluted with ethyl acetate, washed with water and saturated saline in this order, dried over anhydrous sodium sulfate, and concentrated under reduced pressure. The residue was purified by silica gel column chromatography (hexane:ethyl acetate=2:1→1:1→ethyl acetate alone) to thereby obtain the title compound (341 mg) having the following physical properties.

TLC: Rf 0.36 (hexane:ethyl acetate=2:1);
NMR (CDCl$_3$): δ 7.10–6.95 (m, 2H), 6.86 (d, J=8.8 Hz, 1H), 4.79 (m, 1H), 4.22 (q, J=7.0 Hz, 2H), 3.85 (s, 3H), 3.31 (s, 2H), 3.15–3.00 (m, 2H), 2.75–2.55 (m, 2H), 2.30–2.05 (m, 2H), 2.20–2.00 (m, 2H), 2.00–1.80 (m, 6H), 1.80–1.50 (m, 2H), 1.30 (t, J=7.0 Hz, 3H).

Example 1(1) to Example 1(14)

The following compounds of the present invention were obtained in the same manner as in Example 1 using the compound prepared in Reference Example 4 or a corresponding amine derivative and 2-bromoacetic acid.ethyl ester or a corresponding halogen derivative.

Example 1(1)

2-(4-(3,4-dimethoxyphenyl)-4-cyanopiperidin-1-yl)acetic acid.ethyl ester

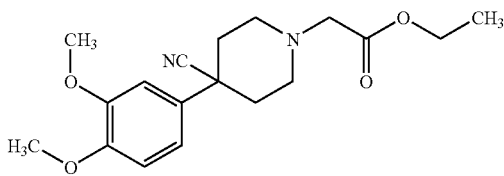

TLC: Rf 0.33 (hexane:ethyl acetate=2:1);
NMR (CDCl$_3$): δ 7.06 (dd, J=8.4, 2.4 Hz, 1H), 6.99 (d, J=2.4 Hz, 1H), 6.87 (d, J=8.4 Hz, 1H), 4.22 (q, J=7.4 Hz, 2H), 3.90 (s, 3H), 3.89 (s, 3H), 3.31 (s, 2H), 3.15–3.00 (m, 2H), 2.75–2.60 (m, 2H), 2.30–2.15 (m, 2H), 2.15–2.00 (m, 2H), 1.30 (t, J=7.4 Hz, 3H).

Example 1(2)

2-(4-(3-ethoxy-4-methoxyphenyl-4-cyanopiperidin-1-yl)acetic acid.ethyl ester

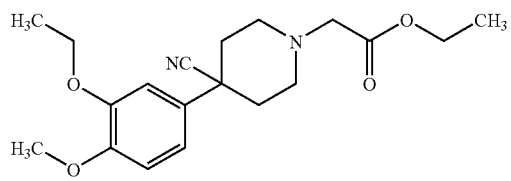

TLC: Rf 0.50 (ethyl acetate);
NMR (CDCl$_3$): δ 7.30–6.95 (m, 2H), 6.87 (d, J=8.4 Hz, 1H), 4.22 (q, J=7.2 Hz, 2H), 4.10 (q, J=7.2 Hz, 2H), 3.88 (s, 3H), 3.31 (s, 2H), 3.13–3.05 (m, 2H), 2.73–2.60 (m, 2H), 2.26–2.15 (m, 2H), 2.12–2.05 (m, 2H), 1.47 (t, J=7.2 Hz, 3H), 1.30 (t, J=7.2 Hz, 3H).

Example 1(3)

2-(4-(3-cyclopropylmethoxy-4-methoxyphenyl)-4-cyanopiperidin-1-yl)acetic acid.ethyl ester

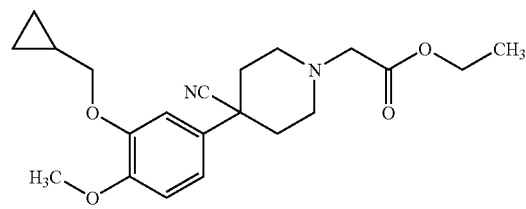

TLC: Rf 0.36 (hexane:ethyl acetate=2:1);
NMR (CDCl$_3$): δ 7.05 (dd, J=8.7, 2.7 Hz, 1H), 6.99 (d, J=2.7 Hz, 1H), 6.87 (d, J=8.7 Hz, 1H), 4.22 (q, J=7.2 Hz, 2H), 3.88 (s, 3H), 3.86 (d, J=6.9 Hz, 2H), 3.30 (s, 2H), 3.15–3.00 (m, 2H), 2.75–2.60 (m, 2H), 2.25–2.10 (m, 2H), 2.15–2.00 (m, 2H), 1.30 (t, J=7.2 Hz, 3H), 1.40–1.20 (m, 1H), 0.70–0.60 (m, 2H), 0.40–0.30 (m, 2H).

Example 1(4)

2-(4-(3-isopropyloxy-4-methoxyphenyl)-4-cyanopiperidin-1-yl)acetic acid.ethyl ester

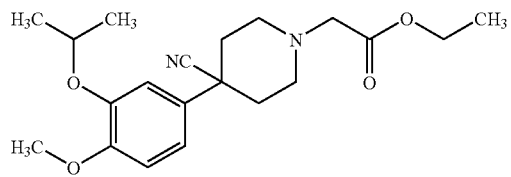

TLC: Rf 0.34 (hexane:ethyl acetate=2:1);
NMR (CDCl$_3$): δ 7.10–7.00 (m, 2H), 6.87 (d, J=8.4 Hz, 1H), 4.54 (sept, J=6.0 Hz, 1H), 4.22 (q, J=7.2 Hz, 2H), 3.85 (s, 3H), 3.30 (s, 2H), 3.20–3.00 (m, 2H), 2.75–2.60 (m, 2H), 2.25–2.10 (m, 2H), 2.15–2.00 (m, 2H), 1.37 (d, J=6.0 Hz, 6H), 1.30 (t, J=7.2 Hz, 3H).

Example 1(5)

2-(4-(3-cyclobutyloxy-4-methoxyphenyl)-4-cyanopiperidin-1-yl)acetic acid.ethyl ester

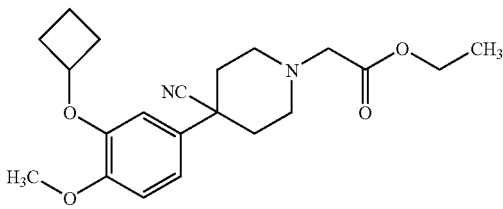

TLC: Rf 0.95 (chloroform:methanol=9:1);
NMR (CDCl$_3$): δ 7.02–7.00 (m, 1H), 6.90–6.80 (m, 2H), 4.67 (quint, J=7.2 Hz, 1H), 4.22 (q, J=7.2 Hz, 2H), 3.87 (s, 3H), 3.31 (s, 2H), 3.12–3.05 (m, 2H), 2.73–2.60 (m, 2H), 2.55–2.43 (m, 2H), 2.33–2.00 (m, 6H), 1.93–1.78 (m, 1H), 1.76–1.60 (m, 1H), 1.30 (t, J=7.2 Hz, 3H).

Example 1(6)

2-(4-(3-cyclopentyloxy-4-methoxyphenyl)-4-cyanopiperidin-1-yl)propanoic acid.ethyl ester

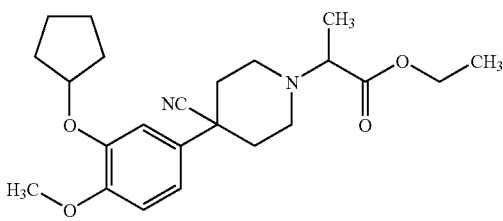

TLC: Rf 0.46 (hexane:ethyl acetate=2:1);
NMR (CDCl$_3$): δ 7.05–6.95 (m, 2H), 6.85 (d, J=8.7 Hz, 1H), 4.79 (m, 1H), 4.30–4.15 (m, 2H), 3.84 (s, 3H), 3.37 (q, J=7.4 Hz, 1H), 3.10–2.95 (m, 2H), 2.90–2.65 (m, 2H), 2.20–2.00 (m, 4H), 2.00–1.80 (m, 6H), 1.75–1.50 (m, 2H), 1.35 (d, J=7.4 Hz, 3H), 1.32 (t, J=7.2 Hz, 3H).

Example 1(7)

4-(4-(3-cyclopentyloxy-4-methoxyphenyl)-4-cyanopiperidin-1-yl)butanoic acid.ethyl ester

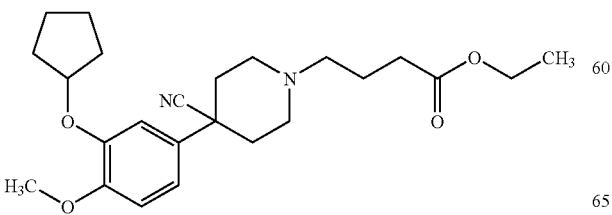

TLC: Rf 0.48 (hexane:ethyl acetate=2:3);
NMR (CDCl$_3$): δ 7.02–6.98 (m, 2H), 6.87–6.84 (m, 1H), 4.83–4.76 (m, 1H), 4.15 (q, J=7.2 Hz, 2H), 3.85 (s, 3H), 3.05–2.97 (m, 2H), 2.52–2.43 (m, 4H), 2.36 (t, J=7.2 Hz, 2H), 2.12–2.03 (m, 4H), 2.01–1.76 (m, 8H), 1.68–1.55 (m, 2H), 1.27 (t, J=7.2 Hz, 3H).

Example 1(8)

2-(4-(3-cyclopentyloxy-4-methoxyphenyl)-4-cyanopiperidin-1-yl)butanoic acid.ethyl ester

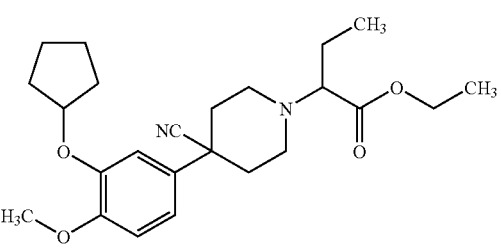

TLC: Rf 0.55 (hexane:ethyl acetate=2:1);
NMR (CDCl$_3$): δ 7.02–6.98 (m, 2H), 6.88–6.83 (m, 1H), 4.83–4.76 (m, 1H), 4.24 (q, J=7.4 Hz, 2H), 3.84 (s, 3H), 3.16–3.10 (m, 1H), 3.05–2.95 (m, 2H), 2.95–2.84 (m, 1H), 2.79–2.69 (m, 1H), 2.13–2.01 (m, 4H), 2.00–1.54 (m, 10H), 1.26 (t, J=7.1 Hz, 3H), 0.95 (t, J=7.4 Hz, 3H).

Example 1(9)

2-(4-(3-cyclopentyloxy-4-difluoromethoxyphenyl)-4-cyanopiperidin-1-yl)acetic acid.ethyl ester

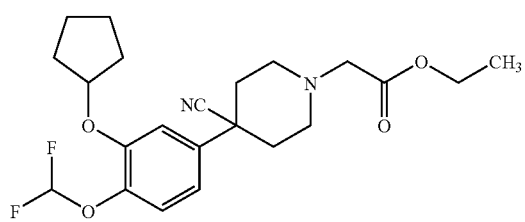

TLC: Rf 0.20 (hexane:ethyl acetate=2:1);
NMR (CDCl$_3$): δ 7.16 (d, J=8.4 Hz, 1H), 7.10 (d, J=2.4 Hz, 1H), 7.03 (dd, J=8.4, 2.4 Hz, 1H), 6.54 (t, J=75.3 Hz, 1H), 4.83 (m, 1H), 4.22 (q, J=7.2 Hz, 2H), 3.31 (s, 2H), 3.20–3.00 (m, 2H), 2.80–2.60 (m, 2H), 2.30–2.10 (m, 2H), 2.15–2.00 (m, 2H), 2.00–1.70 (m, 6H), 1.70–1.55 (m, 2H), 1.30 (t, J=7.2 Hz, 3H).

Example 1(10)

2-(4-(3-cyclopentyloxy-4-ethoxyphenyl)-4-cyanopiperidin-1-yl)acetic acid.ethyl ester

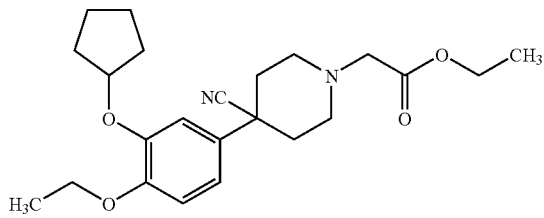

TLC: Rf 0.80 (chloroform:methanol=10:1);

NMR (CDCl$_3$): δ 7.05–6.95 (m, 2H), 6.86 (d, J=9.0 Hz, 1H), 4.78 (m, 1H), 4.22 (q, J=7.2 Hz, 2H), 4.06 (q, J=7.2 Hz, 2H), 3.30 (s, 2H), 3.10–3.00 (m, 2H), 2.75–2.60 (m, 2H), 2.25–2.10 (m, 2H), 2.15–2.00 (m, 2H), 1.95–1.75 (m, 6H), 1.70–1.55 (m, 2H), 1.42 (t, J=7.2 Hz, 3H), 1.30 (t, J=7.2 Hz, 3H).

Example 1(11)

2-(4-(3-cyclopentyloxy-4-ethoxyphenyl)-4-cyanopiperidin-1-yl)propanoic acid.ethyl ester

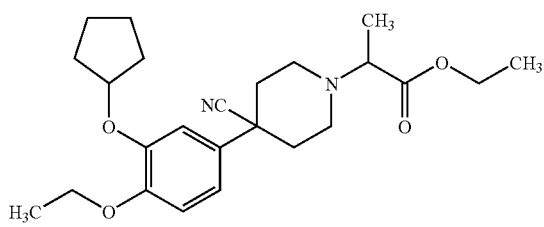

TLC: Rf 0.41 (hexane:ethyl acetate=2:1);

NMR (CDCl$_3$): δ 7.05–6.95 (m, 2H), 6.86 (d, J=9.0 Hz, 1H), 4.78 (m, 1H), 4.30–4.15 (m, 2H), 4.05 (q, J=6.9 Hz, 2H), 3.36 (q, J=6.9 Hz, 1H), 3.10–2.95 (m, 2H), 2.90–2.65 (m, 2H), 2.20–2.00 (m, 4H), 2.00–1.80 (m, 6H), 1.70–1.50 (m, 2H), 1.42 (t, J=6.9 Hz, 3H), 1.34 (d, J=6.9 Hz, 3H), 1.32 (t, J=6.9 Hz, 3H).

Example 1(12)

2-(4-(3-cyclopentyloxy-4-isopropyloxyphenyl)-4-cyanopiperidin-1-yl)acetic acid.ethyl ester

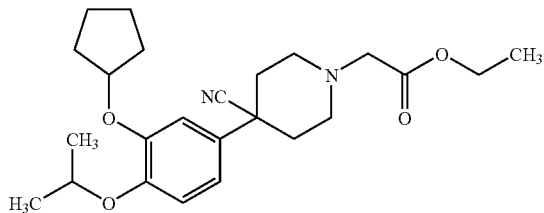

TLC: Rf 0.87 (chloroform:methanol=9:1);

NMR (CDCl$_3$): δ 7.01–6.97 (m, 2H), 6.89 (d, J=7.8 Hz, 1H), 4.804.74 (m, 1H), 4.42 (sept, J=6.0 Hz, 1H), 4.22 (q, J=7.0 Hz, 2H), 3.30 (s, 2H), 3.12–3.02 (m, 2H), 2.72–2.61 (m, 2H), 2.26–2.14 (m, 2H), 2.12–2.05 (m, 2H), 1.90–1.75 (m, 2H), 1.65–1.50 (m, 6H), 1.31 (d, J=6.0 Hz, 6H), 1.28 (t, J=7.0 Hz, 3H).

Example 1(13)

2-(4-(3-isopropyloxy-4-difluoromethoxyphenyl)-4-cyanopiperidin-1-yl)acetic acid.ethyl ester

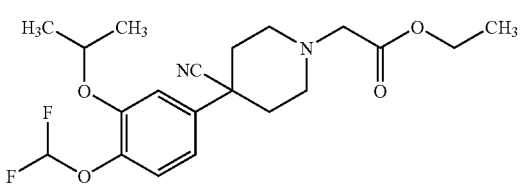

TLC: Rf 0.63 (hexane:ethyl acetate=1:3);

NMR (CDCl$_3$): δ 7.17 (d, J=8.4 Hz, 1H), 7.11 (d, J=2.3 Hz, 1H), 7.05 (dd, J=8.4, 2.3 Hz, 1H), 6.57 (t, J=75.5 Hz, 1H), 4.58 (sept, J=6.1 Hz, 1H), 4.22 (q, J=7.2 Hz, 2H), 3.31 (s, 2H), 3.14–3.06 (m, 2H), 2.73–2.63 (m, 2H), 2.26–2.15 (m, 2H), 2.21–2.04 (m, 2H), 1.37 (d, J=6.1 Hz, 6H), 1.30 (t, J=7.2 Hz, 3H).

Example 1(14)

2-(4-(3-cyclohexyloxy-4-difluoromethoxyphenyl)-4-cyanopiperidin-1-yl)acetic acid.ethyl ester

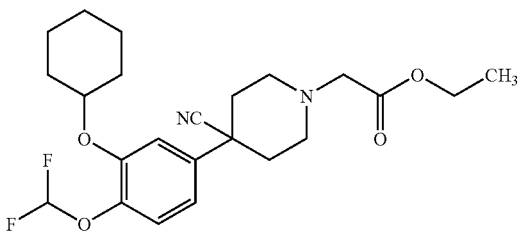

TLC: Rf 0.53 (hexane:ethyl acetate=1:1);

NMR (CDCl$_3$): δ 7.17 (d, J=8.6 Hz, 1H), 7.11 (d, J=2.3 Hz, 1H), 7.06 (dd, J=8.6, 2.3 Hz, 1H), 6.58 (t, J=75.5 Hz, 1H), 4.31 (m, 1H), 4.22 (q, J=7.2 Hz, 2H), 3.31 (s, 2H), 3.13–3.06 (m, 2H), 2.72–2.63 (m, 2H), 2.25–2.15 (m, 2H), 2.12–2.03 (m, 2H), 1.99–1.89 (m, 2H), 1.85–1.72 (m, 2H), 1.66–1.50 (m, 2H), 1.50–1.23 (m, 4H), 1.28 (t, J=7.2 Hz, 3H).

EXAMPLE 2

2-(4-(3-cyclopentyloxy-4-methoxyphenyl)-4-cyanopiperidin-1-yl)acetic acid

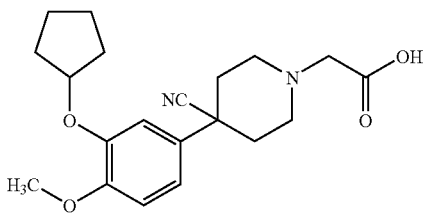

A mixture of the compound (330 mg) prepared in Example 1, ethanol (5 ml) and a 2 N aqueous sodium hydroxide solution (0.86 ml) was stirred at room temperature for 35 minutes. The reaction mixture was neutralized with 2 N hydrochloric acid (0.86 ml), and subjected to azeotropy with toluene. The residue was purified by silica gel column chromatography (chloroform:methanol:water=10:2:0.1) to thereby the compound of the present invention (278 mg) having the following physical properties.

TLC: Rf 0.22 (chloroform:methanol:acetic acid=10:1:0.2);

NMR (CDCl$_3$): δ 7.10–7.00 (m, 2H), 6.88 (d, J=9.0 Hz, 1H), 4.83 (m, 1H), 4.30–4.00 (br, 1H), 3.85 (s, 3H), 3.56 (br.d, J 12.6 Hz, 2H), 3.46 (s, 2H), 2.99 (br.t, J=12.6 Hz, 2H), 2.51 (br.t, J=12.6 Hz, 2H), 2.19 (br.d, J=12.6 Hz, 2H), 2.05–1.75 (m, 6H), 1.70–1.55 (m, 2H).

Example 2(1) to Example 2(14)

The following compounds of the present invention were obtained in the same manner as in Example 2 using the compound prepared in Example 1(1) to Example 1(14) instead of the compound prepared in Example 1.

Example 2(1)

2-(4-(3,4-dimethoxyphenyl)-4-cyanopiperidin-1-yl)acetic acid

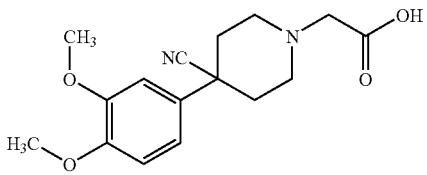

TLC: Rf 0.38 (chloroform:methanol:acetic acid=10:2:1);

NMR (DMSO-d$_6$): δ 7.10–7.00 (m, 2H), 6.97 (d, J=9.3 Hz, 1H), 3.78 (s, 3H), 3.75 (s, 3H), 4.00–3.00 (br, 1H), 3.23 (s, 2H), 3.05–2.95 (m, 2H), 2.65–2.50 (m, 2H), 2.20–1.95 (m, 4H).

Example 2(2)

2-(4-(3-ethoxy-4-methoxyphenyl-4-cyanopiperidin-1-yl)acetic acid

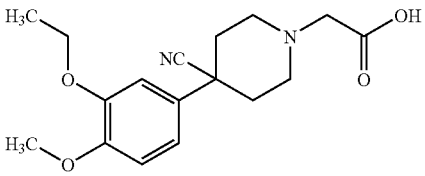

TLC: Rf 0.30 (chloroform:methanol=9:1);

NMR (CDCl$_3$): δ 7.10–7.05 (m, 2H), 6.95–6.85 (m, 1H), 4.15 (q, J=6.9 Hz, 2H), 3.88 (s, 3H), 3.50–3.40 (m, 4H), 3.10–2.95 (m, 2H), 2.60–2.40 (m, 3H), 2.25–2.15 (m, 2H), 1.49 (t, J=6.9 Hz, 3H).

Example 2(3)

2-(4-(3-cyclopropylmethoxy-4-methoxyphenyl)-4-cyanopiperidin-1-yl)acetic acid

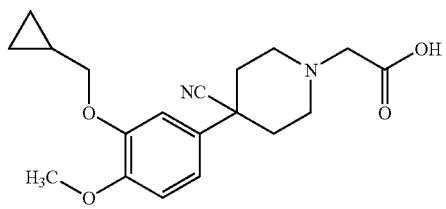

TLC: Rf 0.59 (chloroform:methanol:acetic acid=10:2:1);

NMR (DMSO-d$_6$): δ 7.05–6.95 (m, 3H), 3.83 (d, J=6.9 Hz, 2H), 3.76 (s, 3H), 3.60–2.90 (br, 1H), 3.27 (s, 2H), 3.05–2.95 (m, 2H), 2.70–2.50 (m, 2H), 2.20–1.95 (m, 4H), 1.20 (m, 1H), 0.65–0.55 (m, 2H), 0.40–0.25 (m, 2H).

Example 2(4)

2-(4-(3-isopropyloxy-4-methoxyphenyl)-4-cyanopiperidin-1-yl)acetic acid

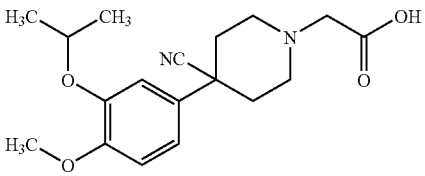

TLC: Rf 0.10 (ethyl acetate);

NMR (CDCl$_3$): δ 7.15–7.00 (m, 2H), 6.95–6.85 (m, 1H), 4.59 (sept, J=6.0 Hz, 1H), 3.86 (s, 3H), 3.60–3.50 (m, 2H), 3.46 (s, 2H), 3.05–2.93 (m, 2H), 2.85–2.60 (m, 1H), 2.60–2.40 (m, 2H), 2.24–2.12 (m, 2H), 1.37 (d, J=6.0 Hz, 6H).

Example 2(5)

2-(4-(3-cyclobutyloxy-4-methoxyphenyl)-4-cyanopiperidin-1-yl)acetic acid

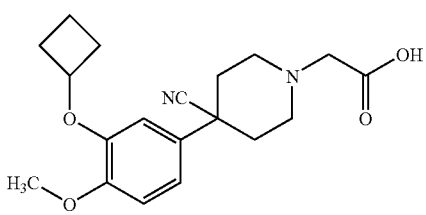

TLC: Rf 0.10 (ethyl acetate);
NMR (CDCl$_3$): δ 7.10–7.00 (m, 1H), 6.95–6.85 (m, 2H), 4.71 (quint, J=7.5 Hz, 1H), 3.87 (s, 3H), 3.70–3.40 (m, 2H), 3.49 (s, 2H), 3.10–2.95 (m, 2H), 2.70–2.00 (m, 9H), 2.00–1.80 (m, 1H), 1.80–1.60(m, 1H).

Example 2(6)

2-(4-(3-cyclopentyloxy-4-methoxyphenyl)-4-cyanopiperidin-1-yl)propanoic acid

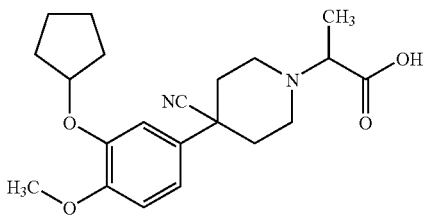

TLC: Rf 0.67 (chloroform:methanol:acetic acid=15:2:1);
NMR (DMSO-d$_6$) 7.03–6.94 (m, 3H), 4.88 4.80 (m, 1H), 3.73 (s, 3H), 3.30 (q, J=7.1 Hz, 1H), 4.00–2.70 (br, 1H), 3.00–2.90 (m, 2H), 2.78–2.68 (m, 1H), 2.66–2.56 (m, 1H), 2.13–2.04 (m, 2H), 2.02–1.80 (m, 4H), 1.76–1.63 (m, 4H), 1.63–1.50 (m, 2H), 1.19 (d, J=7.1 Hz, 3H).

Example 2(7)

4-(4-(3-cyclopentyloxy-4-methoxyphenyl)-4-cyanopiperidin-1-yl))butanoic acid

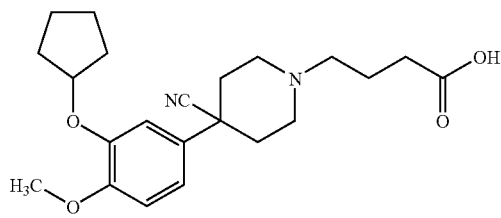

TLC: Rf 0.55 (chloroform:methanol=8:1);
NMR (DMSO-d$_6$): δ 7.03–6.94 (m, 3H), 4.87–4.81 (m, 1H), 3.74 (s, 3H), 3.31 (br, 1H), 3.01–2.96 (m, 2H), 2.44–2.38 (m, 2H), 2.33–2.21 (m, 4H), 2.13–2.08 (m, 2H), 2.00–1.94 (m, 2H), 1.92–1.83 (m, 2H), 1.76–1.63 (m, 6H), 1.62–1.54 (m, 2H).

Example 2(8)

2-(4-(3-cyclopentyloxy-4-methoxyphenyl)-4-cyanopiperidin-1-yl))butanoic acid

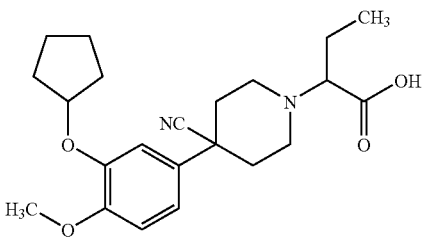

TLC: Rf 0.52 (chloroform:methanol=9:1);
NMR (DMSO-d$_6$): δ 7.02–6.93 (m, 3H), 4.87–4.80 (m, 1H), 3.72 (s, 3H), 3.31 (br, 1H), 3.05 (t, J=7.4 Hz, 1H), 2.97–2.86 (m, 2H), 2.81–2.70 (m, 1H), 2.64–2.54 (m, 1H), 2.13–2.04 (m, 2H), 1.99–1.80 (m, 4H), 1.75–1.63 (m, 6H), 1.63–1.51 (m, 2H), 0.87 (t, J=7.4 Hz, 3H).

Example 2(9)

2-(4-(3-cyclopentyloxy-4-difluoromethoxyphenyl)-4-cyanopiperidin-1-yl)acetic acid

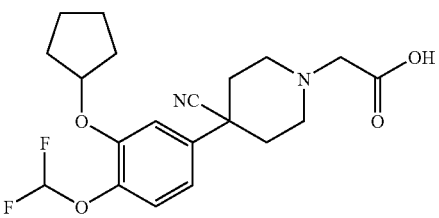

TLC: Rf 0.35 (chloroform:methanol:acetic acid=10:1:0.2);
NMR (DMSO-d$_6$): δ 7.25–7.15 (m, 2H), 7.09 (dd, J=8.1, 2.1 Hz, 1H), 7.01 (t, J=75.0 Hz, 1H), 4.98 (m, 1H), 3.60–3.00 (br, 1H), 3.26 (s, 2H), 3.10–2.95 (m, 2H), 2.70–2.50 (m, 2H), 2.20–2.00 (m, 4H), 2.00–1.80 (m, 2H), 1.80–1.60 (m, 4H), 1.65–1.50 (m, 2H).

Example 2(10)

2-(4-(3-cyclopentyloxy-4-ethoxyphenyl)-4-cyanopiperidin-1-yl)acetic acid

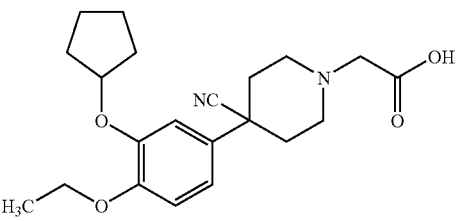

TLC: Rf 0.39 (chloroform:methanol:acetic acid=10:1:0.2);

NMR (DMSO-d$_6$): δ 7.05–6.90 (m, 3H), 4.83 (m, 1H), 4.00 (q, J=6.9 Hz, 2H), 4.00–3.00 (br, 2H), 3.23 (s, 2H), 3.05–2.95 (m, 2H), 2.65–2.50 (m, 2H), 2.15–1.90 (m, 4H), 1.95–1.80 (m, 2H), 1.80–1.60 (m, 4H), 1.65–1.50 (m, 2H), 1.29 (t, J=6.9 Hz, 3H).

Example 2(11)

2-(4-(3-cyclopentyloxy-4-ethoxyphenyl)-4-cyanopiperidin-1-yl)propanoic acid

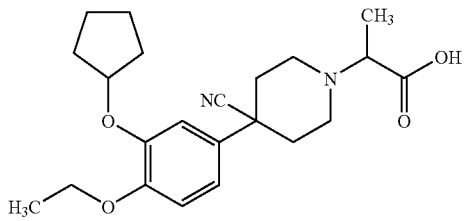

TLC: Rf 0.47 (chloroform:methanol:acetic acid=10:1:0.2);

NMR (DMSO-d$_6$): δ 7.05–6.90 (m, 3H), 4.83 (m, 1H), 3.99 (q, J=6.9 Hz, 2H), 3.90–3.00 (br, 1H), 3.31 (q, J=6.9 Hz, 1H), 3.05–2.85 (m, 2H), 2.73 (m, 1H), 2.61 (m, 1H), 2.15–2.00 (m, 2H), 2.05–1.80 (m, 4H), 1.80–1.60 (m, 4H), 1.65–1.50 (m, 2H), 1.29 (t, J=6.9 Hz, 3H), 1.19 (d, J=6.9 Hz, 3H).

Example 2(12)

2-(4-(3-cyclopentyloxy-4-isopropyloxyphenyl)-4-cyanopiperidin-1-yl)acetic acid

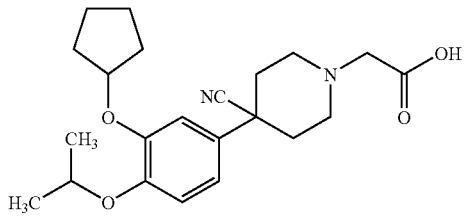

TLC: Rf 0.20 (chloroform:methanol=9:1);

NMR (CDCl$_3$): δ 7.04 (d, J=2.1 Hz, 1H), 7.00 (dd, J=8.4, 2.1 Hz, 1H), 6.91 (d, J=8.4 Hz, 1H), 4.84–4.78 (m, 1H), 4.44 (sept, J=6.0 Hz, 1H), 3.48–3.34 (m, 4H), 3.02–2.90 (m, 2H), 2.48–2.30 (m, 2H), 2.20–1.75 (m, 9H), 1.70–1.60 (m, 2H), 1.32 (d, J=6.0 Hz, 6H).

Example 2(13)

2-(4-(3-isopropyloxy-4-difluoromethoxyphenyl)-4-cyanopiperidin-1-yl)acetic acid

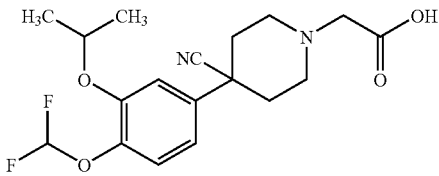

TLC: Rf 0.35 (chloroform:methanol:acetic acid=10:2:1);

NMR (DMSO-d$_6$): δ 7.25 (d, J=2.2 Hz, 1H), 7.21 (d, J=8.4 Hz, 1H), 7.11 (dd, J=8.4, 2.2 Hz, 1H), 7.04 (t, J=74.6 Hz, 1H), 4.74 (sept, J=5.9 Hz, 1H), 3.31 (br, 1H), 3.23 (s, 2H), 3.05–2.98 (m, 2H), 2.63–2.53 (m, 2H), 2.14–1.98 (m, 4H), 1.28 (d, J=5.9 Hz, 6H).

Example 2(14)

2-(4-(3-cyclohexyloxy-4-difluoromethoxyphenyl)-4-cyanopiperidin-1-yl)acetic acid

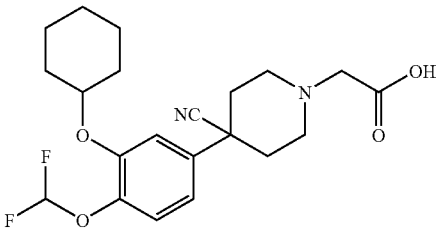

TLC: Rf 0.50 (chloroform:methanol:acetic acid=10:2:1);

NMR (DMSO-d6): δ 7.26 (d, J=2.1 Hz, 1H), 7.21 (d, J=8.5 Hz, 1H), 7.10 (dd, J=8.5, 2.1 Hz, 1H), 7.03 (t, J=74.6 Hz, 1H), 4.52 (m, 1H), 3.33 (br, 1H), 3.19 (s, 2H), 3.06–2.97 (m, 2H), 2.61–2.50 (m, 2H), 2.15–1.98 (m, 4H), 1.93–1.82 (m, 2H), 1.75–1.64 (m, 2H), 1.55–1.25 (m, 6H).

REFERENCE EXAMPLE 5

N-(1-methyl-1-methoxyethyl)-2-(4-(3-cyclopentyloxy-4-methoxyphenyl)-4-cyanopiperidin-1-yl)acetamide

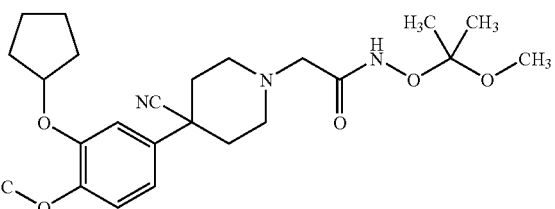

The compound (239 mg) prepared in Example 2, 1-ethyl-3-(3-dimethylaminopropyl)-carbodiimide (EDC; 192 mg), 1-hydroxybenzotriazole (HOBt; 135 mg), dimethylformamide (4 ml) and (1-methoxy-1-methylethyl)oxyamine (0.35 ml) was stirred at room temperature for 3 hours. The reaction mixture was diluted with ethyl acetate, washed with water (twice), dried over anhydrous sodium sulfate, and concentrated under reduced pressure. The residue was purified by silica gel column chromatography (hexane:ethyl acetate=1:1→ethyl acetate alone) to thereby obtain the title compound (289 mg) having the following physical properties.

TLC: Rf 0.26 (ethyl acetate);

NMR (CDCl$_3$): δ 8.94 (br.s, 1H), 7.05–6.90 (m, 2H), 6.87 (d, J=8.4 Hz, 1H), 4.81 (m, 1H), 3.86 (s, 3H), 3.36 (s, 3H), 3.23 (s, 2H), 3.10–3.00 (m, 2H), 2.80–2.65 (m, 2H), 2.20–2.00 (m, 2H), 2.10–1.75 (m, 8H), 1.70–1.55 (m, 2H), 1.46 (s, 6H).

EXAMPLE 3

N-hydroxy-2-(4-(3-cyclopentyloxy-4-methoxyphenyl)-4-cyanopiperidin-1-yl)acetamide.hydrochloride

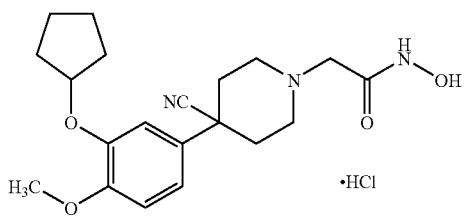

A mixture of the compound (280 mg) prepared in Reference Example 5, methanol (3 ml) and 2 N hydrochloric acid (0.35 ml) was stirred at room temperature for 1 hour. The reaction mixture was subjected to azeotropy with toluene. The residue was ground and filtered with isopropyl ether and a small amount of methanol to thereby obtain the compound of the present invention (189 mg) having the following physical properties.

TLC: Rf 0.38 (chloroform:methanol=10:1);
NMR (pyridine-$d_5$+CDCl$_3$): δ 7.09 (d, J=2.4 Hz, 1H), 6.99 (dd, J=8.4, 2.4 Hz, 1H), 6.88 (d, J=8.4 Hz, 1H), 6.08 (br.s, 3H), 4.75 (m, 1H), 3.72 (s, 3H), 3.30 (s, 2H), 3.02 (brd, J=14.4 Hz, 2H), 2.75–2.60 (m, 2H), 2.20–1.95 (m, 4H), 2.00–1.65 (m, 6H), 1.60–1.40 (m, 2H).

Example 4 to Example 4(11)

The following compounds of the present invention were obtained in the same manner as in Reference Example 5→Example 3 using the compound prepared in Example 2(1) to Example 2(12) instead of the compound prepared in Example 2.

EXAMPLE 4

N-hydroxy-2-(4-(3,4-dimethoxyphenyl)-4-cyanopiperidin-1-yl)acetamide.hydrochloride

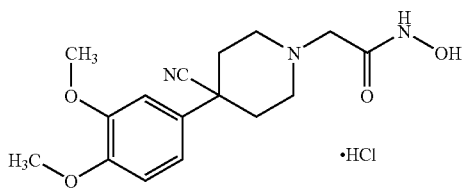

TLC: Rf 0.21 (chloroform:methanol=10:1);
NMR (pyridine-$d_5$+CDCl$_3$): δ 7.05–6.95 (m, 2H), 6.85 (d, J=9.0 Hz, 1H), 6.80–6.00 (br, 3H), 3.75 (s, 6H), 3.28 (s, 2H), 3.05–2.95 (m, 2H), 2.70–2.55 (m, 2H), 2.20–1.90 (m, 4H).

Example 4(1)

N-hydroxy-2-(4-(3-ethoxy-4-methoxyphenyl-4-cyanopiperidin-1-yl)acetamide.hydrochloride

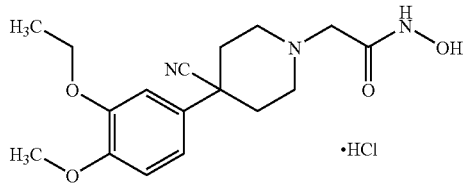

TLC: Rf 0.15 (ethyl acetate);
NMR (pyridine-$d_5$+CDCl$_3$) 8.30–7.00 (m, 5H), 6.93–6.87 (m, 1H), 3.95 (q, J=6.9 Hz, 2H), 3.74 (s, 3H), 3.34 (s, 2H), 3.10–3.00 (m, 2H), 2.75–2.60 (m, 2H), 2.15–1.95 (m, 4H), 1.33 (t, J=6.9 Hz, 3H).

Example 4(2)

N-hydroxy-2-(4-(3-cyclopropylmethoxy-4-methoxyphenyl)-4-cyanopiperidin-1-yl)acetamide.hydrochloride

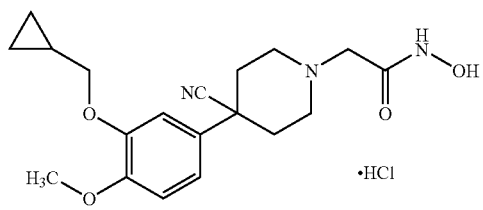

TLC: Rf 0.31 (chloroform:methanol=10:1);
NMR (pyridine-$d_5$+CDCl$_3$): δ 8.80–7.50 (br, 3H), 7.08 (d, J=2.4 Hz, 1H), 7.02 (dd, J=8.4, 2.4 Hz, 1H), 6.87 (d, J=8.4 Hz, 1H), 3.83 (d, J=6.9 Hz, 2H), 3.73 (s, 3H), 3.30 (s, 2H), 3.10–2.90 (m, 2H), 2.70–2.55 (m, 2H), 2.15–1.95 (m, 4H), 1.26 (m, 1H), 0.55–0.45 (m, 2H), 0.35–0.25 (m, 2H).

Example 4(3)

N-hydroxy-2-(4-(3-isopropyloxy-4-methoxyphenyl)-4-cyanopiperidin-1-yl)acetamide.hydrochloride

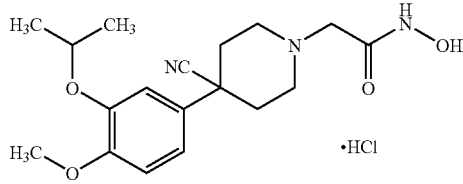

TLC: Rf 0.22 (ethyl acetate);
NMR (pyridine-$d_5$+CDCl$_3$): δ 7.10 (d, J=2.1 Hz, 1H), 7.02 (dd, J=6.0, 2.1 Hz, 1H), 6.88 (d, J=6.0 Hz, 1H), 6.25–5.50 (m, 3H), 4.51 (sept, J=6.0 Hz, 1H), 3.73 (s, 3H), 3.28 (s, 2H), 3.05–2.95 (m, 2H), 2.75–2.55 (m, 2H), 2.15–1.95 (m, 4H), 1.28 (d, J=6.0 Hz, 6H).

Example 4(4)

N-hydroxy-2-(4-(3-cyclobutyloxy-4-methoxyphenyl)-4-cyanopiperidin-1-yl)acetamide.hydrochloride

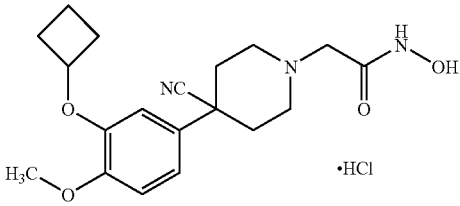

TLC: Rf 0.20 (ethyl acetate);

NMR (pyridine-$d_5$+CDCl$_3$): δ 7.05–7.00 (m, 2H), 6.95–6.88 (m, 1H), 6.80–6.20 (m, 3H), 4.65 (quint, J=6.9 Hz, 1H), 3.75 (s, 3H), 3.36 (s, 2H), 3.10–3.00 (m, 2H), 2.75–2.65 (m, 2H), 2.40–2.30 (m, 2H), 2.20–1.90 (m, 6H), 1.75–1.40 (m, 2H).

Example 4(5)

N-hydroxy-2-(4-(3-cyclopentyloxy-4-methoxyphenyl)-4-cyanopiperidin-1-yl)propanamide.hydrochloride

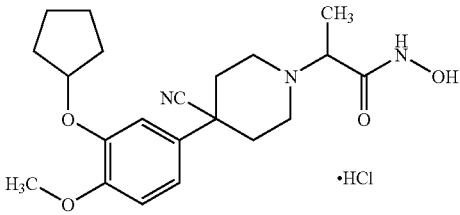

TLC: Rf 0.44 (chloroform:methanol=10:1);

NMR (pyridine-$d_5$+CDCl$_3$): δ 7.20 (d, J=2.3 Hz, 1H), 7.09 (dd, J=8.3, 2.3 Hz, 1H), 6.94 (d, J=8.3 Hz, 1H), 6.45 (br, 3H), 4.82–4.75 (m, 1H), 3.74 (s, 3H), 3.53 (q, J=6.9 Hz, 1H), 3.23–3.02 (m, 3H), 2.93–2.82 (m, 1H), 2.26–2.10 (m, 4H), 1.95–1.65 (m, 6H), 1.53–1.41 (m, 2H), 1.47 (d, J=6.9 Hz, 3H).

Example 4(6)

N-hydroxy-4-(4-(3-cyclopentyloxy-4-methoxyphenyl)-4-cyanopiperidin-1-yl)butanamide.hydrochloride

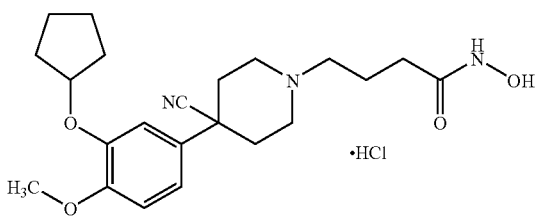

TLC: Rf 0.63 (chloroform:methanol=9:1);

NMR (pyridine-$d_5$+CDCl$_3$): δ 7.29 (d, J=2.6 Hz, 1H), 7.17 (dd, J=8.7, 2.6 Hz, 1H), 6.87 (d, J=8.7 Hz, 1H), 6.04 (br, 3H), 4.89483 (m, 1H), 3.72 (s, 3H), 3.32–3.28 (m, 2H), 2.90–2.63 (m, 6H), 2.46 (t, J=6.9 Hz, 2H), 2.26–2.14 (m, 4H), 1.92–1.85 (m, 4H), 1.80–1.66 (m, 2H), 1.56–1.45 (m, 2H).

Example 4(7)

N-hydroxy-2-(4-(3-cyclopentyloxy-4-methoxyphenyl)-4-cyanopiperidin-1-yl)butanamide.hydrochloride

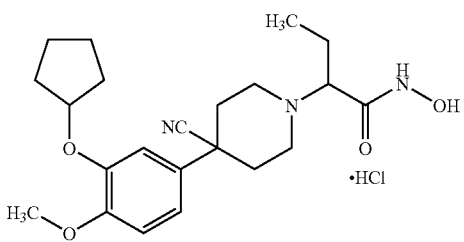

TLC: Rf 0.54 (chloroform:methanol=9:1);

NMR (pyridine-$d_5$+CDCl$_3$): δ 7.20 (d, J=2.4 Hz, 1H), 7.10 (dd, J=8.5, 2.4 Hz, 1H), 6.92 (d, J=8.5 Hz, 1H), 6.35 (br, 3H), 4.83–4.76 (m, 1H), 3.72 (s, 3H), 3.34–3.15 (m, 4H), 3.06–2.96 (m, 1H), 2.27–2.00 (m, 5H), 1.95–1.62 (m, 7H), 1.54–1.39 (m, 2H), 0.99 (t, J=7.2 Hz, 3H).

Example 4(8)

N-hydroxy-2-(4-(3-cyclopentyloxy-4-difluoromethoxyphenyl)-4-cyanopiperidin-1-yl)acetamide.hydrochloride

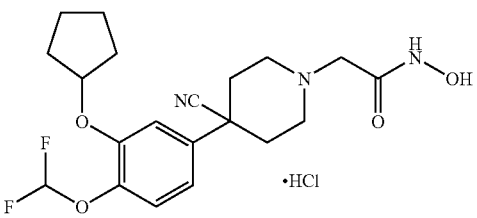

TLC: Rf 0.36 (chloroform:methanol=10:1);

NMR (pyridine-$d_5$+CDCl$_3$): δ 7.23 (d, J=8.4 Hz, 1H), 7.18 (d, J=1.8 Hz, 1H), 6.97 (dd, J=8.4, 1.8 Hz, 1H), 6.97 (t, J=75.0 Hz, 1H), 6.60–5.60 (br, 3H), 4.74 (m, 1H), 3.31 (s, 2H), 3.10–3.00 (m, 2H), 2.70–2.60 (m, 2H), 2.20–2.00 (m, 4H), 1.85–1.60 (m, 6H), 1.60–1.40 (m, 2H).

Example 4(9)

N-hydroxy-2-(4-(3-cyclopentyloxy-4-ethoxyphenyl)-4-cyanopiperidin-1-yl)acetamide.hydrochloride

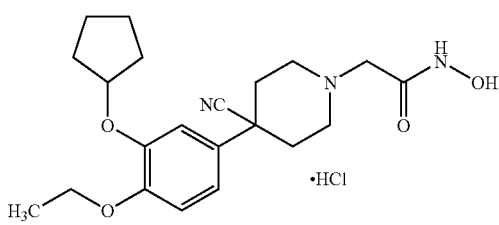

TLC: Rf 0.36 (chloroform:methanol=10:1);

NMR (pyridine-$d_5$+CDCl$_3$): δ 8.10–7.20 (br, 3H), 7.10 (d, J=2.1 Hz, 1H), 7.00 (dd, J=8.4, 2.1 Hz, 1H), 6.90 (d, J=8.4 Hz, 1H), 4.76 (m, 1H), 3.97 (q, J=6.9 Hz, 2H), 3.31 (s, 2H), 3.10–2.95 (m, 2H), 2.75–2.60 (m, 2H), 2.20–1.95 (m, 4H), 2.00–1.65 (m, 6H), 1.60–1.40 (m, 2H), 1.31 (t, J=6.9 Hz, 3H).

Example 4(10)

N-hydroxy-2-(4-(3-cyclopentyloxy-4-ethoxyphenyl)-4-cyanopiperidin-1-yl)propanamide.hydrochloride

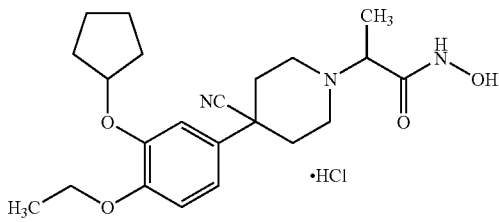

TLC: Rf 0.37 (chloroform:methanol=10:1);

NMR (pyridine-$d_5$+CDCl$_3$): δ 7.14 (br.s, 1H), 7.03 (br.d, J=8.4 Hz, 1H), 6.90 (d, J=8.4 Hz, 1H), 7.30–6.60 (br, 3H), 4.77 (m, 1H), 3.97 (q, J=7.2 Hz, 2H), 3.42 (m, 1H), 3.15–3.00 (m, 2H), 2.96 (m, 1H), 2.77 (m, 1H), 2.20–2.00 (m, 4H), 2.00–1.60 (m, 6H), 1.60–1.40 (m, 2H), 1.42 (d, J=6.6 Hz, 3H), 1.31 (t, J=7.2 Hz, 3H).

Example 4(11)

N-hydroxy-2-(4-(3-cyclopentyloxy-4-isopropyloxyphenyl)-4-cyanopiperidin-1-yl)acetamide.hydrochloride

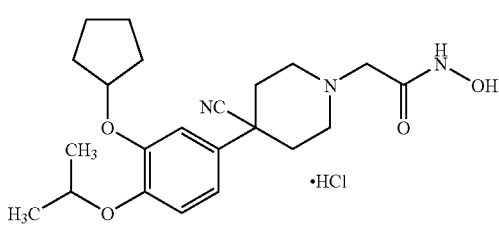

TLC: Rf 0.40 (chloroform:methanol=9:1);

NMR (pyridine-$d_5$+CDCl$_3$): δ 7.15–7.10 (m, 1H), 7.05–6.90 (m, 2H), 5.80–5.35 (m, 3H), 4.78–4.72 (m, 1H), 4.46 (sept, J=6.0 Hz, 1H), 3.28 (s, 2H), 3.04–2.96 (m, 2H), 2.68–2.58 (m, 2H), 2.15–1.95 (m, 4H), 1.95–1.65 (m, 6H), 1.58–1.45 (m, 2H), 1.28 (d, J=6.0 Hz, 6H).

EXAMPLE 5

3-(4-(3-cyclopentyloxy-4-methoxyphenyl)-4-cyanopiperidin-1-yl)propanoic acid.methyl ester

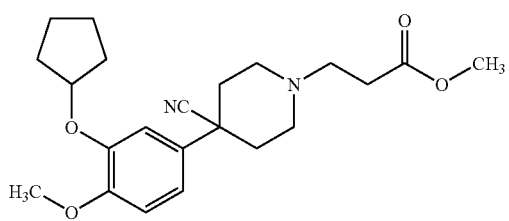

To a tetrahydrofuran (5 ml) solution of the compound (0.45 g) prepared in Reference Example 4, triethylamine (0.37 ml) and methyl acrylate (0.36 ml) were added, followed by stirring at 45° C. for 1 day. The reaction mixture was cooled to room temperature, poured into water, and extracted with ethyl acetate. The extract was washed with water and saturated saline in this order, dried over anhydrous magnesium sulfate, and concentrated under reduced pressure. The residue was purified by silica gel column chromatography (hexane:ethyl acetate=1:1) to thereby obtain the compound of the present invention (0.4505 g) having the following physical properties.

TLC: Rf 0.42 (hexane:ethyl acetate=2:3);

NMR (CDCl$_3$): δ 7.02–6.97 (m, 2H), 6.87–6.83 (m, 1H), 4.83–4.76 (m, 1H), 3.85 (s, 3H), 3.70 (s, 3H), 3.05–2.96 (m, 2H), 2.81 (t, J=7.2 Hz, 2H), 2.59–2.49 (m, 2H), 2.55 (t, J=7.2 Hz, 2H), 2.12–2.02 (m, 4H), 2.02–1.76 (m, 6H), 1.70–1.50 (m, 2H).

EXAMPLE 6

(2R)-2-(4-(3-cyclopentyloxy-4-methoxyphenyl)-4-cyanopiperidin-1-yl)propanoic acid.methyl ester

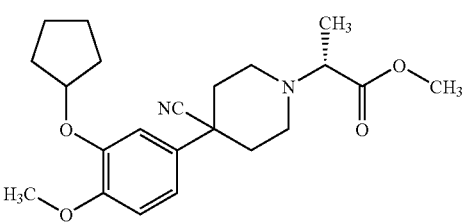

(S)-(−)-Methyl lactate (0.34 ml) was dissolved in methylene chloride (3 ml) under argon atmosphere at 0° C., and anhydrous trifluoromethane sulfonic acid (0.661 ml) and 2,6-lutidine (0.457 ml) were added, followed by stirring at room temperature for 30 minutes. To the reaction mixture, a methylene chloride (2.5 ml) solution of the compound (400 mg) prepared in Reference Example 4 and triethylamine (0.358 ml) were added in this order, followed by stirring at room temperature for 18 hours. Water (5 ml) was added to the reaction mixture for liquid separation. The aqueous layer was extracted with ethyl acetate (5 ml×3 times). The extract was mixed with the organic layer, was dried over anhydrous sodium sulfate, and concentrated under reduced pressure. The residue was purified by silica gel column chromatography (hexane:ethyl acetate=3:1) to thereby obtain the compound of the present invention (492 mg) having the following physical properties.

TLC: Rf 0.90 (chloroform:methanol=9:1);

NMR (CDCl$_3$): δ 7.05–6.97 (m, 2H), 6.87–6.83 (m, 1H), 4.85–4.75 (m, 1H), 3.84 (s, 3H), 3.76 (s, 3H), 3.39 (q, J=7.0 Hz, 1H), 3.10–2.95 (m, 2H), 2.85–2.68 (m, 2H), 2.15–2.05 (m, 4H), 2.00–1.75 (m, 6H), 1.65–1.45 (m, 2H), 1.35 (d, J=7.0 Hz, 3H).

Example 6(1)

(2S)-2-(4-(3-cyclopentyloxy-4-methoxyphenyl)-4-cyanopiperidin-1-yl)propanoic acid.methyl ester

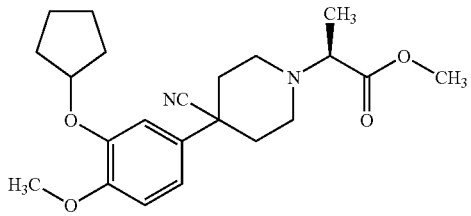

The compound of the present invention having the following physical properties was obtained in the same manner as in Example 6 using (R)-(+)-methyl lactate instead of (S)-(−)-methyl lactate.

TLC: Rf 0.90 (chloroform:methanol=9:1);

NMR (CDCl$_3$): δ 7.05–6.97 (m, 2H), 6.87–6.83 (m, 1H), 4.85–4.75 (m, 1H), 3.84 (s, 3H), 3.76 (s, 3H), 3.39 (q, J=7.0 Hz, 1H), 3.10–2.95 (m, 2H), 2.85–2.68 (m, 2H), 2.15–2.05 (m, 4H), 2.00–1.75 (m, 6H), 1.65–1.45 (m, 2H), 1.35 (d, J=7.0 Hz, 3H).

Example 7 to Example 7(2)

The following compounds of the present invention were obtained in the same manner as in Example 2 using the compound prepared in Example 5, Example 6 or Example 6(1) instead of the compound prepared in Example 1.

EXAMPLE 7

3-(4-(3-cyclopentyloxy-4-methoxyphenyl)-4-cyanopiperidin-1-yl)propanoic acid

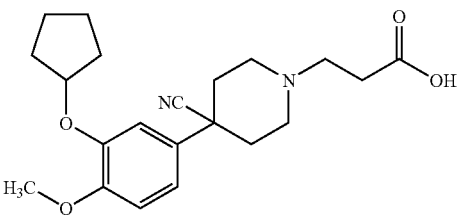

TLC: Rf 0.43 (chloroform:methanol=9:1);

NMR (DMSO-d$_6$): δ 7.03–6.95 (m, 3H), 4.87–4.80 (m, 1H), 3.74 (s, 3H), 3.31 (br, 1H), 3.24–3.19 (m, 2H), 2.96–2.85 (m, 2H), 2.66–2.53 (m, 4H), 2.27–2.20 (m, 2H), 2.16–2.05 (m, 2H), 1.96–1.80 (m, 2H), 1.75–1.63 (m, 4H), 1.63–1.48 (m, 2H).

Example 7(1)

(2R)-2-(4-(3-cyclopentyloxy-4-methoxyphenyl)-4-cyanopiperidin-1-yl)propanoic acid

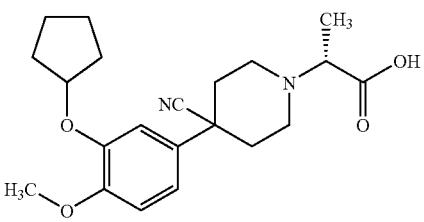

TLC: Rf 0.20 (chloroform:methanol=9:1);

NMR (CDCl$_3$): δ 7.10–7.00 (m, 2H), 6.90–6.85 (m, 1H), 4.88–4.80 (m, 1H), 3.85 (s, 3H), 3.50 (br.q, J=7.0 Hz, 1H), 3.28–3.04 (m, 3H), 3.00–2.90 (m, 1H), 2.50–2.15 (m, 5H), 2.05–1.80 (m, 6H), 1.70–1.55 (m, 2H), 1.48 (br.d, J=7.0 Hz, 3H);

[α]$_D$=+10.69(c 0.305, DMSO).

Example 7(2)

(2S)-2-(4-(3-cyclopentyloxy-4-methoxyphenyl)-4-cyanopiperidin-1-yl)propanoic acid

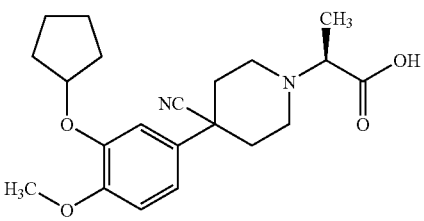

TLC: Rf 0.20 (chloroform:methanol=9:1);

NMR (CDCl$_3$): δ 7.10–7.00 (m, 2H), 6.90–6.80 (m, 1H), 4.86–4.58 (m, 1H), 3.84 (s, 3H), 3.54–3.44 (m, 1H), 3.34–3.20 (m, 2H), 3.14–3.02 (m, 1H), 3.00–2.86 (m, 1H), 2.50–1.75 (m, 11H), 1.75–1.55 (m, 2H), 1.45 (br.d, J=7.0 Hz, 3H).

[α]$_D$=−10.40 (c 0.245, DMSO).

Example 8 to Example 8(2)

The following compounds of the present invention were obtained in the same manner as in Reference Example 5→Example 3 using the compound prepared in Example 7 to Example 7(2) instead of the compound prepared in Example 2.

EXAMPLE 8

N-hydroxy-3-(4-(3-cyclopentyloxy-4-methoxyphenyl)-4-cyanopiperidin-1-yl)propanamide.hydrochloride

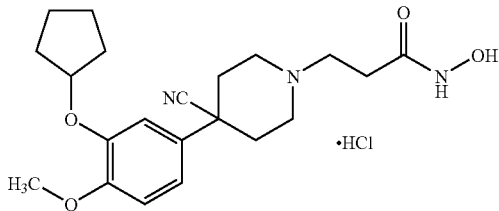

TLC: Rf 0.52 (chloroform:methanol=9:1);

NMR (pyridine-$d_5$+CDCl$_3$): δ 7.23 (d, J=2.2 Hz, 1H), 7.11 (dd, J=8.5, 2.2 Hz, 1H), 6.88 (d, J=8.5 Hz, 1H), 6.53 (br, 3H), 4.86–4.79 (m, 1H), 3.72 (s, 3H), 3.37–3.28 (m, 2H), 3.28 (t, J=7.2 Hz, 2H), 2.93–2.83 (m, 2H), 2.85 (t, J=7.2 Hz, 2H), 2.59–2.48 (m, 2H), 2.15–2.10 (m, 2H), 1.92–1.84 (m, 4H), 180–1.65 (m, 2H), 1.54–1.41 (m, 2H).

Example 8(1)

(2R)-N-hydroxy-2-(4-(3-cyclopentyloxy-4-methoxyphenyl)-4-cyanopiperidin-1-yl)propanamide.hydrochloride

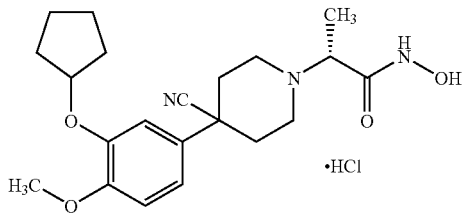

TLC: Rf 0.45 (chloroform:methanol=9:1);

NMR (pyridine-$d_5$+CDCl$_3$): δ 7.08–7.00 (m, 1H), 7.00–6.95 (m, 1H), 6.85 (d, J=8.7 Hz, 1H), 5.95–5.50 (m, 3H), 4.80–4.72 (m, 1H), 3.73 (s, 3H), 3.38–3.25 (m, 1H), 3.08–2.98 (m, 2H), 2.90–2.75 (m, 1H), 2.75–2.60 (m, 1H), 2.15–2.00 (m, 4H), 1.95–1.65 (m, 6H), 1.55–1.45 (m, 2H), 1.43 (br.d, J=6.6 Hz, 3H).

[α]$_D$=+8.76 (c 0.37, DMSO).

Example 8(2)

(2S)-N-hydroxy-2-(4-(3-cyclopentyloxy-4-methoxyphenyl)-4-cyanopiperidin-1-yl)propanamide.hydrochloride

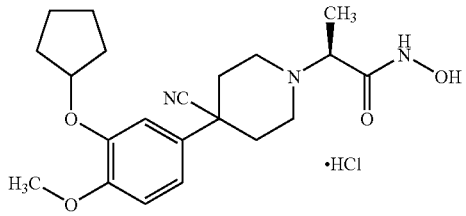

TLC: Rf 0.45 (chloroform:methanol=9:1);

NMR (pyridine-$d_5$+CDCl$_3$): δ 7.11 (d, J=2.1 Hz, 1H), 7.02 (dd, J=2.1, 8.7 Hz, 1H), 6.88 (d, J=8.7 Hz, 1H), 6.80–6.20 (m, 3H), 4.80–4.72 (m, 1H), 3.72 (s, 3H), 3.40 (br.q, J=6.9 Hz, 1H), 3.14–3.02 (m, 2H), 3.00–2.88 (m, 1H), 2.82–2.70 (m, 1H), 2.20–2.05 (m, 4H), 1.95–1.65 (m, 6H), 1.55–1.45 (m, 2H), 1.41 (d, J=6.9 Hz, 3H).

[α]$_D$=8.72 (c 0.15, DMSO).

REFERENCE EXAMPLE 6

1-(3-cyclopentyloxy-4-methoxyphenyl)cyclopent-3-encarbonitrile

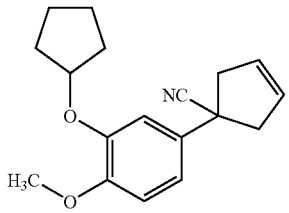

2-(3-Cyclopentyloxy-4-methoxyphenyl)ethane nitrile (4.0 g) was dissolved in tetrahydrofuran (75 ml) under argon atmosphere, and a tetrahydrofuran solution (40.4 ml) of 1.0 M lithium hexamethyldisilazane was added dropwise thereto at −78° C., followed by stirring at −78° C. for 1 hour. The reaction mixture was diluted with a saturated aqueous ammonium chloride solution, and extracted with ethyl acetate. The extract was washed with water and saturated saline in this order, dried with anhydrous magnesium sulfate, and concentrated under reduced pressure. The residue was purified by silica gel column chromatography (hexane:ethyl acetate=8:1) to thereby obtain the title compound (3.05 g) having the following physical properties.

TLC: Rf 0.39 (hexane:ethyl acetate=2:1);

NMR (CDCl$_3$): δ 7.00–6.95 (m, 2H), 6.82 (d, J=8.7 Hz, 1H), 5.82 (s, 2H), 4.78 (m, 1H), 3.84 (s, 3H), 3.35–3.20 (m, 2H), 3.00–2.85 (m, 2H), 2.00–1.75 (m, 6H), 1.70–1.55 (m, 2H).

REFERENCE EXAMPLE 7

2-(3-cyclopentyloxy-4-methoxyphenyl)-4-oxo-2-(2-oxoethyl)butanenitrile

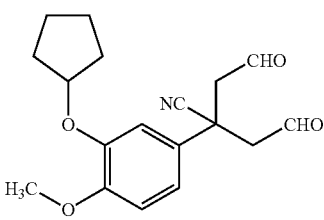

The compound (460 mg) prepared in Reference Example 6 was dissolved in methylene chloride (10 ml), ozone was blown therein at −78° C. for 25 minutes, and triphenylphosphine (513 mg) was added thereto, followed by stirring at −78° C. for 30 minutes. The reaction mixture was stirred at room temperature for 1 hour, and concentrated under reduced pressure to obtain the title compound (1.27 g). The resulting compound was used without purification in the subsequent reaction.

EXAMPLE 9

2-(4-(3-cyclopentyloxy-4-methoxyphenyl)-4-cyanopiperidin-1-yl)-2-methylpropanoic acid.benzyl ester

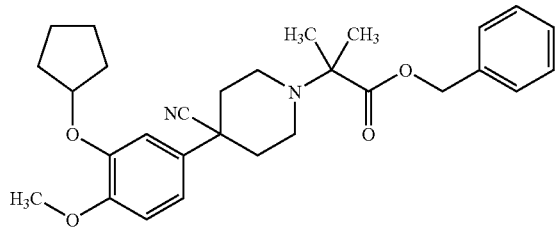

To a dichloroethane (10 ml) solution of the compound (1.27 g) prepared in Reference Example 7 and 2-amino-2-methylpropanoic acid.benzyl ester (374 mg), sodium triacetoxyborohydride (1.03 g) and acetic acid (0.56 ml) were added in this order, followed by stirring at room temperature for 3 hours. The reaction mixture was diluted with ethyl acetate, washed with a saturated aqueous sodium hydrogen carbonate solution and saturated saline in this order, dried with anhydrous sodium sulfonate, and concentrated under reduced pressure. The residue was purified by silica gel column chromatography (hexane:ethyl acetate=4:1) to thereby obtain the compound of the present invention (196 mg) having the following physical properties.

TLC: Rf 0.62 (hexane:ethyl acetate=2:1);

NMR (CDCl$_3$): δ 7.45–7.30 (m, 5H), 7.05–6.95 (m, 2H), 6.85 (d, J=9.0 Hz, 1H), 5.19 (s, 2H), 4.80 (m, 1H), 3.84 (s, 3H), 3.05–2.95 (m, 2H), 2.80–2.60 (m, 2H), 2.10–2.00 (m, 4H), 2.05–1.80 (m, 6H), 1.80–1.50 (m, 2H), 1.38 (s, 6H).

Example 10 to Example 10(2)

The compounds of the present invention were obtained in the same manner as in Reference Example 6→Reference Example 7→Example 9 using 2-(3-cyclopentyloxy-4-methoxyphenyl)ethane nitrile or a corresponding nitrile derivative and 1-aminocyclopropanecarboxylic acid.benzyl ester instead of 2-amino-2-methylpropanoic acid.benzyl ester.

EXAMPLE 10

1-(4-(3-cyclopentyloxy-4-methoxyphenyl)-4-cyanopiperidin-1-yl)cyclopropanecarboxylic acid.benzyl ester

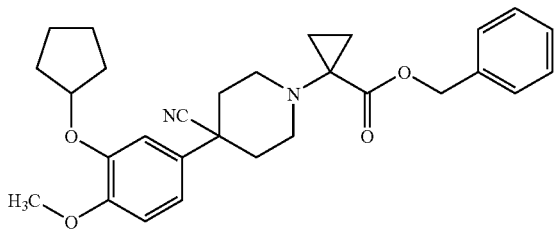

TLC: Rf 0.50 (hexane:ethyl acetate=2:1);
NMR (CDCl$_3$): δ 7.50–7.30 (m, 5H), 7.00 (d, J=2.1 Hz, 1H), 6.98 (dd, J=9.0, 2.1 Hz, 1H), 6.84 (d, J=9.0 Hz, 1H), 5.19 (s, 2H), 4.80 (m, 1H), 3.84 (s, 3H), 3.65–3.50 (m, 2H), 3.00–2.90 (m, 2H), 2.10–2.00 (m, 2H), 2.00–1.75 (m, 8H), 1.70–1.55 (m, 2H), 1.40–1.35 (m, 2H), 1.00–0.95 (m, 2H).

Example 10(1)

1-(4-(3-ethoxy-4-methoxyphenyl-4-cyanopiperidin-1-yl)cyclopropanecarboxylic acid.benzyl ester

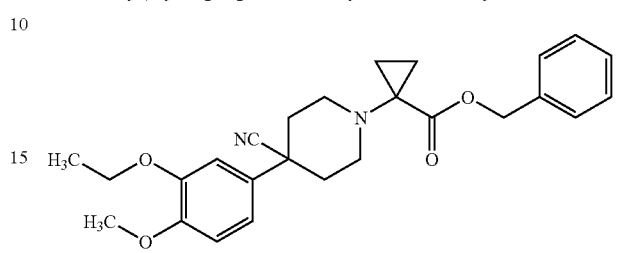

TLC: Rf 0.48 (ethyl acetate:hexane=1:3);

NMR (CDCl$_3$): δ 7.45–7.28 (m, 5H), 7.02–6.97 (m, 2H), 6.85 (d, J=9.0 Hz, 1H), 5.20 (s, 2H), 4.12 (q, J=7.0 Hz, 2H), 3.87 (s, 3H), 3.62–3.51 (m, 2H), 3.00–2.91 (m, 2H), 2.08–2.00 (m, 2H), 1.90–1.79 (m, 2H), 1.47 (t, J=7.0 Hz, 3H), 1.38–1.34 (m, 2H), 0.99–0.94 (m, 2H).

Example 10(2)

1-(4-(3-methoxymethoxy-4-methoxyphenyl)-4-cyanopiperidin-1-yl)cyclopropanecarboxylic acid.benzyl ester

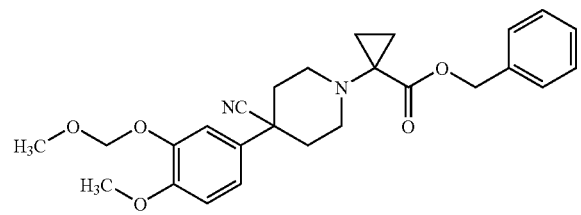

TLC: Rf 0.45 (ethyl acetate:hexane=1:2);

NMR (CDCl$_3$): δ 7.45–7.29 (m, 5H), 7.22 (d, J=2.4 Hz, 1H), 7.14 (dd, J=8.4 Hz, 2.4 Hz, 1H), 6.88 (d, J=8.4 Hz, 1H), 5.23 (s, 2H), 5.19 (s, 2H), 3.88 (s, 3H), 3.61–3.50 (m, 2H), 3.53 (s, 3H), 3.00–2.92 (m, 2H), 2.08–2.00 (m, 2H), 1.89–1.78 (m, 2H), 1.38–1.34 (m, 2H), 1.00–0.95 (m, 2H).

EXAMPLE 11

1-(4-(3-hydroxy-4-methoxyphenyl)-4-cyanopiperidin-1-yl)cyclopropanecarboxylic acid.benzyl ester.hydrochloride

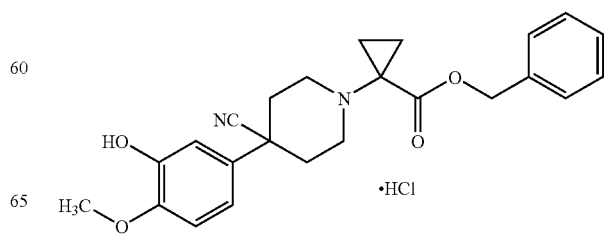

To a methylene chloride (10 ml) solution of the compound (1.8 g) prepared in Example 10(2), a 4 N hydrogen chloride—ethyl acetate solution (10 ml) was added, followed by stirring at room temperature for 1 hour. The reaction mixture was concentrated under reduced pressure. The residue was washed with ethyl acetate to thereby obtain the compound of the present invention (1.51 g) having the following properties.

TLC: Rf 0.38 (ethyl acetate:hexane=1:2);

NMR (CDCl₃): δ 7.42–7.32 (m, 5H), 7.19 (d, J=2.7 Hz, 1H), 7.07 (dd, J=8.4 Hz, 2.7 Hz, 1H), 6.86 (d, J=8.4 Hz, 1H), 5.90–5.83 (bs, 1H), 5.22 (s, 2H), 4.50–4.36 (m, 2H), 3.89 (s, 3H), 3.56–3.47 (m, 2H), 3.27–3.09 (m, 2H), 2.30–2.23 (m, 2H), 2.22–2.12 (m, 2H), 1.72–1.65 (m, 2H), 1.70–1.50 (br, 1H).

EXAMPLE 12

1-(4-(3-cyclopropylmethoxy-4-methoxyphenyl)-4-cyanopiperidin-1-yl)cyclopropanecarboxylic acid-.benzyl ester

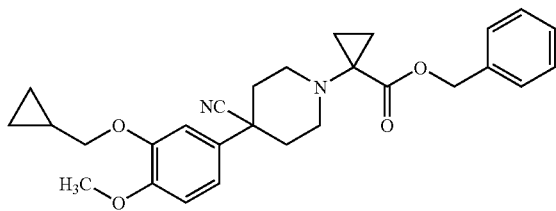

To a dimethylformamide (5 ml) solution of the compound (664 mg) prepared in Example 11, cyclopropylmethylbromide (0.22 ml) and potassium carbonate (518 mg) were added in this order at room temperature, followed by stirring at room temperature overnight. The reaction mixture was poured into iced water, and extracted with ethyl acetate. The extract was washed with 1 N hydrochloric acid, a saturated aqueous sodium hydrogen carbonate solution and saturated saline in this order, dried with anhydrous sodium sulfate, and concentrated under reduced pressure. The residue was purified by silica gel column chromatography (hexane:ethyl acetate=2:1) to thereby obtain the compound of the present invention (763 mg) having the following physical properties.

TLC: Rf 0.57 (ethyl acetate:hexane=1:2);

NMR (CDCl₃): δ 7.45–7.28 (m, 5H), 7.02–6.96 (m, 2H), 6.87–6.82 (m, 1H), 5.19 (s, 2H), 3.88–3.84 (m, 5H), 3.61–3.49 (m, 2H), 3.00–2.90 (m, 2H), 2.08–1.99 (m, 2H), 1.90–1.77 (m, 2H), 1.38–1.32 (m, 2H), 0.98–0.96 (m, 2H), 0.69–0.61 (m, 2H), 0.40–0.33 (m, 3H).

EXAMPLE 13

1-(4-(3-cyclobutyloxy-4-methoxyphenyl)-4-cyanopiperidin-1-yl)cyclopropanecarboxylic acid.benzyl ester

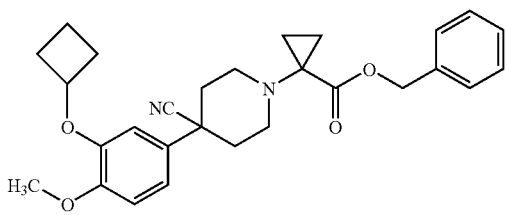

To a tetrahydrofuran (5 ml) suspension of the compound (664 mg) prepared in Example 11, triethylamine (0.21 ml), cyclobutanol (0.18 ml), triphenylphosphine (787 mg) and diethyl dicarboxylate (0.47 ml) were added at room temperature, followed by stirring at room temperature overnight. The reaction mixture was purified by silica gel column chromatography (hexane:ethyl acetate=7:2) to thereby obtain the compound of the present invention (683 mg) having the following physical properties.

TLC: Rf 0.52 (ethyl acetate:hexane=1:2);

NMR (CDCl₃): δ 7.45–7.29 (m, 5H), 6.97 (dd, J=8.4 Hz, 2.4 Hz, 1H), 6.87 (d, J=2.4 Hz, 1H), 6.84 (d, J=8.4 Hz, 1H), 5.19 (s, 2H), 4.69 (quint, J=7.0 Hz, 1H), 3.86 (s, 3H), 3.61–3.50 (m, 2H), 3.00–2.90 (m, 2H), 2.55–2.43 (m, 2H), 2.33–2.18 (m, 2H), 2.08–1.99 (m, 2H), 1.89–1.60 (m, 4H), 1.38–1.34 (m, 2H), 0.99–0.94 (m, 2H).

EXAMPLE 14

2-(4-(3-cyclopentyloxy-4-methoxyphenyl)-4-cyanopiperidin-1-yl)-2-methylpropanoic acid

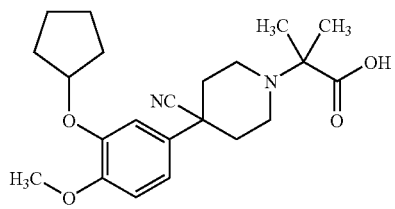

The compound (180 mg) prepared in Example 9 was dissolved in methanol (4 ml) and tetrahydrofuran (4 ml), 10% palladium-carbon (20 mg) was added thereto, and the mixture was stirred under hydrogen gas atmosphere at room temperature for 1.5 hours. The reaction mixture was filtered with celite, and the filtrate was concentrated. The residue was purified by silica gel column chromatography (chloroform:methanol:water=10:2:0.1) to thereby obtain the compound of the present invention (140 mg) having the following physical properties.

TLC: Rf 0.34 (chloroform:methanol=10:1);

NMR (DMSO-d₆): δ 7.05–6.90 (m, 3H), 4.84 (m, 1H), 3.74 (s, 3H), 3.80–3.00 (br, 1H), 3.15–3.00 (m, 2H), 2.65–2.50 (m, 2H), 2.20–2.05 (m, 2H), 2.10–1.95 (m, 2H), 2.00–1.80 (m, 2H), 1.80–1.60 (m, 4H), 1.65–1.55 (m, 2H), 1.25 (s, 6H).

Example 14(1) to Example 14(4)

The following compounds of the present invention were obtained in the same manner as in Example 14 using the compound prepared in Example 10, Example 10(1), Example 12 or Example 13 instead of the compound prepared in Example 9.

Example 14(1)

1-(4-(3-cyclopentyloxy-4-methoxyphenyl)-4-cyan-opiperidin-1-yl)cyclopropanecarboxylic acid

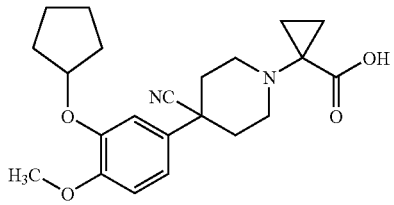

TLC: Rf 0.45 (chloroform:methanol=10:1);

NMR (DMSO-d$_6$): δ 12.29 (brs, 1H), 7.05–6.90 (m, 3H), 4.82 (m, 1H), 3.73 (s, 3H), 3.45–3.30 (m, 2H), 2.95–2.85 (m, 2H), 2.10–1.95 (m, 2H), 2.00–1.60 (m, 8H), 1.65–1.50 (m, 2H), 1.25–1.10 (m, 2H), 0.95–0.80 (m, 2H).

Example 14(2)

1-(4-(3-ethoxy-4-methoxyphenyl-4-cyanopiperidin-1-yl)cyclopropanecarboxylic acid

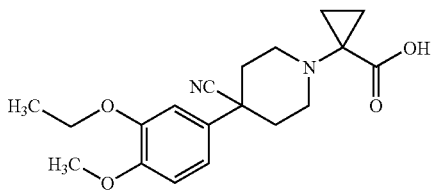

TLC: Rf 0.38 (dichloromethane:methanol=9:1);

NMR (DMSO-d$_6$): δ 12.45–12.15 (br, 1H), 7.03–6.93 (m, 3H), 4.04 (q, J=6.9 HZ, 2H), 3.75 (s, 3H), 3.45–3.35 (m, 2H), 2.95–2.86 (m, 2H), 2.09–1.98 (m, 2H), 1.86–1.72 (m, 2H), 1.32 (t, J=6.9 Hz, 3H), 1.21–1.16 (m, 2H), 0.92–0.86 (m, 2H).

Example 14(3)

1-(4-(3-cyclopropylmethoxy-4-methoxyphenyl)-4-cyanopiperidin-1-yl)cyclopropanecarboxylic acid

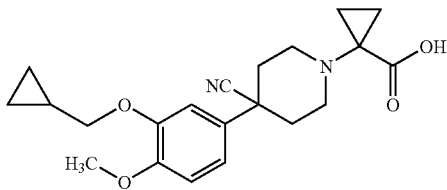

TLC: Rf 0.35 (ethyl acetate:hexane=1:1);

NMR (DMSO-d$_6$): δ 12.5–12.0 (br, 1H), 7.04–6.93 (m, 3H), 3.82 (d, J=7.2 HZ, 2H), 3.77 (s, 3H), 3.46–3.36 (m, 2H), 2.94–2.86 (m, 2H), 2.07–1.97 (m, 2H), 1.85–1.71 (m, 2H), 1.26–1.14 (m, 3H), 0.91–0.85 (m, 2H), 0.60–0.53 (m, 2H), 0.35–0.28 (m, 2H).

Example 14(4)

1-(4-(3-cyclobutyloxy-4-methoxyphenyl)-4-cyanopiperidin-1-yl)cyclopropanecarboxylic acid

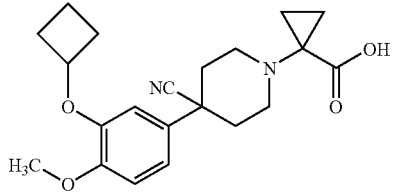

TLC: Rf 0.36 (dichloromethane:methanol=19:1);

NMR (DMSO-d$_6$): δ 12.5–12.1 (br, 1H), 7.01–6.93 (m, 2H), 6.84 (d, J=1.8 Hz, 1H), 4.73 (quint, J=7.5 HZ, 1H), 3.75 (s, 3H), 3.44–3.36 (m, 2H), 2.95–2.86 (m, 2H), 2.46–2.33 (m, 2H), 2.11–1.96 (m, 4H), 1.83–1.55 (m, 4H), 1.21–1.15 (m, 2H), 0.92–0.86 (m, 2H).

Example 15 to Example 15(4)

The following compounds of the present invention were obtained in the same manner as in Reference Example 5→Example 3 using the compound prepared in Example 14 to Example 14(4) instead of the compound prepared in Example 2.

EXAMPLE 15

N-hydroxy-2-(4-(3-cyclopentyloxy-4-methoxyphenyl)-4-cyanopiperidin-1-yl)-2-methylpropanamide.hydrochloride

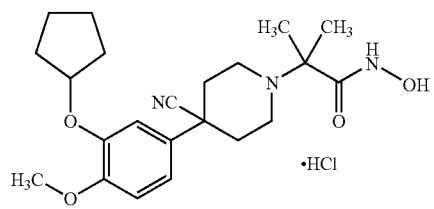

TLC: Rf 0.38 (chloroform:methanol=10:1);

NMR (pyridine-d$_5$+CDCl$_3$): δ 7.14 (d, J=2.1 Hz, 1H), 6.99 (dd, J=8.4, 2.1 Hz, 1H), 6.91 (d, J=8.4 Hz, 1H), 5.95 (br.s, 3H), 4.72 (m, 1H), 3.73 (s, 3H), 3.10–3.00 (m, 2H), 2.80–2.65 (m, 2H), 2.20–2.00 (m, 4H), 2.00–1.70 (m, 6H), 1.60–1.40 (m, 2H), 1.39 (s, 6H).

Example 15(1)

N-hydroxy-1-(4-(3-cyclopentyloxy-4-methoxyphenyl)-4-cyanopiperidin-1-yl)cyclopropanecarboxamide.hydrochloride

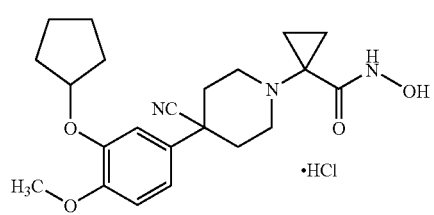

TLC: Rf 0.45 (chloroform:methanol=10:1);

NMR (pyridine-$d_5$+CDCl$_3$): δ 7.12 (d, J=2.4 Hz, 1H), 6.99 (dd, J=8.4, 2.4 Hz, 1H), 6.87 (d, J=8.4 Hz, 1H), 6.90–6.00 (br, 3H), 4.75 (m, 1H), 3.73 (s, 3H), 3.00–2.90 (m, 2H), 2.90–2.70 (m, 2H), 2.20–2.00 (m, 4H), 2.00–1.60 (m, 6H), 1.60–1.40 (m, 2H), 1.35–1.25 (m, 2H), 1.10–1.00 (m, 2H).

Example 15(2)

N-hydroxy-1-(4-(3-ethoxy-4-methoxyphenyl-4-cyanopiperidin-1-yl)cyclopropanecarboxamide.hydrochloride

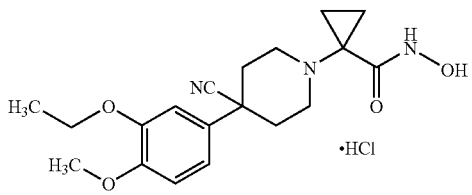

TLC: Rf 0.42 (dichloromethane:methanol=9:1);
NMR (pyridine-$d_5$+CDCl$_3$): δ 8.00–7.20 (br, 3H), 7.09 (d, J=1.8 Hz, 1H), 7.04 (dd, J=8.4, 1.8 Hz, 1H), 6.89 (d, J=8.4 Hz, 1H), 3.91 (q, J=6.9 HZ, 2H), 3.74 (s, 3H), 2.99–2.79 (m, 4H), 2.19–2.10 (m, 4H), 1.37–1.27 (m, 5H), 1.09–1.03 (m, 2H).

Example 15(3)

N-hydroxy-1-(4-(3-cyclopropylmethoxy-4-methoxyphenyl)-4-cyanopiperidin-1-yl)cyclopropanecarboxamide.hydrochloride

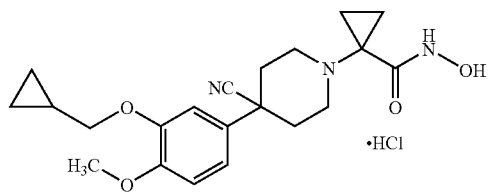

TLC: Rf 0.60 (dichloromethane:methanol=9:1);
NMR (pyridine-$d_5$+CDCl$_3$): δ 8.60–6.80 (br, 3H), 7.15 (d, J=2.0 Hz, 1H), 7.05 (dd, J=9.0, 2.0 Hz, 1H), 6.91 (d, J=9.0 Hz, 1H), 3.81 (d, J=6.9 HZ, 2H), 3.73 (s, 3H), 2.99–2.79 (m, 4H), 2.20–2.02 (m, 4H), 1.37–1.31 (m, 2H), 1.3–1.20 (m, 1H), 1.08–1.03 (m, 2H), 0.55–0.47 (m, 2H), 0.32–0.26 (m, 2H).

Example 15(4)

N-hydroxy-1-(4-(3-cyclobutyloxy-4-methoxyphenyl)-4-cyanopiperidin-1-yl)cyclopropanecarboxamide.hydrochloride

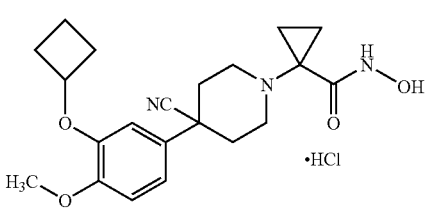

TLC: Rf 0.64 (dichloromethane:methanol=9:1);

NMR (pyridine-$d_5$+CDCl$_3$): δ 8.00–7.10 (br, 3H), 7.04 (d, J=2.1 Hz, 1H), 7.00 (dd, J=8.4, 2.1 Hz, 1H), 6.90 (d, J=8.4 Hz, 1H), 4.62 (quint, J=7.5 HZ, 1H), 3.75 (s, 3H), 3.00–2.80 (m, 4H), 2.42–2.30 (m, 2H), 2.23–2.02 (m, 6H), 1.74–1.60 (m, 1H), 1.58–1.40 (m, 1H), 1.38–1.32 (m, 2H), 1.09–1.03 (m, 2H).

Example 16 to Example 16(1)

The following compounds of the present invention were obtained in the same manner as in Reference Example 6→Reference Example 7→Example 9 using a corresponding nitrile derivative instead of 2-(3-cyclopentyloxy-4-methoxyphenyl)ethane nitrile and using a corresponding derivative instead of 2-amino-2methylpropanoic acid.benzyl ester.

EXAMPLE 16

2-(4-(3-benzyloxy-4-methoxyphenyl)-4-cyanopiperidin-1-yl)acetic acid.ethyl ester

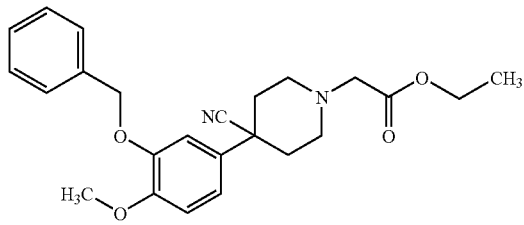

TLC: Rf 0.31 (hexane:ethyl acetate=2:1);
NMR (CDCl$_3$): δ 7.50–7.40 (m, 2H), 7.45–7.25 (m, 3H), 7.10–7.00 (m, 2H), 6.89 (d, J=8.7 Hz, 1H), 5.15 (s, 2H), 4.22 (q, J=7.2 Hz, 2H), 3.88 (s, 3H), 3.30 (s, 2H), 3.15–3.00 (m, 2H), 2.70–2.55 (m, 2H), 2.20–2.05 (m, 2H), 2.15–1.95 (m, 2H), 1.30 (t, J=7.2 Hz, 3H).

Example 16(1)

2-(4-(3-benzyloxy-4-difluoromethoxyphenyl)-4-cyanopiperidin-1-yl)acetic acid.methyl ester

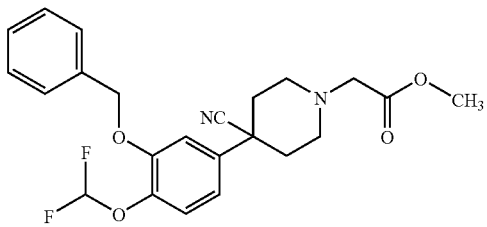

TLC: Rf 0.31 (hexane:ethyl acetate=1:1);
NMR (CDCl$_3$): δ 7.42–7.30 (m, 5H), 7.20 (d, J=8.1 Hz, 1H), 7.18 (d, J=2.4 Hz, 1H), 7.07 (dd, J=8.1, 2.4 Hz, 1H), 6.58 (t, J=75.0 Hz, 1H), 5.15 (s, 2H), 3.76 (s, 3H), 3.32 (s, 2H), 3.08 (dt, J=12.0, 2.7 Hz, 2H), 2.66 (td, J=12.0, 2.7 Hz, 2H), 2.18 (td, J=12.0, 3.9 Hz, 2H), 2.09–2.01 (m, 2H).

Example 17 to Example 17(1)

The following compounds of the present invention were obtained in the same manner as in Example 14 using the compound prepared in Example 16 or Example 16(1) instead of the compound prepared in Example 9.

EXAMPLE 17

2-(4-(3-hydroxy-4-methoxyphenyl)-4-cyanopiperidin-1-yl)acetic acid.ethyl ester

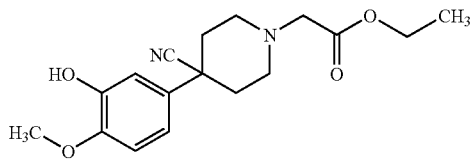

TLC: Rf 0.43 (hexane:ethyl acetate=1:2);
NMR (CDCl₃): δ 7.06 (d, J=2.4 Hz, 1H), 7.00 (dd, J=8.1, 2.4 Hz, 1H), 6.85 (d, J=8.1 Hz, 1H), 5.66 (br, 1H), 4.22 (q, J=7.2 Hz, 2H), 3.90 (s, 3H), 3.30 (s, 2H), 3.11–3.03 (m, 2H), 2.72–2.62 (m, 2H), 2.20–2.04 (m, 4H), 1.30 (t, J=7.2 Hz, 3H).

Example 17(1)

2-(4-(3-hydroxy-4-difluoromethoxyphenyl)-4-cyanopiperidin-1-yl)acetic acid.methyl ester

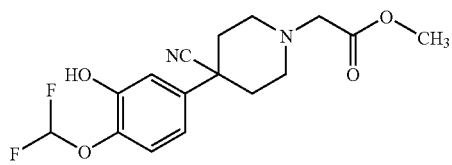

TLC: Rf 0.55 (chloroform:methanol=9:1);
NMR (CDCl₃): δ 7.16 (d, J=2.4 Hz, 1H), 7.13 (d, J=8.4 Hz, 1H), 7.02 (dd, J=8.4, 2.4 Hz, 1H), 6.54 (t, J=73.5 Hz, 1H), 3.76 (s, 3H), 3.32 (s, 2H), 3.07 (d, J=12.0 Hz, 2H), 2.66 (td, J=12.0, 2.7 Hz, 2H), 2.16 (td, J=13.5, 3.9 Hz, 2H), 2.12–2.03 (m, 3H).

Example 18 to Example 18(2)

The following compounds of the present invention were obtained in the same manner as in Example 13 using the compound prepared in Example 17 or Example 17(1) instead of the compound prepared in Example 11 and using cyclobutyl alcohol or corresponding alcohol.

EXAMPLE 18

2-(4-(3-(indan-2-yloxy)-4-methoxyphenyl)-4-cyanopiperidin-1-yl)acetic acid.ethyl ester

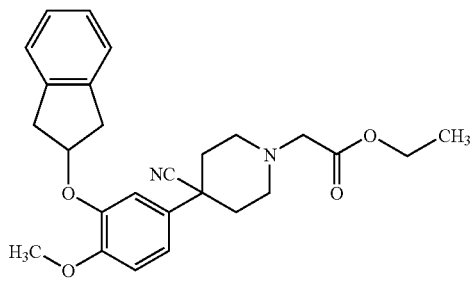

TLC: Rf 0.62 (hexane:ethyl acetate=1:2);

NMR (CDCl₃): δ 7.26–7.16 (m, 4H), 7.09–7.05 (m, 2H), 6.90–6.86 (m, 1H), 5.20 (m, 1H), 4.22 (q, J=7.2 Hz, 2H), 3.82 (s, 3H), 3.44–3.35 (m, 2H), 3.31 (s, 2H), 3.27–3.19 (m, 2H), 3.14–3.05 (m, 2H), 2.73–2.63 (m, 2H), 2.26–2.16 (m, 2H), 2.15–2.06 (m, 2H), 1.30 (t, J=7.2 Hz, 3H).

Example 18(1)

2-(4-(3-cyclobutyloxy-4-difluoromethoxyphenyl)-4-cyanopiperidin-1-yl)acetic acid.methyl ester

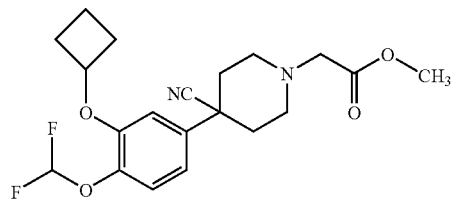

TLC: Rf 0.54 (ethyl acetate:toluene=1:1);
NMR (CDCl₃): δ 7.17 (d, J=8.1 Hz, 1H), 7.02 (dd, J=8.1, 2.1 Hz, 1H), 6.97 (d, J=2.1 Hz, 1H), 6.58 (t, J=75.0 Hz, 1H), 4.69 (m, 1H), 3.76 (s, 3H), 3.33 (s, 2H), 3.09 (dt, J=12.3, 2.7 Hz, 2H), 2.66 (td, J=12.3, 2.7 Hz, 2H), 2.54–2.43 (m, 2H), 2.29–2.13 (m, 4H), 2.11–2.02 (m, 2H), 1.89 (m, 1H), 1.72 (m, 1H).

Example 18(2)

2-(4-(3-(indan-2-yloxy)-4-difluoromethoxyphenyl)-4-cyanopiperidin-1-yl)acetic acid.methyl ester

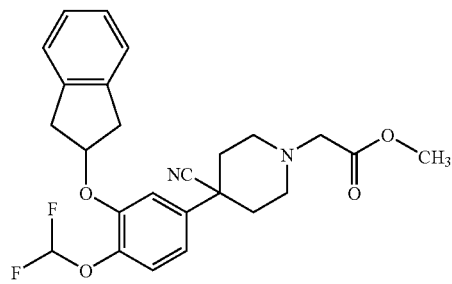

TLC: Rf 0.29 (hexane:ethyl acetate=1:1);
NMR (CDCl₃): δ 7.27–7.16 (m, 6H), 7.07 (dd, J=8.1, 2.4 Hz, 1H), 6.38 (t, J=75.3 Hz, 1H), 5.26–5.20 (m, 1H), 3.76 (s, 3H), 3.41 (dd, J=16.5, 6.3 Hz, 2H), 3.34 (s, 2H), 3.20 (dd, J=16.5, 3.3 Hz, 2H), 3.11 (d, J=12.0 Hz, 2H), 2.69 (dt, J=12.0, 2.4 Hz, 2H), 2.28–2.19 (m, 2H), 2.14–2.04 (m, 2H).

Example 19 to Example 19(5)

The following compounds of the present invention were obtained in the same manner as in Example 12 using the compound prepared in Example 17(1) instead of the compound prepared in Example 11 and using cyclopropylmethyl bromide or a corresponding halogen derivative.

EXAMPLE 19

2-(4-(3-cyclopropylmethoxy-4-difluromethoxyphenyl)-4-cyanopiperidin-1-yl)acetic acid.methyl ester

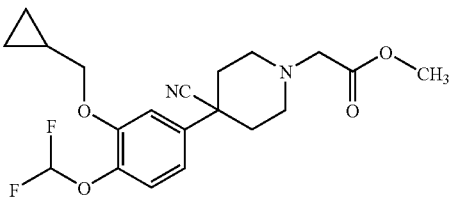

TLC: Rf 0.80 (chloroform:methanol=9:1);

NMR (CDCl$_3$): δ 7.18 (d, J=8.1 Hz, 1H), 7.09–7.03 (m, 2H), 6.63 (t, J=75.6 Hz, 1H), 3.88 (d, J=6.9 Hz, 2H), 3.76 (s, 3H), 3.32 (s, 2H), 3.08 (dt, J=12.0, 2.7 Hz, 2H), 2.66 (td, J=12.0, 2.7 Hz, 2H), 2.27–2.15 (m, 2H), 2.12–2.05 (m, 2H), 1.28 (m, 1H), 0.69–0.63 (m, 2H), 0.40–0.33 (m, 2H).

Example 19(1)

2-(4-(3-cyclobutylmethoxy-4-difluromethoxyphenyl)-4-cyanopiperidin-1-yl)acetic acid.methyl ester

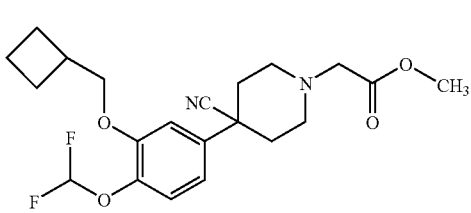

TLC: Rf 0.84 (chloroform:methanol=9:1);

NMR (CDCl$_3$): δ 7.17 (d, J=8.4 Hz, 1H), 7.09 (d, J=2.1 Hz, 1H), 7.05 (dd, J=8.4, 2.1 Hz, 1H), 6.57 (t, J=75.3 Hz, 1H), 3.99 (d, J=6.6 Hz, 2H), 3.76 (s, 3H), 3.33 (s, 2H), 3.09 (dt, J=11.7, 2.4 Hz, 2H), 2.81 (m, 1H), 2.67 (td, J=11.7, 2.4 Hz, 2H), 2.28–1.82 (m, 10H).

Example 19(2)

2-(4-(3-ethoxy-4-difluromethoxyphenyl)-4-cyanopiperidin-1-yl)acetic acid.methyl ester

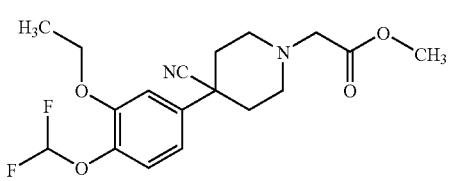

TLC: Rf 0.33 (hexane:ethyl acetate=1:2);

NMR (CDCl$_3$): δ 7.17 (d, J=8.4 Hz, 1H), 7.09 (d, J=2.1 Hz, 1H), 7.04 (dd, J=8.4, 2.1 Hz, 1H), 6.57 (t, J=75.3 Hz, 1H), 4.11 (q, J=6.9 Hz, 2H), 3.75 (s, 3H), 3.32 (s, 2H), 3.08 (d, J=12.0 Hz, 2H), 2.66 (dt, J=12.0, 2.7 Hz, 2H), 2.26–2.16 (m, 2H), 2.10–2.05 (m, 2H), 1.46 (t, J=6.9 Hz, 3H).

Example 19(3)

2-(4-(3-butoxy-4-difluromethoxyphenyl)-4-cyanopiperidin-1-yl)acetic acid.methyl ester

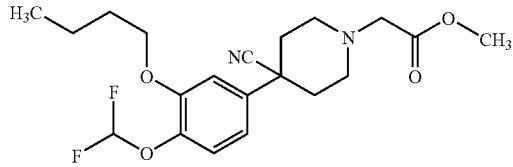

TLC: Rf 0.57 (hexane:ethyl acetate=1:1);

NMR (CDCl$_3$): δ 7.17 (d, J=8.5 Hz, 1H), 7.09 (d, J=2.2 Hz, 1H), 7.05 (dd, J=8.5, 2.2 Hz, 1H), 6.56 (t, J=75.0 Hz, 1H), 4.03 (t, J=6.5 Hz, 2H), 3.76 (s, 3H), 3.33 (s, 2H), 3.13–3.05 (m, 2H), 2.72–2.62 (m, 2H), 2.27–2.17 (m, 2H), 2.11–2.04 (m, 2H), 1.86–1.76 (m, 2H), 1.60–1.45 (m, 2H), 0.99 (t, J=7.4 Hz, 3H).

Example 19(4)

2-(4-(3-propoxy-4-difluromethoxyphenyl)-4-cyanopiperidin-1-yl)acetic acid.methyl ester

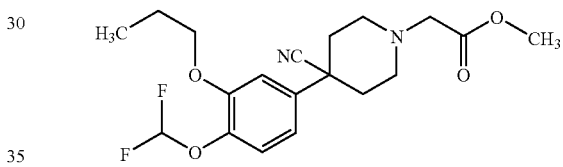

TLC: Rf 0.56 (hexane:ethyl acetate=1:1);

NMR (CDCl$_3$): δ 7.18 (d, J=8.1 Hz, 1H), 7.10 (d, J=2.4 Hz, 1H), 7.05 (dd, J=8.1, 2.4 Hz, 1H), 6.57 (t, J=75.0 Hz, 1H), 3.99 (t, J=7.0 Hz, 2H), 3.76 (s, 3H), 3.33 (s, 2H), 3.15–3.00 (m, 2H), 2.75–2.60 (m, 2H), 2.30–2.15 (m, 2H), 2.15–2.00 (m, 2H), 1.86 (sext, J=7.0 Hz, 2H), 1.06 (t, J=7.0 Hz, 3H).

Example 19(5)

2-(4-(3-(2-methylpropoxy)-4-difluromethoxyphenyl)-4-cyanopiperidin-1-yl)acetic acid.methyl ester

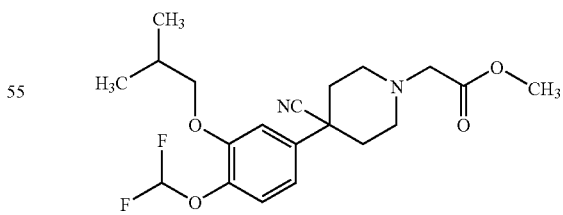

TLC: Rf 0.40 (hexane:ethyl acetate=1:1);

NMR (CDCl$_3$): δ 7.18 (d, J=7.8 Hz, 1H), 7.10–7.00 (m, 2H), 6.56 (t, J=75.3 Hz, 1H), 3.78 (d, J=6.6 Hz, 2H), 3.76 (s, 3H), 3.33 (s, 2H), 3.20–3.00 (m, 2H), 2.80–2.60 (m, 2H), 2.30–2.15 (m, 2H), 2.25–2.00 (m, 1H), 2.20–2.00 (m, 2H), 1.05 (d, J=6.6 Hz, 6H).

Example 20 to Example 20(8)

The following compounds of the present invention were obtained in the same manner as in Example 2 using the compound prepared in Example 18 to Example 18(2) or Example 19 to Example 19(5) instead of the compound prepared in Example 1.

Also, the compound in Example 20(3) was converted to hydrochloride by a known method.

EXAMPLE 20

2-(4-(3-(indan-2-yloxy)-4-methoxyphenyl)-4-cyanopiperidin-1-yl)acetic acid

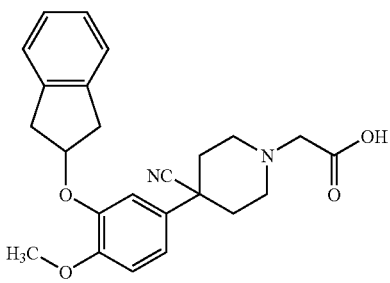

TLC: Rf 0.68 (chloroform:methanol:acetic acid=30:2:1);

NMR (DMSO-d$_6$): δ 7.28–7.23 (m, 2H), 7.19–7.13 (m, 2H), 7.10 (d, J=1.8 Hz, 1H), 7.06 (dd, J=8.6, 1.8 Hz, 1H), 6.98 (d, J=8.6 Hz, 1H), 5.28 (m, 1H), 3.69 (s, 3H), 3.80–2.60 (br, 1H), 3.39–3.30 (m, 2H), 3.25 (s, 2H), 3.16–2.98 (m, 4H), 2.66–2.53 (m, 2H), 2.15–1.97 (m, 4H).

Example 20(1)

2-(4-(3-cyclobutyloxy-4-difluoromethoxyphenyl)-4-cyanopiperidin-1-yl)acetic acid

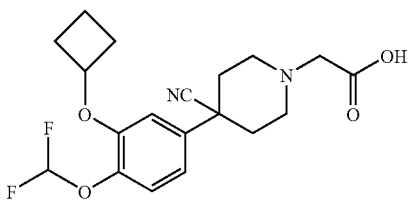

TLC: Rf 0.67 (chloroform:methanol=3:1);

NMR (DMSO-d$_6$): δ 7.21 (d, J=8.1 Hz, 1H), 7.10 (dd, J=8.1, 2.1 Hz, 1H), 7.08 (t, J=74.4 Hz, 1H), 7.06 (d, J=2.1 Hz, 1H), 4.85 (m, 1H), 4.25–2.60 (br.s, 1H), 3.24 (s, 2H), 3.01 (br.d, J=12.0 Hz, 2H), 2.58 (br.t, J=12.0 Hz, 2H), 2.48–2.34 (m, 2H), 2.16–1.94 (m, 6H), 1.77 (m, 1H), 1.62 (m, 1H).

Example 20(2)

2-(4-(3-(indan-2-yloxy)-4-difluoromethoxyphenyl)-4-cyanopiperidin-1-yl)acetic acid

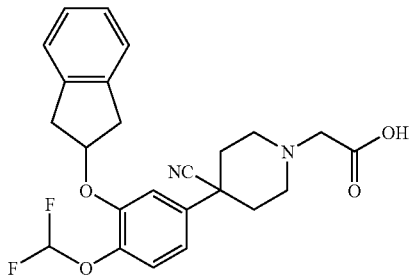

TLC: Rf 0.24 (chloroform:methanol:acetic acid=9:1:0.1);

NMR (DMSO-d$_6$): δ 7.32–7.14 (m, 7H), 6.91 (t, J=74.4 Hz, 1H), 5.43–5.37 (m, 1H), 4.00–2.60 (br, 1H), 3.39 (dd, J=16.8, 6.0 Hz, 2H), 3.24 (s, 2H), 3.07–3.00 (m, 4H), 2.60 (dt, J=11.7, 3.0 Hz, 2H), 2.17–2.03 (m, 4H).

Example 20(3)

2-(4-(3-cyclopropylmethoxy-4-difluromethoxyphenyl)-4-cyanopiperidin-1-yl)acetic acid.hydrochloride

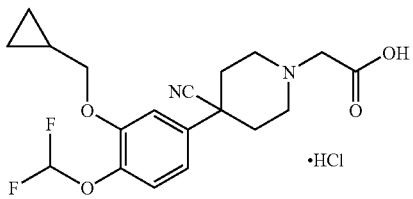

TLC: Rf 0.61 (chloroform:methanol=2:1);

NMR (DMSO-d$_6$): δ 7.21–7.14 (m, 2H), 7.02 (t, J=74.4 Hz, 1H), 7.01 (dd, J=8.7, 2.1 Hz, 1H), 4.12 (s, 2H), 3.95–2.95 (br.s, 2H), 3.85 (d, J=6.9 Hz, 2H), 3.58 (br.d, J=12.0 Hz, 2H), 3.23 (br.t, J=12.0 Hz, 2H), 2.54–2.31 (m, 4H), 1.14 (m, 1H), 0.47 (m, 2H), 0.24 (m, 2H).

Example 20(4)

2-(4-(3-cyclobutylmethoxy-4-difluromethoxyphenyl)-4-cyanopiperidin-1-yl)acetic acid

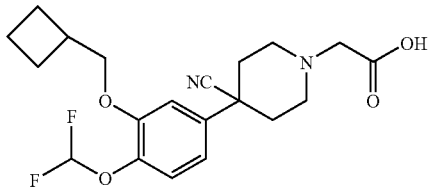

TLC: Rf 0.53 (chloroform:methanol=3:1);

NMR (DMSO-d$_6$): δ 7.25 (d, J=2.4 Hz, 1H), 7.21 (d, J=8.4 Hz, 1H), 7.11 (dd, J=8.4, 2.4 Hz, 1H), 7.03 (t, J=74.4 Hz, 1H), 4.06 (d, J=6.6 Hz, 2H), 4.00–2.80 (br.s, 1H), 3.24 (s, 2H), 3.02 (br.d, J=12.0 Hz, 2H), 2.72 (m, 1H), 2.59 (td, J=12.0, 2.7 Hz, 2H), 2.17–1.95 (m, 6H), 2.00–1.75 (m, 4H).

Example 20(5)

2-(4-(3-ethoxy-4-difluromethoxyphenyl)-4-cyanopiperidin-1-yl)acetic acid

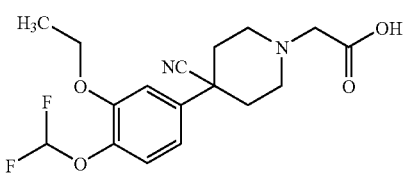

TLC: Rf 0.15 (chloroform:methanol:acetic acid=9:1:0.1);

NMR (DMSO-$d_6$): δ 7.22–7.19 (m, 2H), 7.09 (dd, J=8.4, 2.1 Hz, 1H), 7.06 (t, J=74.4 Hz, 1H), 4.13 (q, J=6.9 Hz, 2H), 4.00–3.00 (br, 1H), 3.21 (s, 2H), 3.01 (d, J=12.0 Hz, 2H), 2.57 (dt, J=11.7, 3.0 Hz, 2H), 2.13–1.99 (m, 4H), 1.32 (t, J=6.9 Hz, 3H).

Example 20(6)

2-(4-(3-butoxy-4-difluromethoxyphenyl)-4-cyanopiperidin-1-yl)acetic acid

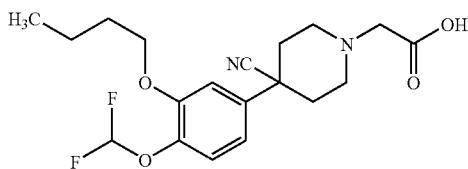

TLC: Rf 0.56 (chloroform:methanol:acetic acid=10:2:1);
NMR (CDCl$_3$+DMSO-$d_6$): δ 7.17 (d, J=8.1 Hz, 1H), 7.09 (dd, J=8.1, 2.1 Hz, 1H), 7.04 (d, J=2.1 Hz, 1H), 6.57 (t, J=75.2 Hz, 1H), 4.03 (t, J=6.5 Hz, 2H), 3.57 (br, 1H), 3.29 (s, 2H), 3.20–3.10 (m, 2H), 2.72–2.61 (m, 2H), 2.30–2.19 (m, 2H), 2.13–2.05 (m, 2H), 1.86–1.76 (m, 2H), 1.58–1.44 (m, 2H), 0.99 (t, J=7.5 Hz, 3H).

Example 20(7)

2-(4-(3-propoxy-4-difluromethoxyphenyl)-4-cyanopiperidin-1-yl)acetic acid

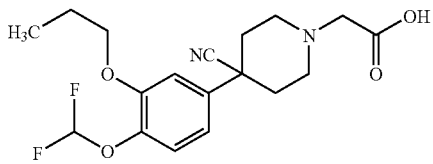

TLC: Rf 0.60 (chloroform:methanol:acetic acid 10:2:1);
NMR (DMSO-$d_6$): δ 12.40–11.00 (br, 1H), 7.30–7.15 (m, 2H), 7.11 (dd, J=8.7, 2.7 Hz, 1H), 7.05 (t, J=74.4 Hz, 1H), 4.04 (t, J=6.6 Hz, 2H), 3.23 (s, 2H), 3.10–2.95 (m, 2H), 2.70–2.50 (m, 2H), 2.20–2.00 (m, 4H), 1.74 (sext, J=6.6 Hz, 2H), 0.98 (t, J=6.6 Hz, 3H).

Example 20(8)

2-(4-(3-(2-methylpropoxy)-4-difluromethoxyphenyl)-4-cyanopiperidin-1-yl)acetic acid

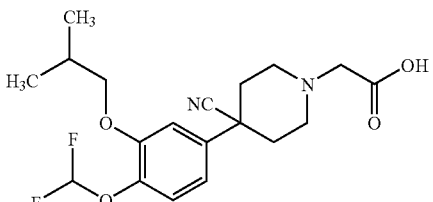

TLC: Rf 0.63 (chloroform:methanol:acetic acid=10:2:1);
NMR (DMSO-$d_6$): δ 12.20–10.80 (br, 1H), 7.25–7.20 (m, 2H), 7.11 (dd, J=8.7, 2.4 Hz, 1H), 7.04 (t, J=74.4 Hz, 1H), 3.86 (d, J=6.3 Hz, 2H), 3.23 (s, 2H), 3.10–2.95 (m, 2H), 2.65–2.50 (m, 2H), 2.20–2.00 (m, 5H), 0.98 (d, J=6.6 Hz, 6H).

REFERENCE EXAMPLE 8

3-(3-cyclopentyloxy-4-methoxyphenyl)-2,4-bis(ethoxycarbonyl)-5-hydroxy-5-methylcyclohexan-1-one

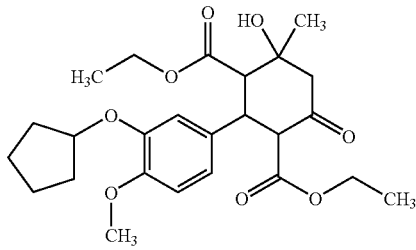

3-Cyclopentyloxy-4-methoxybenzaldehyde (30 g) and ethyl acetoacetate (33.36 ml) were dissolved in ethanol (7 ml), and piperidine (4 ml) was added thereto, followed by stirring at room temperature overnight. Ethanol was added to the reaction mixture, and filtered after solids were broken. The filtrate was washed with ethanol to thereby obtain the title compound (37.1 g) having the following physical properties.

TLC: Rf 0.55 (hexane:ethyl acetate=1:1);

NMR (DMSO-$d_6$): δ 6.87 (d, J=1.8 Hz, 1H), 6.81 (d, J=8.4 Hz, 1H), 6.75 (dd, J=8.4, 1.8 Hz, 1H), 4.83 (s, 1H), 4.75–4.69 (m, 1H), 3.95–3.70 (m, 6H), 3.67 (s, 3H), 3.26 (d, J=12.0 Hz, 1H), 2.90 (d, J=13.5 Hz, 1H), 2.31 (d, J=13.5 Hz, 1H), 1.90–1.78 (m, 2H), 1.78–1.63 (m, 4H), 1.63–1.53 (m, 2H), 1.23 (s, 3H), 0.96 (t, J=7.2 Hz, 3H), 0.87 (t, J=7.2 Hz, 3H).

REFERENCE EXAMPLE 9

3-(3-cyclopentyloxy-4-methoxyphenyl)-3-carboxymethylpropanoic acid

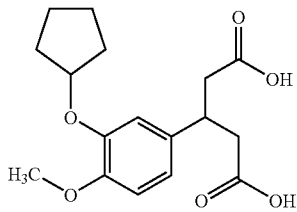

The compound (37.1 g) prepared in Reference Example 8 was dissolved in ethanol (370 ml) and tetrahydrofuran (200 ml), and sodium hydroxide (200 g) and water (200 ml) were added thereto, followed by refluxing under heating for 5 hours. The reaction mixture was cooled to room temperature, and ethanol was evaporated under reduced pressure. The reaction mixture was neutralized with concentrated hydrochloric acid (410 ml) while cooling on ice, and extracted with ethyl acetate. The extract was washed with water and saturated saline in this order, dried with anhydrous magnesium sulfate, and concentrated under reduced pressure to thereby obtain the title compound (26.28 g) having the following physical properties. The resulting compound was used without purification in the subsequent reaction.

TLC: Rf 0.58 (chloroform:methanol=5:1);

NMR (DMSO-$d_6$): δ 12.01 (br, 2H), 6.83–6.79 (m, 2H), 6.72 (dd, J=8.3, 2.0 Hz, 1H), 4.77–4.71 (m, 1H), 3.68 (s, 3H), 3.38–3.30 (m, 1H), 2.59 (dd, J=15.6, 6.3 Hz, 2H), 2.46 (dd, J=15.6, 8.4 Hz, 2H), 1.92–1.78 (m, 2H), 1.76–1.62 (m, 4H), 1.62–1.46 (m, 2H).

REFERENCE EXAMPLE 10

4-(3-cyclopentyloxy-4-methoxyphenyl)piperidin-2,6-dione

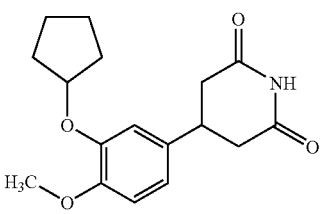

Urea (14.5 g) was added to the compound (26.28 g) prepared in Reference Example 9, followed by stirring at 165° C. for 4 hours. The reaction mixture was cooled to room temperature, and dichloromethane (150 ml) was added thereto. Insoluble materials were filtered. The filtrate was concentrated under reduced pressure. Ethyl acetate was added to the residue, and the residue was broken, followed by recrystallization. The resulting crystals were filtered and dried to thereby obtain the title compound (14.02 g) having the following physical properties.

TLC: Rf 0.77 (chloroform:methanol=5:1);

NMR (DMSO-$d_6$): δ 10.79 (s, 1H), 6.89–6.85 (m, 2H), 6.75 (dd, J=8.4, 2.1 Hz, 1H), 4.76 (m, 1H), 3.70 (s, 3H), 3.35 (m, 1H), 2.77 (dd, J=16.8, 10.8 Hz, 2H), 2.61 (dd, J=16.8, 4.7 Hz, 2H), 1.95–1.80 (m, 2H), 1.78–1.61 (m, 4H), 1.61–1.50 (m, 2H).

REFERENCE EXAMPLE 11

4-(3-cyclopentyloxy-4-methoxyphenyl)piperidine.hydrochloride

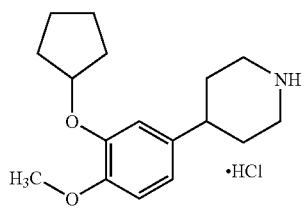

Lithium aluminum hydride (7.0 g) was suspended in tetrahydrofuran (150 ml), and a tetrahydrofuran (150 ml) solution of the compound (7 g) prepared in Reference Example 10 was added dropwise thereto at the insider temperature of 30° C. or less under ice-cooling, followed by stirring at room temperature for 3 hours. The reaction mixture was ice-cooled, and a saturated aqueous sodium sulfate solution (30 ml) was added dropwise thereto at the insider temperature of 30° C. or less, followed by stirring at room temperature for 1 hour. To the reaction mixture, ether (200 ml) and anhydrous magnesium sulfate were added, followed by stirring at room temperature for 2 hours. The reaction mixture was filtered with celite, and the filtrate was concentrated under reduced pressure. A 4 N hydrogen chloride-ethyl acetate solution (6 ml) was added to the residue, and the mixture was stirred and then concentrated under reduced pressure to thereby obtain the title compound (7.2 g) having the following physical properties.

TLC: Rf 0.15 (chloroform:methanol=9:1);

NMR (DMSO-$d_6$): δ 6.83 (d, J=8.1 Hz, 1H), 6.74 (d, J=1.9 Hz, 1H), 6.68 (dd, J=8.1, 1.9 Hz, 1H), 4.75 (m, 1H), 3.68 (s, 3H), 3.36 (m, 1H), 3.31 (br, 2H), 3.02–2.94 (m, 2H), 2.58–2.52 (m, 2H), 1.94–1.39 (m, 12H).

EXAMPLE 21

2-(4-(3-cyclopentyloxy-4-methoxyphenyl)piperidin-1-yl)acetic acid.ethyl ester

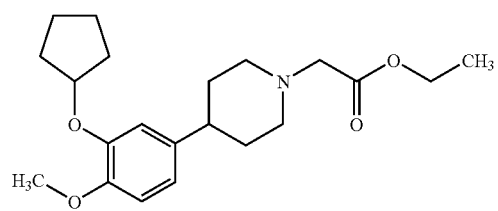

The compound of the present invention having the following physical properties was obtained in the same manner as in Example 1 using the compound prepared in Reference Example 11 instead of the compound prepared in Reference Example 4.

TLC: Rf 0.61(hexane:ethyl acetate=1:1);

NMR (CDCl$_3$): δ 6.82–6.71 (m, 3H), 4.75 (m, 1H), 4.21 (q, J=7.2 Hz, 2H), 3.82 (s, 3H), 3.25 (s, 2H), 3.10–3.02 (m, 2H), 2.43 (m, 1H), 2.33–2.23 (m, 2H), 1.95–1.75 (m, 10H), 1.70–1.50 (m, 2H), 1.29 (t, J=7.2 Hz, 3H).

EXAMPLE 22

2-(4-(3-cyclopentyloxy-4-methoxyphenyl)piperidin-1-yl)acetic acid

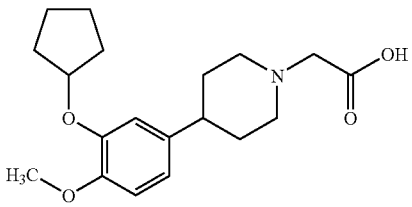

The compound of the present invention having the following physical properties was obtained in the same manner as in Example 2 using the compound prepared in Example 21 instead of the compound prepared in Example 1.

TLC: Rf 0.44 (chloroform:methanol=5:1);

NMR (DMSO-$d_6$): δ 6.88 (d, J=8.1 Hz, 1H), 6.79 (d, J=1.8 Hz, 1H), 6.73 (dd, J=8.1, 1.8 Hz, 1H), 4.79–4.72 (m, 1H), 4.11 (s, 2H), 3.70 (s, 3H), 3.59–3.49 (m, 2H), 3.32 (br, 1H), 3.18–3.05 (m, 2H), 2.74–2.68 (m, 1H), 2.04–1.80 (m, 6H), 1.77–1.63 (m, 4H), 1.63–1.50 (m, 2H).

FORMULATION EXAMPLE 1

The following components were admixed in a conventional method and punched out to obtain 100 tablets each containing 50 mg of the active ingredient.

| | |
|---|---|
| N-hydroxy-2-(4-(3-cyclopentyloxy-4-methoxyphenyl)-4-cyanopiperidin-1-yl)acetamide.hydrochloride | 5.0 g |
| Carboxymethyl cellulose calcium (disintegrating agent) | 0.2 g |
| Magnesium stearate (lubricant) | 0.1 g |
| Microcrystalline cellulose | 4.7 g |

FORMULATION EXAMPLE 2

The following components were admixed in a conventional method, and the solution was sterilized in a conventional method, placed at 5 ml into ampoules and freeze-dried in a conventional method to thereby obtain 100 ampoules each containing 20 mg of the active ingredient.

| | |
|---|---|
| N-Hydroxy-2-(4-3-cyclopentyloxy-4-methoxyphenyl)-4-cyanopiperidin-1-yl)acetamide.hydrochloride | 2.0 g |
| Mannitol | 20 g |
| Distilled water | 1000 ml |

What is claimed is:

1. A piperidine derivative compound represented by formula (I):

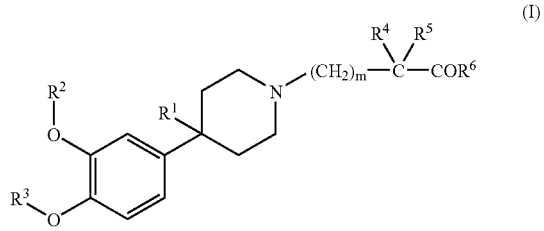

(wherein $R^1$ represents 1) a hydrogen atom or 2) a cyano group;

$R^2$ and $R^3$ each independently represents 1) a C1–8 alkyl group, 2) a C3–7 cycloalkyl group, 3) a C1–8 alkyl group substituted with a C3–7 cycloalkyl group, 4) a C1–8 alkyl group substituted with 1 to 3 halogen atom(s), 5) a hydrogen atom, 6) a C1–8 alkyl group substituted with a phenyl group, 7) a C1–8 alkyl group substituted with a C1–8 alkoxy group, or

8)

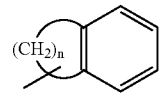

(in which n represents 1 to 5);

$R^4$ and $R^5$ each independently represents 1) a hydrogen atom or 2) a C1–8 alkyl group, or $R^4$ and $R^5$ are taken together with the binding carbon atom to represent a C3–7 saturated carbocyclic ring;

$R^6$ represents 1) a hydroxyl group, 2) a C1–8 alkoxy group, 3) —NHOH, or 4) a C1–8 alkoxy group substituted with a phenyl group; and m is 0 or an integer of 1 to 4)

or a nontoxic salt thereof.

2. The piperidine derivative compound according to claim 1, wherein the compound represented by formula (I) is represented by formula (I'):

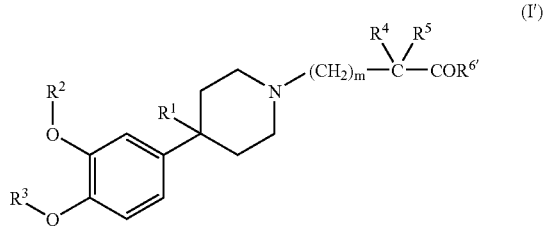

(wherein $R^{6'}$ represents 1) a hydroxyl group, 2) a C1–8 alkoxy group, or 4) a C1–8 alkoxy group substituted with a phenyl group; and other symbols have the same meaning as defined in claim 1), or a nontoxic salt thereof.

3. The piperidine derivative compound according to claim 1, wherein the compound represented by formula (I) is represented by formula (I"):

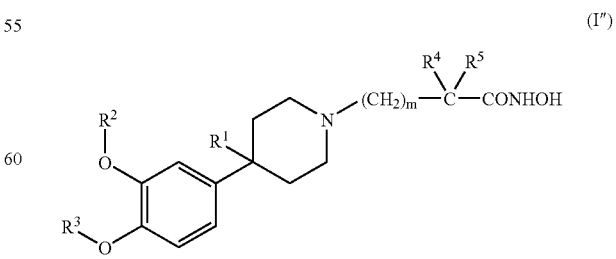

(wherein all symbols have the same meaning as defined in claim 1), or a nontoxic salt thereof.

4. The piperidine derivative compound according to claim 2, wherein $R^{6'}$ is a hydroxyl group.

5. The piperidine derivative compound according to claim 2, wherein $R^{6'}$ is a C1–8 alkoxy group or a C1–8 alkoxy group substituted with a phenyl group.

6. The piperidine derivative compound according to claim 4, which is (1) 2-(4-(3-cyclopentyloxy-4-methoxyphenyl)-4-cyanopiperidin-1-yl)acetic acid,
(2) 2-(4-(3,4-dimethoxyphenyl)-4-cyanopiperidin-1-yl)acetic acid,
(3) 2-(4-(3-ethoxy-4-methoxyphenyl-4-cyanopiperidin-1-yl)acetic acid,
(4) 2-(4-(3-cyclopropylmethoxy-4-methoxyphenyl)-4-cyanopiperidin-1-yl)acetic acid,
(5) 2-(4-(3-isopropyloxy-4-methoxyphenyl)-4-cyanopiperidin-1-yl)acetic acid,
(6) 2-(4-(3-cyclobutyloxy-4-methoxyphenyl)-4-cyanopiperidin-1-yl)acetic acid,
(7) 2-(4-(3-cyclopentyloxy-4-methoxyphenyl)-4-cyanopiperidin-1-yl)propanoic acid,
(8) 4-(4-(3-cyclopentyloxy-4-methoxyphenyl)-4-cyanopiperidin-1-yl))butanoic acid,
(9) 2-(4-(3-cyclopentyloxy-4-methoxyphenyl)-4-cyanopiperidin-1-yl))butanoic acid,
(10) 2-(4-(3-cyclopentyloxy-4-difluoromethoxyphenyl)-4-cyanopiperidin-1-yl)acetic acid,
(11) 2-(4-(3-cyclopentyloxy-4-ethoxyphenyl)-4-cyanopiperidin-1-yl)acetic acid,
(12) 2-(4-(3-cyclopentyloxy-4-ethoxyphenyl)-4-cyanopiperidin-1-yl)propanoic acid,
(13) 2-(4-(3-cyclopentyloxy-4-isopropyloxyphenyl)-4-cyanopiperidin-1-yl)acetic acid,
(14) 2-(4-(3-isopropyloxy-4-difluoromethoxyphenyl)-4-cyanopiperidin-1-yl)acetic acid,
(15) 2-(4-(3-cyclohexyloxy-4-difluoromethoxyphenyl)-4-cyanopiperidin-1-yl)acetic acid,
(16) 3-(4-(3-cyclopentyloxy-4-methoxyphenyl)-4-cyanopiperidin-1-yl)propanoic acid,
(17) (2R)-2-(4-(3-cyclopentyloxy-4-methoxyphenyl)-4-cyanopiperidin-1-yl)propanoic acid,
(18) (2S)-2-(4-(3-cyclopentyloxy-4-methoxyphenyl)-4-cyanopiperidin-1-yl)propanoic acid,
(19) 2-(4-(3-cyclopentyloxy-4-methoxyphenyl)-4-cyanopiperidin-1-yl)-2-methylpropanoic acid,
(20) 1-(4-(3-cyclopentyloxy-4-methoxyphenyl)-4-cyanopiperidin-1-yl)cyclopropanecarboxylic acid,
(21) 1-(4-(3-ethoxy-4-methoxyphenyl-4-cyanopiperidin-1-yl)cyclopropanecarboxylic acid,
(22) 1-(4-(3-cyclopropylmethoxy-4-methoxyphenyl)-4-cyanopiperidin-1-yl)cyclopropanecarboxylic acid,
(23) 1-(4-(3-cyclobutyloxy-4-methoxyphenyl)-4-cyanopiperidin-1-yl)cyclopropanecarboxylic acid,
(24) 2-(4-(3-(indan-2-yloxy)-4-methoxyphenyl)-4-cyanopiperidin-1-yl)acetic acid,
(25) 2-(4-(3-cyclobutyloxy-4-difluoromethoxyphenyl)-4-cyanopiperidin-1-yl)acetic acid,
(26) 2-(4-(3-(indan-2-yloxy)-4-difluoromethoxyphenyl)-4-cyanopiperidin-1-yl)acetic acid,
(27) 2-(4-(3-cyclopropylmethoxy-4-difluromethoxyphenyl)-4-cyanopiperidin-1-yl)acetic acid,
(28) 2-(4-(3-cyclobutylmethoxy-4-difluromethoxyphenyl)-4-cyanopiperidin-1-yl)acetic acid,
(29) 2-(4-(3-ethoxy-4-difluromethoxyphenyl)-4-cyanopiperidin-1-yl)acetic acid,
(30) 2-(4-(3-butoxy-4-difluromethoxyphenyl)-4-cyanopiperidin-1-yl)acetic acid,
(31) 2-(4-(3-propoxy-4-difluromethoxyphenyl)-4-cyanopiperidin-1-yl)acetic acid,
(32) 2-(4-(3-(2-methylpropoxy)-4-difluromethoxyphenyl)-4-cyanopiperidin-1-yl)acetic acid, or
(33) 2-(4-(3-cyclopentyloxy-4-methoxyphenyl)piperidin-1-yl)acetic acid.

7. The piperidine derivative compound according to claim 5, which is (1) 2-(4-(3-cyclopentyloxy-4-methoxyphenyl)-4-cyanopiperidin-1-yl)acetic acid.ethyl ester,
(2) 2-(4-(3,4-dimethoxyphenyl)-4-cyanopiperidin-1-yl)acetic acid.ethyl ester,
(3) 2-(4-(3-ethoxy-4-methoxyphenyl-4-cyanopiperidin-1-yl)acetic acid.ethyl ester,
(4) 2-(4-(3-cyclopropylmethoxy-4-methoxyphenyl)-4-cyanopiperidin-1-yl)acetic acid.ethyl ester,
(5) 2-(4-(3-isopropyloxy-4-methoxyphenyl)-4-cyanopiperidin-1-yl)acetic acid.ethyl ester,
(6) 2-(4-(3-cyclobutyloxy-4-methoxyphenyl)-4-cyanopiperidin-1-yl)acetic acid.ethyl ester,
(7) 2-(4-(3-cyclopentyloxy-4-methoxyphenyl)-4-cyanopiperidin-1-yl)propanoic acid.ethyl ester,
(8) 4-(4-(3-cyclopentyloxy-4-methoxyphenyl)-4-cyanopiperidin-1-yl)butanoic acid.ethyl ester,
(9) 2-(4-(3-cyclopentyloxy-4-methoxyphenyl)-4-cyanopiperidin-1-yl)butanoic acid.ethyl ester,
(10) 2-(4-(3-cyclopentyloxy-4-difluoromethoxyphenyl)-4-cyanopiperidin-1-yl)acetic acid.ethyl ester,
(11) 2-(4-(3-cyclopentyloxy-4-ethoxyphenyl)-4-cyanopiperidin-1-yl)acetic acid.ethyl ester,
(12) 2-(4-(3-cyclopentyloxy-4-ethoxyphenyl)-4-cyanopiperidin-1-yl)propanoic acid.ethyl ester,
(13) 2-(4-(3-cyclopentyloxy-4-isopropyloxyphenyl)-4-cyanopiperidin-1-yl)acetic acid.ethyl ester,
(14) 2-(4-(3-isopropyloxy-4-difluoromethoxyphenyl)-4-cyanopiperidin-1-yl)acetic acid.ethyl ester,
(15) 2-(4-(3-cyclohexyloxy-4-difluoromethoxyphenyl)-4-cyanopiperidin-1-yl)acetic acid.ethyl ester,
(16) 3-(4-(3-cyclopentyloxy-4-methoxyphenyl)-4-cyanopiperidin-1-yl)propanoic acid.methyl ester,
(17) (2R)-2-(4-(3-cyclopentyloxy-4-methoxyphenyl)-4-cyanopiperidin-1-yl)propanoic acid.methyl ester,
(18) (2S)-2-(4-(3-cyclopentyloxy-4-methoxyphenyl)-4-cyanopiperidin-1-yl)propanoic acid.methyl ester,
(19) 2-(4-(3-cyclopentyloxy-4-methoxyphenyl)-4-cyanopiperidin-1-yl)-2-methylpropanoic acid.benzyl ester,
(20) 1-(4-(3-cyclopentyloxy-4-methoxyphenyl)-4-cyanopiperidin-1-yl)cyclopropanecarboxylic acid.benzyl ester,
(21) 1-(4-(3-ethoxy-4-methoxyphenyl-4-cyanopiperidin-1-yl)cyclopropanecarboxylic acid.benzyl ester,
(22) 1-(4-(3-methoxymethoxy-4-methoxyphenyl)-4-cyanopiperidin-1-yl)cyclopropanecarboxylic acid.benzyl ester,
(23) 1-(4-(3-hydroxy-4-methoxyphenyl)-4-cyanopiperidin-1-yl)cyclopropanecarboxylic acid.benzyl ester,
(24) 1-(4-(3-cyclopropylmethoxy-4-methoxyphenyl)-4-cyanopiperidin-1-yl)cyclopropanecarboxylic acid.benzyl ester,
(25) 1-(4-(3-cyclobutyloxy-4-methoxyphenyl)-4-cyanopiperidin-1-yl)cyclopropanecarboxylic acid.benzyl ester,
(26) 2-(4-(3-benzyloxy-4-methoxyphenyl)-4-cyanopiperidin-1-yl)acetic acid.ethyl ester,
(27) 2-(4-(3-benzyloxy-4-difluoromethoxyphenyl)-4-cyanopiperidin-1-yl)acetic acid.methyl ester,

(28) 2-(4-(3-hydroxy-4-methoxyphenyl)-4-cyanopiperidin-1-yl)acetic acid.ethyl ester,
(29) 2-(4-(3-hydroxy-4-difluoromethoxyphenyl)-4-cyanopiperidin-1-yl)acetic acid.methyl ester,
(30) 2-(4-(3-(indan-2-yloxy)-4-methoxyphenyl)-4-cyanopipendin-1-yl)acetic acid.ethyl ester,
(31) 2-(4-(3-cyclobutyloxy-4-difluoromethoxyphenyl)-4-cyanopipendin-1-yl)acetic acid.methyl ester,
(32) 2-(4-(3-(indan-2-yloxy)-4-difluoromethoxyphenyl)-4-cyanopiperidin-1-yl)acetic acid.methyl ester,
(33) 2-(4-(3-cyclopropylmethoxy-4-difluromethoxyphenyl)-4-cyanopiperidin-1-yl)acetic acid.methyl ester,
(34) 2-(4-(3-cyclobutylmethoxy-4-difluromethoxyphenyl)-4-cyanopiperidin-1-yl)acetic acid.methyl ester,
(35) 2-(4-(3-ethoxy-4-difluromethoxyphenyl)-4-cyanopiperidin-1-yl)acetic acid.methyl ester,
(36) 2-(4-(3-butoxy-4-difluromethoxyphenyl)-4-cyanopipendin-1-yl)acetic acid.methyl ester,
(37) 2-(4-(3-propoxy-4-difluromethoxyphenyl)-4-cyanopiperidin-1-yl)acetic acid.methyl ester,
(38) 2-(4-(3-(2-methylpropoxy)-4-difluromethoxyphenyl)-4-cyanopiperidin-1-yl)acetic acid.methyl ester, or
(39) 2-(4-(3-cyclopentyloxy-4-methoxyphenyl)piperidin-1-yl)acetic acid.ethyl ester.

8. The piperidine derivative compound according to claim 3, which is
(1) N-hydroxy-2-(4-(3-cyclopentyloxy-4-methoxyphenyl)-4-cyanopiperidin-1-yl)acetamide,
(2) N-hydroxy-2-(4-(3,4-dimethoxyphenyl)-4-cyanopiperidin-1-yl)acetamide,
(3) N-hydroxy-2-(4-(3-ethoxy-4-methoxyphenyl-4-cyanopiperidin-1-yl)acetamide,
(4) N-hydroxy-2-(4-(3-cyclopropylmethoxy-4-methoxyphenyl)-4-cyanopiperidin-1-yl)acetamide,
(5) N-hydroxy-2-(4-(3-isopropyloxy-4-methoxyphenyl)-4-cyanopiperidin-1-yl)acetamide,
(6) N-hydroxy-2-(4-(3-cyclobutyloxy-4-methoxyphenyl)-4-cyanopiperidin-1-yl)acetamide,
(7) N-hydroxy-2-(4-(3-cyclopentyloxy-4-methoxyphenyl)-4-cyanopiperidin-1-yl)propanamide,
(8) N-hydroxy-4-(4-(3-cyclopentyloxy-4-methoxyphenyl)-4-cyanopiperidin-1-yl)butanamide,
(9) N-hydroxy-2-(4-(3-cyclopentyloxy-4-methoxyphenyl)-4-cyanopiperidin-1-yl)butanamide,
(10) N-hydroxy-2-(4-(3-cyclopentyloxy-4-difluoromethoxyphenyl)-4-cyanopiperidin-1-yl)acetamide,
(11) N-hydroxy-2-(4-(3-cyclopentyloxy-4-ethoxyphenyl)-4-cyanopiperidin-1-yl)acetamide,
(12) N-hydroxy-2-(4-(3-cyclopentyloxy-4-ethoxyphenyl)-4-cyanopiperidin-1-yl)propanamide,
(13) N-hydroxy-2-(4-(3-cyclopentyloxy-4-isopropyloxyphenyl)-4-cyanopiperidin-1-yl)acetamide,
(14) N-hydroxy-3-(4-(3-cyclopentyloxy-4-methoxyphenyl)-4-cyanopiperidin-1-yl)propanamide,
(15) (2R)-N-hydroxy-2-(4-(3-cyclopentyloxy-4-methoxyphenyl)-4-cyanopiperidin-1-yl)propanamide,
(16) (2S)-N-hydroxy-2-(4-(3-cyclopentyloxy-4-methoxyphenyl)-4-cyanopiperidin-1-yl)propanamide,
(17) N-hydroxy-2-(4-(3-cyclopentyloxy-4-methoxyphenyl)-4-cyanopiperidin-1-yl)-2-methylpropanamide,
(18) N-hydroxy-1-(4-(3-cyclopentyloxy-4-methoxyphenyl)-4-cyanopiperidin-1-yl)cyclopropanecarboxamide,
(19) N-hydroxy-1-(4-(3-ethoxy-4-methoxyphenyl-4-cyanopiperidin-1-yl)cyclopropanecarboxamide,
(20) N-hydroxy-1-(4-(3-cyclopropylmethoxy-4-methoxyphenyl)-4-cyanopiperidin-1-yl)cyclopropanecarboxamide, or
(21) N-hydroxy-1-(4-(3-cyclobutyloxy-4-methoxyphenyl)-4-cyanopiperidin-1-yl)cyclopropanecarboxamide.

9. A composition which comprises, as an active ingredient, the piperidine derivative compound represented by formula (I) according to claim 1 or a nontoxic salt thereof and a pharmaceutically acceptable carrier.

10. 2-(4-(3-Cyclopentyloxy-4-difluoromethoxyphenyl)-4-cyanopipendin-1-yl)acetic acid or a nontoxic salt thereof.

* * * * *